US008790724B2

(12) United States Patent
Jia

(10) Patent No.: US 8,790,724 B2
(45) Date of Patent: Jul. 29, 2014

(54) FORMULATION OF DUAL CYCLOXYGENASE (COX) AND LIPOXYGENASE (LOX) INHIBITORS FOR MAMMAL SKIN CARE

(75) Inventor: Qi Jia, Olympia, WA (US)

(73) Assignee: Unigen, Inc., Seattle, WA (US)

(*) Notice: Subject to any disclaimer, the term of this patent is extended or adjusted under 35 U.S.C. 154(b) by 0 days.

(21) Appl. No.: 13/028,853

(22) Filed: Feb. 16, 2011

(65) Prior Publication Data
US 2011/0207806 A1 Aug. 25, 2011

Related U.S. Application Data

(62) Division of application No. 10/817,330, filed on Apr. 2, 2004, now abandoned.

(60) Provisional application No. 60/460,736, filed on Apr. 4, 2003.

(51) Int. Cl.
A61K 36/539 (2006.01)
A61K 36/00 (2006.01)

(52) U.S. Cl.
USPC .......................................... 424/741; 424/725

(58) Field of Classification Search
None
See application file for complete search history.

(56) References Cited

U.S. PATENT DOCUMENTS

| 3,686,872 | A | 8/1972 | Whitworth et al. ................ 61/36 |
| 3,706,581 | A | 12/1972 | Whitworth et al. ................ 61/36 |
| 4,035,510 | A * | 7/1977 | Van Scott et al. ............. 514/667 |
| 4,201,776 | A | 5/1980 | Naito et al. |
| 4,268,517 | A | 5/1981 | Niebes et al. .................. 424/283 |
| 4,374,824 | A | 2/1983 | Wahmi ............................ 424/58 |
| 4,515,804 | A | 5/1985 | Marti et al. |
| 4,627,977 | A | 12/1986 | Gaffar et al. |
| 4,946,684 | A | 8/1990 | Blank et al. ................... 424/441 |
| 4,965,067 | A | 10/1990 | Wietfeldt |
| 5,037,635 | A | 8/1991 | Nabi et al. |
| 5,096,701 | A | 3/1992 | White, Jr. et al. |
| 5,098,709 | A | 3/1992 | Kang |
| 5,156,835 | A | 10/1992 | Nabi et al. |
| 5,437,856 | A | 8/1995 | Lukacovic et al. |
| 5,443,983 | A | 8/1995 | Ochoa et al. ................ 435/240.2 |
| 5,470,589 | A | 11/1995 | Shi ................................. 424/698 |
| 5,545,411 | A | 8/1996 | Chancellor ................... 424/439 |
| 5,585,371 | A | 12/1996 | Lardy |
| 5,589,160 | A | 12/1996 | Rice ............................... 424/49 |
| 5,605,929 | A | 2/1997 | Liao et al. .................... 514/456 |
| 5,643,598 | A | 7/1997 | Meybeck ....................... 424/450 |
| 5,650,432 | A | 7/1997 | Walker et al. ................. 514/456 |
| 5,650,433 | A | 7/1997 | Watanabe et al. ............. 514/456 |
| 5,651,987 | A | 7/1997 | Fuisz ............................. 424/488 |
| 5,756,538 | A | 5/1998 | Cassels et al. ................ 514/456 |
| 5,766,614 | A | 6/1998 | Yong |
| 5,773,014 | A | 6/1998 | Perrier et al. ................ 424/401 |
| 5,795,911 | A | 8/1998 | Cheng et al. .................. 514/456 |
| 5,804,168 | A * | 9/1998 | Murad ............................ 424/59 |
| 5,852,057 | A * | 12/1998 | Muto et al. .................... 514/560 |
| 5,858,371 | A | 1/1999 | Singh et al. ................. 424/195.1 |
| 5,886,029 | A | 3/1999 | Dhaliwal ....................... 514/456 |
| 5,886,155 | A | 3/1999 | Armah et al. ................. 530/395 |
| 5,908,628 | A | 6/1999 | Hou |
| 5,922,756 | A | 7/1999 | Chan |

(Continued)

FOREIGN PATENT DOCUMENTS

| CA | 2 126 513 A1 | 1/1995 |
| CA | 2 484 192 A1 | 11/2002 |

(Continued)

OTHER PUBLICATIONS

Afolayan et al., "The antimicrobial activity of 3,5,7-trihydroxyflavone isolated from the shoots of *Helichrysum aureonitens*," *Journal of Ethnopharmacology* 57:177-181, 1997.

Agarwal et al., "Protection Against Ultraviolet B Radiation-Induced Effects in the Skin of SKH-1 Hairless Mice by a Polyphenolic Fraction Isolated from Green Tea," *Photochemistry and Photobiology* 58(5):695-700, 1993.

(Continued)

*Primary Examiner* — Chris R Tate
*Assistant Examiner* — Randall Winston
(74) *Attorney, Agent, or Firm* — Seed IP Law Group PLLC

(57) ABSTRACT

The present invention provides a novel composition of matter comprised of a mixture of two specific classes of compounds—Free-B-Ring flavonoids and flavans—for use in the prevention and treatment of diseases and conditions associated with the skin. This composition of matter simultaneously inhibits cyclooxygenase (COX) and lipoxygenase (LOX) enzymatic activity in normal, aged and damaged dermal cells and tissues. This invention further provides a method for the prevention and treatment of diseases and conditions of the skin mediated by cyclooxygenase (COX) and lipoxygenase (LOX). The method for preventing and treating COX and LOX mediated diseases and conditions of the skin is comprised of topically administering to a host in need thereof a therapeutically effective amount of a composition comprising a mixture of Free-B-Ring flavonoids and flavans synthesized and/or isolated from a single plant or multiple plants, preferably in the *Scutellaria* and *Acacia* genus of plants and pharmaceutically and/or cosmetically acceptable carriers. Finally the present invention provides a method for the prevention and treatment of COX and LOX mediated diseases and conditions, including but not limited to sun burns, thermal burns, acne, topical wounds, minor inflammatory conditions caused by fungal, microbial and viral infections, vitilago, systemic lupus erythromatosus, psoriasis, carcinoma, melanoma, as well as other mammal skin cancers, skin damage resulting from exposure to ultraviolet (UV) radiation, chemicals, heat, wind and dry environments, wrinkles, saggy skin, lines and dark circles around the eyes, dermatitis and other allergy related conditions of the skin. Use of the composition described herein also affords the benefit of smooth and youthful skin with improved elasticity, reduced and delayed aging, enhanced youthful appearance and texture, and increased flexibility, firmness, smoothness and suppleness.

35 Claims, 8 Drawing Sheets

(56) References Cited

U.S. PATENT DOCUMENTS

| | | | |
|---|---|---|---|
| 5,962,517 A | 10/1999 | Murad | 514/474 |
| 5,968,973 A | 10/1999 | Cheng et al. | 514/456 |
| 6,080,401 A | 6/2000 | Reddy et al. | 424/93.3 |
| 6,083,921 A | 7/2000 | Xu | 514/25 |
| 6,093,403 A | 7/2000 | Huo et al. | 424/195.1 |
| 6,113,909 A | 9/2000 | Han et al. | |
| 6,126,940 A | 10/2000 | Takahashi et al. | 424/195.1 |
| 6,126,950 A | 10/2000 | Bindra et al. | 424/401 |
| 6,193,977 B1 | 2/2001 | Han et al. | |
| 6,194,469 B1 | 2/2001 | Nair et al. | |
| 6,197,808 B1 | 3/2001 | Cheng et al. | 514/456 |
| 6,217,875 B1 | 4/2001 | Murai et al. | 424/195.1 |
| 6,221,341 B1 | 4/2001 | Montgomery | |
| 6,235,294 B1 | 5/2001 | Perrier et al. | 424/401 |
| 6,241,972 B1 | 6/2001 | Herms et al. | |
| 6,248,341 B1 | 6/2001 | Anderson et al. | 424/401 |
| 6,264,926 B1 | 7/2001 | Farooqi et al. | |
| 6,264,995 B1 | 7/2001 | Newmark et al. | 424/725 |
| 6,280,751 B1 | 8/2001 | Fletcher et al. | |
| 6,290,995 B1 | 9/2001 | Xinxian | 424/773 |
| 6,319,523 B1 | 11/2001 | Zhou | 424/725 |
| 6,333,304 B1 | 12/2001 | Bath et al. | |
| 6,387,416 B1 | 5/2002 | Newmark et al. | 424/725 |
| 6,391,346 B1 | 5/2002 | Newmark et al. | 424/756 |
| 6,391,872 B1 | 5/2002 | Marfat | 514/218 |
| 6,475,530 B1 | 11/2002 | Kuhrts | 424/725 |
| 6,555,573 B2 | 4/2003 | Rosenbloom | 514/456 |
| 6,576,660 B1 | 6/2003 | Liao et al. | |
| 6,685,971 B2 | 2/2004 | Xu | 424/725 |
| 7,045,158 B2 | 5/2006 | Wolfson et al. | 424/741 |
| 7,074,438 B2 | 7/2006 | Xu | |
| 7,108,868 B2 | 9/2006 | Jia et al. | |
| 7,189,385 B2 | 3/2007 | Montgomery | |
| 7,192,611 B2 | 3/2007 | Jia et al. | |
| 7,514,469 B2 | 4/2009 | Jia | 514/456 |
| 7,531,521 B2 | 5/2009 | Burnett et al. | |
| 7,615,239 B2 | 11/2009 | Santo et al. | 424/725 |
| 7,674,830 B2 | 3/2010 | Jia | |
| 7,695,743 B2 | 4/2010 | Jia et al. | 424/725 |
| 7,897,182 B2 | 3/2011 | Woo et al. | |
| 7,972,632 B2 | 7/2011 | Jia | |
| 8,034,387 B2 | 10/2011 | Jia et al. | |
| 8,124,134 B2 | 2/2012 | Jia et al. | |
| 8,148,416 B2 | 4/2012 | El-Naggar et al. | |
| 8,247,007 B2 | 8/2012 | Woo et al. | |
| 8,535,735 B2 | 9/2013 | Jia et al. | |
| 2001/0002407 A1 | 5/2001 | Nair et al. | |
| 2001/0026813 A1 | 10/2001 | Kim et al. | |
| 2001/0046963 A1 | 11/2001 | Wenzel et al. | |
| 2002/0086042 A1* | 7/2002 | Delrieu et al. | 424/401 |
| 2002/0086070 A1 | 7/2002 | Kuhrts | 424/773 |
| 2002/0122836 A1 | 9/2002 | Obukowicz et al. | 424/764 |
| 2002/0136784 A1 | 9/2002 | Obukowicz et al. | 424/725 |
| 2002/0146467 A1 | 10/2002 | Jung et al. | |
| 2003/0013463 A1 | 1/2003 | Yen | |
| 2003/0045562 A1 | 3/2003 | El-Naggar et al. | |
| 2003/0105030 A1 | 6/2003 | Liao et al. | 514/27 |
| 2003/0113797 A1 | 6/2003 | Jia et al. | |
| 2003/0125264 A1 | 7/2003 | Malik | 514/27 |
| 2003/0165588 A1 | 9/2003 | Jia et al. | |
| 2003/0166583 A1 | 9/2003 | Yoa-Pu Hu et al. | 514/27 |
| 2003/0170186 A1 | 9/2003 | Geers et al. | 424/59 |
| 2003/0203857 A1 | 10/2003 | Ohnogi et al. | |
| 2004/0028639 A1 | 2/2004 | Maes et al. | |
| 2004/0057908 A1 | 3/2004 | Bowen et al. | |
| 2004/0220119 A1 | 11/2004 | Jia | |
| 2005/0049206 A1 | 3/2005 | Gong et al. | 514/27 |
| 2005/0096281 A1 | 5/2005 | Jia et al. | |
| 2006/0008749 A1 | 1/2006 | Sobel et al. | |
| 2006/0079467 A1 | 4/2006 | Jia et al. | 514/27 |
| 2006/0140881 A1 | 6/2006 | Xu et al. | |
| 2006/0141073 A1 | 6/2006 | Worrell et al. | |
| 2006/0177528 A1 | 8/2006 | Jia | |
| 2006/0204596 A1 | 9/2006 | Jia et al. | 424/725 |
| 2006/0269627 A1 | 11/2006 | Jia et al. | 424/757 |
| 2007/0065524 A1 | 3/2007 | Wang | |
| 2007/0135359 A1 | 6/2007 | Jia et al. | 514/27 |
| 2007/0264361 A1 | 11/2007 | Jo et al. | 424/729 |
| 2008/0096826 A1 | 4/2008 | Jia et al. | 514/27 |
| 2008/0107759 A1 | 5/2008 | Woo et al. | |
| 2008/0176811 A1 | 7/2008 | Geers et al. | |
| 2008/0214658 A1 | 9/2008 | Woo et al. | |
| 2008/0279969 A1 | 11/2008 | Jo et al. | |
| 2009/0304830 A1 | 12/2009 | Jo et al. | |
| 2011/0117224 A1 | 5/2011 | Woo et al. | |
| 2011/0245333 A1 | 10/2011 | Jia et al. | |
| 2012/0329863 A1 | 12/2012 | Jia et al. | |
| 2013/0012463 A1 | 1/2013 | Jia et al. | |
| 2013/0064910 A1 | 3/2013 | Woo et al. | |

FOREIGN PATENT DOCUMENTS

| | | |
|---|---|---|
| CA | 2 451 844 | 9/2003 |
| CN | 1057196 A | 10/1993 |
| CN | 1093914 A | 10/1994 |
| CN | 1096680 | 12/1994 |
| CN | 1101856 | 4/1995 |
| CN | 1177492 A | 4/1998 |
| CN | 1189365 A | 8/1998 |
| CN | 1043406 | 5/1999 |
| CN | 1288968 A | 9/1999 |
| CN | 1265895 A | 9/2000 |
| CN | 1285202 | 2/2001 |
| CN | 1686187 A | 10/2005 |
| EP | 0 742 012 | 11/1996 |
| EP | 0 633 022 B1 | 2/1997 |
| EP | 0 296 625 A2 | 12/1998 |
| EP | 0 956 867 | 11/1999 |
| EP | 1 147 764 | 10/2001 |
| FR | 2 651 132 | 3/1991 |
| FR | 2 687 572 | 2/1992 |
| GB | 2 024 817 A | 1/1980 |
| GB | 2 306 321 | 5/1997 |
| JP | 57-038721 A | 3/1982 |
| JP | 61-50921 A | 3/1986 |
| JP | 61-083179 A | 4/1986 |
| JP | 61-161219 | 7/1986 |
| JP | 61-161219 A | 7/1986 |
| JP | 61-238719 | 10/1986 |
| JP | 61-238719 A | 10/1986 |
| JP | 63-27435 A | 2/1988 |
| JP | 64-90124 A | 4/1989 |
| JP | 10-182415 A | 7/1989 |
| JP | 7-223941 | 3/1991 |
| JP | 3-240725 | 10/1991 |
| JP | 3-240725 A | 10/1991 |
| JP | 03-2515518 A | 11/1991 |
| JP | 05-271088 A | 10/1993 |
| JP | 5-331061 | 12/1993 |
| JP | 7-010768 | 1/1995 |
| JP | 7-017847 | 1/1995 |
| JP | 7-025761 A | 1/1995 |
| JP | 7-55895 b2 | 6/1995 |
| JP | 7-165598 A | 6/1995 |
| JP | 7-242555 A | 9/1995 |
| JP | 7-252158 A | 10/1995 |
| JP | 7-277942 | 10/1995 |
| JP | 7-277942 A | 10/1995 |
| JP | 8-026969 | 1/1996 |
| JP | 8-26969 A | 1/1996 |
| JP | 8-104628 | 4/1996 |
| JP | 9-94081 A | 4/1997 |
| JP | 9-227374 | 9/1997 |
| JP | 09278662 A | 10/1997 |
| JP | 10-025238 A | 1/1998 |
| JP | 10-25238 A | 1/1998 |
| JP | 10-130162 | 5/1998 |
| JP | 10-182415 | 7/1998 |
| JP | 10-182415 A | 7/1998 |
| JP | 10-287528 | 10/1998 |
| JP | 10-2875728 A | 10/1998 |
| JP | 11-140497 | 5/1999 |
| JP | 2000-044481 A | 2/2000 |
| JP | 2000-506901 A | 6/2000 |

(56) References Cited

FOREIGN PATENT DOCUMENTS

| JP | 2000-226329 A | 8/2000 |
|---|---|---|
| JP | 2000-319154 | 11/2000 |
| JP | 200319154 A * | 11/2000 |
| JP | 2001/187744 A | 7/2001 |
| JP | 2001-220353 | 8/2001 |
| JP | 2002-53484 | 2/2002 |
| JP | 2003-2820 A | 1/2003 |
| JP | 2003-0021640 A | 3/2003 |
| JP | 2003-081746 | 3/2003 |
| JP | 2003-212771 A | 7/2003 |
| JP | 2003-212786 A | 7/2003 |
| JP | 2004-244385 A | 9/2004 |
| JP | 2005-519100 A | 6/2005 |
| KR | 1996-0003725 A | 2/1996 |
| KR | 1996-0040370 A | 12/1996 |
| KR | 2001-0017481 A | 3/2001 |
| KR | 2001-0069130 A | 7/2001 |
| KR | 2002-0013675 A | 2/2002 |
| KR | 2002-0031608 A | 5/2002 |
| KR | 10-0465113 B1 | 12/2004 |
| KR | 10-0522579 B1 | 10/2005 |
| WO | 97/36497 | 10/1997 |
| WO | 98/19651 A1 | 5/1998 |
| WO | 98/40086 | 9/1998 |
| WO | 98/42363 A1 | 10/1998 |
| WO | 98/49256 A1 | 11/1998 |
| WO | 00/59523 | 10/2000 |
| WO | 00/67749 | 11/2000 |
| WO | 00/74662 A2 | 12/2000 |
| WO | 01/30341 A1 | 5/2001 |
| WO | 02/07745 A1 | 1/2002 |
| WO | 02/09699 A2 | 2/2002 |
| WO | 02/42429 A2 | 5/2002 |
| WO | WO0239973 A * | 5/2002 |
| WO | 02/47615 | 6/2002 |
| WO | 03/002134 A1 | 1/2003 |
| WO | 03/009825 | 2/2003 |
| WO | 03/015737 A1 | 2/2003 |
| WO | 03/015766 | 2/2003 |
| WO | 03/024470 | 3/2003 |
| WO | 03/082312 A1 | 10/2003 |
| WO | 03/092599 | 11/2003 |
| WO | 2004/058279 A1 | 7/2004 |
| WO | 2004/075844 A2 | 9/2004 |
| WO | 20018/089392 A1 | 10/2004 |
| WO | 2005/020932 A2 | 3/2005 |
| WO | 2006/045056 A2 | 4/2006 |
| WO | 2006/099217 A2 | 9/2006 |
| WO | 2008/044894 A1 | 4/2008 |

OTHER PUBLICATIONS

Amos et al., "The pharmacological effects of an aqueaous extract from acacia nilotica seeds," *Phytother. Res.* 13(8):683-685, 1999 (abstract only).
Ardlie et al., "Effects of Trifluoperazine on Platelet Activation," *Thrombosis Research* 38:695-706, 1985.
Asaki et al., "The Effect of Oral Rinses Extracted from Japanese Tea on the Experimental Gingivitis in Man," *Journal of the Japanese Society of Periodontology* 37(2):412-421, 1995 (abstract only).
Bastianetto et al., "Neuroprotective abilities of resveratrol and other red wine constituents against nitric oxide-related toxicity in cultured hippocampal neurons," *British Journal of Pharmacology* 131:711-720, 2000.
Bosset et al., "Photoageing shows histological features of chronic skin inflammation without clinical and molecular abnormalities," *British Journal of Dermatology* 149:826-835, 2003.
Botanical Extracts: Acacia Catechu Extract, URL=http://www.exoticnatural.com/acacia-catechu.htm, date accessed Apr. 19, 2007.
Boumendjel et al., "B-ring Substituted 5,7-Dihydroxyflavonols with High-Affinity Binding to P-Glycoprotein Responsible for Cell Multidrug Resistance," *Bioorganic & Medicinal Chemistry Letters* 11:75-77, 2001.

Brideau et al., "A human whole blood assay for clinical evaluation of biochemical efficacy of cyclooxygenase inhibitors," *Inflamm. Res.* 45(2):68-74, 1996.
Butenko et al., "Anti-inflammatory properties and inhibition of leukotriene $C_4$ biosynthesis in vitro by flavonoid baicalein from *Scutellaria baicalensis* georgy roots," *Agents Actions* 39(Special Conference Issue):C49-C51, 1993.
Chen et al., "Oroxylin A Inhibition of Lipopolysaccharide-Induced iNOS and COX-2 Gene Expression via Supression of Nuclear Factor-κB Activation," *Biochemical Pharmacology* 59:1445-1457, 2000.
Chen et al., "Wogonin, baicalin, and baicalein inhibition of inducible nitric oxide synthase and cyclooxygenase-2 gene expressions induced by nitric oxide synthase inhibitors and lipopolysaccharide," *Biochemical Pharmacology* 61:1417-1427, 2001.
Chi et al., "Effect of wogonin, a plant flavone from Scutellaria radix, on the suppression of cyclooxygenase-2 and the induction of inducible nitric oxide synthase in lipopolysaccharide-treated RAW 264.7 cells," *Biochemical Pharmacology* 61:1195-1203, 2001.
Chinese Herbs Direct, URL=http://www.chineseherbsdirect.com, date accessed 2007.
Chung et al., "Pharmacological Effects of Methanolic Extract from the Root of *Scutellaria baicalensis* and its Flavonoids on Human Gingival Fibroblast," *Planta Med.* 61(2):150-153, 1995.
Commenges et al., "Intake of flavonoids and risk of dementia," *Eur. J. Epidemiol.* 16(4):357-363, 2000 (w/English abstract).
Dafallah et al., "Investigation of the anti-inflammatory activity of Acacia nilotica Hibiscus sabdariffa," *The American Journal of Chinese Medicine* 24(3-4):263-269, 1996 (abstract only).
de la Puerta et al, "Inhibition of Leukocyte Eicosanoid Generation and Radical Scavenging Activity by Gnaphalin, a Lipophilic Flavonol Isolated from *Helichrysum picardii*," *Planta Medica* 65:507-511, 1999.
de Whalley et al., "Flavonoids Inhibit the Oxidative Modification of Low Density Lipoproteins by Macrophages," *Biochemical Pharmacology* 39(11): 1743-1750, 1990.
Friedman et al., "NSAIDs in Dermatologic Therapy: Review and Preview," *J. Cutan. Me. Surg.*, pp. 449-459, 2002.
Gilani et al., "Studies on antihypertensive and antispasmodic activities of methanol extract of Acacia nilotica pods," *Phytother. Res.* 13(8):665-669, 1999 (abstract only).
Hagos et al., "Isolation of Smooth Muscle Relaxing 1,3-Diarylpropan-2-ol Derivatives from *Acacia tortilis*," *Planta Med.* 53(1):27-31, 1987.
Hanausek-Walaszek et al., "Inhibitory Effects of Triterpenoid Saponins from *Acacia Victoriae* on Dimethylbenz [A] Anthracene-Induced Murine Skin Carcinogenesis," *Proceedings of the American Association for Cancer Research* 41:663, 2000 (abstract #4216).
Haridas et al., "Avicins: Novel Triterpenoid Saponins from Acacia Victoriae (Benth) Induce Apoptosis by Mitochondrial Perturbation," *Proceedings of the American Association for Cancer Research* 41:361, 2000 (abstract #3820).
Hase et al., "Histological increase in inflammatory infiltrate in sun-exposed skin of female subjects: the possible involvement of matrix metalloproteinase-1 produced by inflammatory infiltrate on collagen degradation," *British Journal of Dermatology* 142:267-273, 2000.
Heo et al., "Anti-genotoxicity of galangin as a cancer chemopreventive agent candidate," *Mutation Research* 488:135-150, 2001.
Hong et al., "Effects of purified green and black tea polyphenols on cyclooxygenase-and lipoxygenase-dependent metabolism of arachidonic acid in human colon mucosa and colon tumor tissues," *Biochemical Pharmacology* 62:1175-1183, 2001.
Imamura et al., "Inhibitory Effects of Flavonoids on Rabbit Heart Carbonyl Reductase," *J. Biochem.* 127:653-658, 2000.
International Preliminary Examination Report dated Oct. 27, 2005, for PCTAN PCT/US2004/010279.
International Search Report mailed Sep. 10, 2004, for PCTAN PCT/04/10279.
Itoigawa et al., "Structure-activity relationship of cardiotonic flavonoids in guinea-pig papillary muscle," *Journal of Ethnopharmacology* 65:267-272, 1999.
Kalkbrenner et al., "In vitro Inhibition and Stimulation of Purified Prostaglandin Endoperoxide Synthase by Flavonoids: Structure-Activity Relationship," *Pharmacology* 44:1-12, 1992.

(56) References Cited

OTHER PUBLICATIONS

Kaneko et al., "Protective Effect of Flavonoids on Endothelial Cells against Linoleic Acid Hydroperoxide-induced Toxicity," *Biosci. Biotechnol. Biochem. 63*(2):323-328, 1999.

Kikukawa et al., "Mechanism of suppressive action of TJ114 upon murine type II collagen-induced arthritis," *Jpn. J. Inflamm. 15*:129-133, 1995 (abstract only).

Kim et al., "Pharmacological Activities of Flavonoids (I)—Relationships of Chemical Structure of Flavonoids and their Inhibitory Activity of Hypersensitivities-," *Yakhak Hoeji 34*(5):348-364, 1990.

Kimura et al., "Effects of Baicalein Isolated from *Scutellaria baicalensis* Radix on Adhesion Molecule Expression Induced by Thrombin and Thrombin Receptor Agonist Peptide in Cultured Human Umbilical Vein Endothelial Cells," *Planta Med 67*:331-334, 2001.

Krakauer et al., "The flavonoid baicalin inhibits superantigen-induced inflammatory cytokines and chemokines," *FEBS Letters 500*:52-55, 2001.

Kubo et al., "Flavonols from *Heterotheca inuloides*: Tyrosinase Inhibitory Activity and Structural Criteria," *Bioorganic & Medicinal Chemistry 8*:1749-1755, 2000.

Kubo et al., "Studies on Scutellariae Radix. VII. Anti-arthritic and Anti-inflammatory actions of Methanolic Extract and Flavonoid Components from Scutellariae Radix," *Chem. Pharm. Bull. 32*(7):2724-2729, 1984.

Kuhn et al., "Action of cyclooxygenase (COX) and lipoxygenase (LOX) inhibitors as well as of oxygen free radical scavengers (OFRS) in the inflammation-induced vasodepression," *Biomed. Biochim. Acta 47*(10-11):S320-S323, 1988.

Lee et al., "Salicylic Acid Peels for the Treatment of Acne Vulgaris in Asian Patients," *Dermatol. Surg. 29*:1196-1199, 2003.

Leyden, "Acne Vulgaris is a multifactorial disease," *J. Am. Acad. Dermatol. 49*(3 Suppl.):S199, 2003.

Li et al., "The Flavonoid baicalin exhibits anti-inflammatory activity by binding to chemokines," *Immunopharmacology 49*:295-306, 2000.

Liang et al., "Supression of inducible cyclooxygenase and nitric oxide synthase through activation of peroxisome proliferator-activated receptor-γ by flavonoids in mouse macrophages," *FEBS Letters 496*:12-18, 2001.

Meyer et al., "Antiviral activity of galangin isolated from the aerial parts of *Helichrysum aureonitens*," *Journal of Ethnopharmacology 56*:165-169, 1997.

Millikan, "The Rationale for Using a Topical Retinoid for Inflammatory Acne," *Am. J. Clin. Dermatol. 4*(2):75-80, 2003.

Min et al., "(−)-Epiafzelechin: Cyclooxygenase-1 Inhibitor and Anti-Inflammatory Agent from Aerial Parts of *Celastrus orbiculatus*," *Planta Med. 65*:460-462, 1999.

Moroney et al., "Selectivity of Neutrophil 5-Lipoxygenase and Cyclo-oxygenase Inhibiton by an Anti-inflammatory Flavonoid Glycoside and Related Aglycone Flavonoids," *J. Pharm. Pharmacol. 40*(11):787-792, 1988.

Mutoh et al., "Suppression by flavonoids of cyclooxygenase-2 promoter-dependent transcriptional activity in colon cancer cells: structure-activity relationship," *Jpn. J. Cancer Res. 91*(7):686-691, 2000 (abstract only).

Nadkarni (ed.), *Dr. K.M. Nadkarni's Indian Materia medicM: With Ayurvedic, Unani-Tibbi, Siddha, Allopathic, Homeopathic, Naturopathic & Home Remedies, Appendicces & Indexes*: vol. 1, Popular Prakashan, London, 1996, pp. 9-17.

Nakagami (Aug. 22, 1995) abstract, Database WPI Week 199519 Aug. 22, 1995, Derwent Publications Ltd., London, GB; p. 2, AN 1995-325471 XP002418722 Nakagami T; Nakamura T; Tamura N: "Anti-complementary substance used as therapeutic agent—comprises gallic acid, methyl gallate, acetyl-salicylic acid, caffeic acid, catechin, epi-gallo-catechin gallate, myricetin, quercitrin and/or baicalein, or their salts" & JP 07 223941 A ((NIHA-N) Nippon Ham KK).

Nakahata et al., "[Inhibition of mitogen-activated protein kinase cascade by baicalein, a flavonoid of natural origin]," *Nippon Yakurigaku Zasshi 114*(Suppl. 1):215P-219P, 1999 (w/English abstract).

Nakahata et al., "Analysis of inhibitory effects of scutellariae radix and baicalein on prostaglandin E2 production in rat C6 glioma cells," *Am. J. Chin. Med. 26*(3-4):311-323, 1998 (w/English abstract).

Nakajima et al., "Inhibitory Effect of Baicalein, a Flavonoid in Scutellaria Root, on Eotaxin Production by Human Dermal Fibroblasts," *Planta Med. 67*:132-135, 2001.

Nakamura et al., "Arachidonic Acid Cascade Inhibitors Modulate Phorbol Ester-Induced Oxidative Stress in Female ICR Mouse Skin: Differential Roles of 5-Lipoxygenase and Cyclooxygenase-2 in Leukocyte Infiltration and Activation," *Free Radical Biology & Medicine 35*(9):997-1007, 2003.

Noreen et al., "Development of a Radiochemical Cyclooxygenase-1 and -2 in Vitro Assay for Identification of Natural Products as Inhibitors of Prostaglandin Biosynthesis," *J. Nat. Prod. 61*:27, 1998.

Noreen et al., "Flavan-3-ols Isolated from Some Medicinal Plants Inhibiting COX-1 and COX-2 Catalysed Prostaglandin Biosynthesis," *Planta Medica 64*:520-524, 1998.

Noreen et al., "Two New Isoflavones from *Ceiba pentandra* and Their Effect on Cyclooxygenase-Catalyzed Prostaglandin Biosynthesis," *J. Nat. Prod 61*:8-12, 1998.

Office Action dated Feb. 26, 2009, for U.S. Appl. No. 11/661,382.
Office Action dated Feb. 8, 2010, for U.S. Appl. No. 11/279,925.
Office Action dated Jun. 15, 2009, for U.S. Appl. No. 11/279,925.

Park et al., "Involvement of ERK and Protein Tyrosine Phosphatase Signaling Pathways in EGCG-Induced Cyclooxygenase-2 Expression in Raw 264.7 Cells," *Biochemical and Biophysical Research Communications 286*:721-725, 2001.

Phillips et al., "Polarized light photography enhances visualization of inflammatory lesions of acne vulgaris," *J. Am. Acad. Dermatol. 37*:948-952, 1997.

Raso et al., "Inhibition of inducible nitric oxide synthase and cyclooxygenase-2 expression by flavonoids in macrophage J774A. 1," *Life Sciences 68*:921-931, 2001.

Salmon et al., "Evaluation of Inhibitors of Eicosanoid Synthesis in Leukocytes: Possible Pitfall of Using the Calcium Ionophore A23187 to Stimulate 5 Lipoxygenase," *Prostaglandins 29*(3):377-385, 1985.

Sekine et al., "Structure of Synthesis of a New Monoterpenoidal Carboxamide from the Seeds of the Thai Medicinal Plant *Acacia concinna*," *Chem. Pharm. Bull. 45*(1):148-151, 1997.

Shah et al., "The Antiplatelet Aggregatory Activity of *Acacia nilotica* is Due to Blockade of Calcium Influx through Membrane Calcium Channels," *Gen. Pharmac. 29*(2):251-255, 1997.

So et al, "Inhibition of proliferation of estrogen receptor-positive MCF-7 human breast cancer cells by flavonoids in the presence and absence of excess estrogen," *Cancer Letters 112*:127-133, 1997.

Sobottka et al., "Effect of Flavonol Derivatives on the Carrageenin-Induced Paw Edema in the Rat and Inhibition of Cyclooxygenase-1 and 5-Lipoxygenase in Vitro," *Arch. Pharm. 333*(7):205-210, 2000.

Takada (May 25, 1999) abstract, Database WPI week 199919 May 25, 1999, Derwent Publications Ltd., London, GB; p. 1, AN 1999-367373 XP002418790 Takada R: "Catechin-containing soap—includes tea-originated catechin" & JP 11 140497 A ((MYUR-N) Myure KK).

Tanaka (Jan. 8, 2003) abstract, Database WPI week 200320 Jan. 8, 2003, Publications Ltd., London, GB; p. 3, AN 2003-451711 XP002418791 Tanaka H: "Cosmetics for preventing aging of skin, comprises elastase inhibitor such as catechin, flavone, flavonols, flavanone, isoflavanones, coumarin and/or their glycosides" & JP 2003 002820 A ((NARI-N) Narisu Keshohin KK).

Tordera et al., "Influence of anti-inflammatory flavonoids on degranulation and arachidonic acid release in rat neutrophils," *Z Naturforsch [C] 49*(3-4):235-240, 1994 (abstract only).

Tsao et al., "Effect of Chinese and Western Antimicrobial Agents on Selected Oral Bacteria," *J. Dent. Res. 61*(9):1103-1106, 1982.

Wakabayashi et al., "Wogonin inhibits inducible prostaglandin $E_2$ production in macrophages," *European Journal of Pharmacology 406*:477-481, 2000.

Wang et al., "Cyclooxygenase active bioflavonoids from Balaton tart cherry and their structure activity relationships," *Phytomedicine 7*(1):15-19, 2000 (abstract only).

(56) References Cited

OTHER PUBLICATIONS

Wenzel et al., "Dietary Flavone Is a Potent Apoptosis Inducer in Human Colon Carcinoma Cells," *Cancer Research* 60:3823-3831, 2000.
Wilgus et al., "Inhibition of ultraviolet light B-induced cutaneous inflammation by a specific cyclooxygenase-2 inhibitor," *Adv. Exp. Med. Biol.* 507:85-92, 2002.
Wilgus et al., "Topical application of a selective cyclooxygenase inhibitor suppresses UVB mediated cutaneous inflammation," *Prostaglandins & other Lipid Mediators* 62:367-384, 2000.
Yamahara et al., "Inhibitory effect of crude Chinese drugs on the denaturation of human γ-globulin induced by heat and copper (2+)," *Shoyakugaku Zasshi* 35(2):103-107, 1981 (abstract only).
You et al., "Inhibition of Cyclooxygenase/Lipoxygenase from Human Platelets by Polyhydroxylated/Methoxylated Flavonoids Isolated from Medicinal Plants," *Arch. Pharm. Res.* 22(1):18-24, 1999.
Mādhavah; Vṛndamādhava;—Marathi translated by Dato vallala Borkar; Yagyeswara Gopal Dixit, Bookseller, Pune; Edn. 1922 [Time of origin 9$^{th}$ century], p. 503, Formulation ID: AB/1051, Formulation Name: Khadirodakam, 3 pages. (w/English translation).
Mohammad Akmal Khan; Qaraabaadeen Azam wa Akmal (20$^{th}$ century AD), Matba Siddiqi, Delhi / Matba Mustafai, Delhi, 1909 AD, p. 354, Formulation ID: AH5/199A, Formulation Name: Tila Fasaad-e-Laun, 2 pages (w/English translation).
Mohammad Azam Khan; Muheet-e-Azam, vol. III, (19$^{th}$ century AD), Matba Nizami, Kanpur, 1887 AD, p. 37, Formulation ID: JA7/36D, Formulation Name: Tila Bara-e- Asaraat-e-Harq, 2 pages (w/English translation).
Nityanāthasiddhah; Rasaratnākarah-Rasendra khandam Comm. Datto Vallāl Borakara, Ed. 2nd, 1986, Shri Gajānan Book Depot, (Pune), p. 756, Formulation ID: RJ/30, Formulation Name: Kusthaharalepah (02), 3 pages (w/English translation).
Qi Jia et al., "Formulation of Dual Cyclooxygenase (COX) and Lipoxygenase (LOX) Inhibitors for Mammal Skin Care," Third Party Observation dated Jul. 2, 2011, for CA Application No. 2,521,429, 23 pages.
Nishioka et al., "Baicalein, an α-Glucosidase Inhibitor from *Scutellaria baicalensis*," *J. Nat. Prod.* 61:1413-1415, 1998.
Reinhard, "Uncaria tomentosa (Willd.) D.C.: Cat's Claw, Uña de Gato, or Savéntaro," *The Journal of Alternative and Complementary Medicine* 5(2):143-151, 1999.
Steglich et al. (eds.), *ROMPP Encyclopedia: Natural Products*, Georg Thieme Verlag, Suttgart, Germany, 2000, p. 630, 3 pages.
"L17—(baicalin near20 catechin) near20 weight" Search History, retrieved Jan. 8, 2009, from http://jupiter1:42900/bin/cgi-bin/PreSearch.p1, 1 page.
"Move Free Advanced Ingredients—Uniflex," retrieved May 7, 2008, from http://www.movefreeadvanced.com/ingredients.asp?q=uniflex, 3 pages.
"Scutellaria Root / *Official Monographs for Part II*" in the Japanese Pharmacopoeia, 14th ed. (English version), Society of Japanese Pharmacopoeia, Tokyo, Japan, 2001, pp. 1042-1043, 4 pages.
Abdulrazak et al., "Chemical Composition, Phenolic Concentration and in Vitro Gas Production Characteristics of Selected Acacia Fruits and Leaves,"*Asian-Australian Journal of Animal Sciences* 13(7):935-940, 2000.
Ali Ibn-e-Abbaas Majoosi; Kaamil-al-Sena'ah, Part II (10$^{th}$ century AD), Central Council for Research in Unani Medicine, 61-65 Institutional Area, Janak Puri, New Dehli-58, 2005 AD p. 129, Formulation ID: AH3/876C, Formulation Name: Zimaad Baraae Qooba, 3 pages. (with English translation).
Arnaud, "COX-2: an in vivo evidence of its participation in heat stress-induced myocardial preconditioning," *Cardiovascular Research* 58:582-588, 2003.
Azad et al., "Isolation of (+)-catechin and a new polyphenolic compound in Bengal catechu," *Journal of Wood Science* 47(5):406-409, 2001.
Babu et al., "Aspirin and Asthma," *Chest* 118:1470-1476, 2000.
Baumann et al., "Flavonoids and Related Compounds as Inhibitors of Arachidonic Acid Peroxidation," *Prostaglandins* 20(4):627-639, Oct. 1980.
Bertolini et al., "Dual Acting Anti-Inflammatory Drugs: A Reappraisal," *Pharmacology Research* 44(6):437-450, 2001.
Bhagwat et al., "Flavanoid composition of tea: Comparison of black and green teas," 2003 IFT Annual Meeting and Food Expo, Jul. 12-16, 2003, Chicago, Illinois, 1 page (Poster).
Bhāvamiśra; Bhāvaprakāśa—Edited & translated by Brahmashankara Misra & RupaLalaji Vaisya, Part-I: Chaukhambha Sanskrit Sansthan, Varanasi, Edn. 9th, 1999, Time of origin 16th century, p. 110, Formulation ID: RS/3007D, Formulation Name: Dantakūrcikā(04), 3 pages. (with English translation).
Bickford et al., "Antioxidant-rich diets improve cerebellar physiology and motor learning in aged rats," *Brain Research* 866:211-217, Jun. 2, 2000.
Bickford et al., "Effect of Normobaric Hyperoxia on Two Indexes of Synaptic Function in Fisher 344 Rats," *Free Radical Biology & Medicine* 26(7/8):817-824, Apr. 1999.
Bickford et al., "Effects of aging on cerebellar noradrenergic function and motor learning: nutritional interventions," *Mechanisms of Ageing and Development* 111:141-154, Nov. 1999.
Boozer et al., "An herbal supplement containing Ma Huang-Guarana for weight loss: a randomized, double-blind trial," *International Journal of Obesity* 25: 316-324, 2001.
Brock et al., "Arachidonic Acid is Preferentially Metabolized by Cyclooxygenase-2 to Prostacyclin and Prostaglandin E$_2$," *Journal of Biological Chemistry* 274(17):11660-11666, Apr. 1999.
*The Combined Dictionary*, Chapman & Hall/CRC, v. 5:1, Jun. 2001.
Buckingham, *The Combined Chemical Dictionary*, Chapman & Hall CRC, v. 5:2, Dec. 2001.
Bunting et al., "The Prostacyclin-Thromboxane A$_2$ Balance: Pathophysiological and Therapeutic Implications," *British Medical Bulletin* 39(3):271-276, 1983.
Butterfield et al., "Structural and Functional Changes in Proteins Induced by Free Radical-mediated Oxidative Stress and Protective Action of the Antioxidants *N-tert*-Butyl-α-phenylnitrone and Vitamin E$^a$," *Annals of the New York Academy of Sciences* 854:448-462, Nov. 20, 1998.
Cao et al., "Hyperoxia-induced changes in antioxidant capacity and the effect of dietary antioxidants," *Journal of Applied Physiology* 86(6):1817-1822, Jun. 1999.
Cao et al., "Oxygen-Radical Absorbance Capacity Assay for Antioxidants," *Free Radical Biology & Medicine* 14:303-311, 1993.
Carney et al., "Reversal of age-related increase in brain protein oxidation, decrease in enzyme activity, and loss in temporal and spatial memory by chronic administration of the spin-trapping compound *N-tert*-butyl-α-phenylnitrone," *Proceedings of the National Academy of Sciences USA* 88:3633-3636, May 1991.
Carson et al., "The cellular response in neuroinflammation: The role of leukocytes, microglia and astrocytes in neuronal death and survival," *Clinical Neuroscience Research* 6(5):237-245, Dec. 2006.
Cartford et al., "Eighteen-Month-Old Fischer 344 Rats Fed a Spinach-Enriched Diet Show Improved Delay Classical Eyeblink Conditioning and Reduced Expression of Tumor Necrosis Factor α (TNFα) and TNFβ in the Cerebellum," *Journal of Neuroscience* 22(14):5813-5816, Jul. 15, 2002.
Caughey et al., "Roles of Cyclooxygenase (COX)-1 and COX-2 in Prostanoid Production by Human Endothelial Cells: Selective Up-Regulation of Prostacyclin Synthesis by COX-2," *Journal of Immunology* 167:2831-2837, 2001.
Celotti et al., "Anti-Inflammatory Drugs: New Multitarget Compounds to Face an Old Problem. The Dual Inhibition Concept," *Pharmacological Research* 43(5):429-436, May 2001.
Chang et al., "Prevention of Lens Protein-Induced Ocular Inflammation with Cyclooxygenase and Lipoxygenase Inhibitors," *Journal of Ocular Pharmacology* 5(4):353-360, 1989.
Chang et al., "Role of 5-Lipoxygenase Products of Arachidonic Acid in Cell-to-Cell Interaction Between Macrophages and Natural Killer Cells in Rat Spleen," *Journal of Leukocyte Biology* 50:273-278, 1991.

(56) References Cited

OTHER PUBLICATIONS

Chou et al., "The Antiinflammatory and Analgesic Effects of Baicalin in Carrageenan-Evoked Thermal Hyperalgesia," *Anesthesia & Analgesia* 97:1724-1729, 2003.

Christie et al., "Opioids, NSAIDs and 5-lipoxygenase inhibitors act synergistically in brain via arachidonic acid metabolism," *Inflammation Research* 48:1-4, 1999.

Clark et al., "Do Some Inhibitors of COX-2 Increase the Risk of Thromboembolic Events?," *Drug Safety* 27(7):427-456, 2004.

Dannhardt et al., "Cyclooxygenase inhibitors—current status and future prospects," *European Journal of Medicinal Chemistry* 36(2):109-126, Feb. 2001.

Davies et al., "COX-2 selective inhibitors cardiac toxicity: getting to the heart of the matter," *Journal of Pharmacy and Pharmaceutical Sciences* 7(3):332-336, 2004.

de Gaetano et al., "Prevention of thrombosis and vascular inflammation: benefits and limitations of selective or combined COX-1, COX-2 and 5-LOX inhibitors," *TRENDS in Pharmacology Sciences* 24(5):245-252, May 2003.

Dempke et al., "Cyclooxygenase-2: a novel target for cancer chemotherapy?," *Journal of Cancer Research and Clinical Oncology* 27(7):411-417, Jul. 2001.

Deray, "Renal and cardiovascular effects of non-steroidal anti-inflammatories and selective cox 2 inhibitors," *La Presse Médicale* 33(7):483-489, Apr. 2004. (with English abstract).

Deshpande et al., "Flavonoids of *Acacia catechu* Heartwood," *Indian Journal of Chemistry* 20B:628, Jul. 1981.

DeLange et al., "Phycoerythrin Fluorescence-Based Assay for Peroxy Radicals: A Screen for Biologically Relevant Protective Agents," *Analytical Biochemistry* 177:300-306, 1989.

DeWitt, "Cox-2-Selective Inhibitors: The New Super Aspirins," *Molecular Pharmacology* 55:625-631, 1999.

Elattar et al., "Hydoxy fatty acids and prostaglandin formation in diseased human periodontal pocket tissue," *Journal of Periodontal Research* 21:169-176, 1986.

*Encyclopedia of Chinese Traditional Medicine*, ShangHai Science and Technology Press, ShanHai, China, 1998.

Engler et al., "The vasculoprotective effects of flavonoid-rich cocoa and chocolate," *Nutrition Research* 24:695-706, 2004.

Exotic Naturals, "Acacia Catechu Extract," retrieved Apr. 19, 2007 from http://www.exoticnatural.com/acacia-catechu.htm, 2 pages.

Felson, "Osteoarthritis of the Knee," *New England Journal of Medicine* 354(8):841-848, Feb. 23, 2006.

Fenton et al., "Characterization of the Effects of Antiangiogenic Agents on Tumor Pathophysiology, "*American Journal of Clinical Oncology (CCT)* 24(5):453-457, 2001.

Fiorucci et al., "Dual inhibitors of cyclooxygenase and 5-lipoxygenase. A new avenue in anti-flammatory therapy?," *Biochemical Pharmacology* 62:1433-1438, 2001.

Fogh et al., "Modulation of Eicosanoid Formation by Lesional Skin of Psoriasis: an Ex vivo Skin Model," *Acta Dermato-Venereologia* (Stockholm) 73:191-193, 1993.

Fosslien, "Review: Cardiovascular Complications of Non-Steroidal Anti-Inflammatory Drugs," *Annals of Clinical & Laboratory Science* 35(4):347-385, 2005.

Gabrielska et al., "Antioxidant Activity of Flavones from *Scutellaria baicalensis* in Lecithin Liposomes," *Verlag der Zeitschrift für Naturforschung* 52c(11-12):817-823, 1997, 8 pages.

Gaffar et al., "The effect of triclosan on mediators of gingival inflammation," *Journal of Clinical Periodontology* 22:480-484, 1995.

Gafner et al., "Evaluation of the anti-inflammatory properties of skullcap (*Scutellaria lateriflora* L.) extracts in different in vitro models," 2004 International Congress on Natural Products Research, Phoenix, Arizona, Jul. 31-Aug. 4, 2004, p. 60 and poster, 3 pages.

Gemma et al., "Diets Enriched in Foods with High Antioxidant Activity Reverse Age-Induced Decreases in Cerebellar β-Adrenergic Function and Increases in Proinflammatory Cytokines," *Journal of Neuroscience* 22(4):6114-6120, Jul. 15, 2002.

Genco et al., in *Contemporary Periodontics*, The C.V. Mosby Company, St. Louis, pp. 361-370, 1990, 12 pages.

Gilroy et al., "Inducible cyclooxygenase may have anti-inflammatory properties," *Nature Medicine* 5(6):698-701, Jun. 1999.

Giovannucci et al., "Aspirin and the Risk of Colorectal Cancer in Women," *New England Journal of Medicine* 333(10):609-614, Sep. 7, 1995.

Goebel et al., "Procainamide, a Drug Causing Lupus, Induces Prostaglandin H Synthase-2 and Formation of T Cell-Sensitizing Drug Metabolites in Mouse Macrophages," *Chemical Research in Toxicology* 12(6):488-500, 1999.

Gök et al., "Role of Leukotrienes on Coronary Vasoconstriction in Isolated Hearts of Arthritic Rats: Effect of in vivo Treatment with CI-986, a Dual Inhibitor of Cyclooxygenase and Lipoxygenase," *Pharmacology* 60:41-46, 2000.

Gould et al., "Antioxidant protection of cerebellar β-adrenergic receptor function in aged F344 rats," *Neuroscience Letters* 250:165-168, Jul. 10, 1998.

Greenspan et al., "Carboxy-Substituted Cinnamides: A Novel Series of Potent, Orally Active $LTB_4$ Receptor Antagonists,"*Journal of Medicinal Chemistry* 42(1):164-172, 1999.

Gupta, V.K., Senior Advisor and Director, TKDL, Third Party Observations dated Oct. 9, 2010, in Canadian Application No. 02584124, 7 pages.

Gupta, "Flavonoids Composition for Treating Oral Disease," Third Party Observation dated May 30, 2011, for European Application No. 05810437.3, 7 pages.

Gupta, "Formulation of Dual Cyclooxygenase (COX) and Lipoxygenase (LOX) Inhibitors for Mammal Skin Care," Third Party Observation dated Jul. 2, 2011, for Canadian Application No. 2,521,429, 8 pages.

Hamazaki et al., "Catechin's activity of inhibiting LTC4 production," *Allergy* 49(9/10):914, 2000, 2 pages. (with English translation).

Harrington et al., "Antithrombotic Therapy for Coronary Artery Disease: The Seventh ACCP Conference on Antithrombotic and Thrombolytic Therapy," *Chest* 126(3 Suppl):513S-548S, Sep. 2004.

Hase et al., "Peroxisome proliferator activated receptor (PPAR) dependent gene transcription activators," WPI/Thomson, Accession No. 2002-388616 [42], Mar. 19, 2002, 1 page.

Hennekens, "Update on Aspirin in the Treatment and Prevention of Cardiovascular Disease," *American Journal of Managed Care* 8(22 Suppl):S691-S700, Dec. 2002.

Heo et al., "Potent Inhibitory Effect of Flavonoids in *Scutellaria baicalensis* on Amyloid β Protein-Induced Neurotoxicity," *Journal of Agricultural and Food Chemistry* 52(13):4128-4132, Jun. 30, 2004. (Abstract only).

Herschman, "Regulation of prostaglandin synthase-1 and prostaglandin synthase-2," *Cancer and Metastasis Reviews* 13(3-4):241-256, Dec. 1994.

Hiipakka et al., "Structure-activity relationships for inhibition human 5α-reductases by polyphenols," *Biochemical Pharmacology* 63:1165-1176, 2002.

Hiraoka, "Long-Term Efficacy of COX-2 Selective Inhibitor Etadolac (Hypen®) on Chronic Low Back Pain and/or Osteoarthritis," *Clinical Medicine* 16(7):1037(107)-1045(115), Jul. 2000, 18 pages. (with English translation).

Ho et al., "Neuronal cyclooxygenase 2 expression in the hippocampal formation as a function of the clinical progression of Alzheimer disease," *Archives of Neurology* 58:487-492, Mar. 2001.

Hukkeri et al., "Anti-Inflammatory Activity of Leaves of *Acacia farnesiana* Willd," *Indian Drugs* 39(12): 664-666, Dec. 1, 2002.

Itou et al., "Compsns. Acting on dental caries and periodontosis—contain polyphenol cpds. pref. obtd. from tea by extn. with water," WPI/Thomson Database, Accession No. 1989-147372 [20], 1989, 1 page.

Jaeckel et al., "Correlation of Expression of Cyclooxygenase-2, Vascular Endothelial Growth Factor, and Peroxisome Proliferator-Activated Receptor δ With Head and Neck Squamous Cell Carcinoma," *Archives of Otolaryngology—Head & Neck Surgery* 127(10):1253-1259, Oct. 2001.

Jüni et al., "Risk of cardiovascular events and rofecoxib: cumulative meta-analysis," *Lancet* 364:2021-2029, Dec. 2004.

(56) References Cited

OTHER PUBLICATIONS

Kakegawa et al., "Inhibitory Effects of Tannins on Hyaluronidase Activation and on the Degranulation from Rat Mesentery Mast Cells," *Chemical and Pharmaceutical Bulletin* 33(11): 5079-5082, 1985.

Kalkbrenner et al., "In vitro Inhibition and Stimulation of Purified Prostaglandin Endoperoxide Synthase by Flavonoids: Structure-Activity Relationship," *Pharmacology* 44(1):1-12, 1992.

Kao et al., "Modulation of Endocrine Systems and Food Intake by Green Tea Epigallocatechin Gallate,"*Endocrinology* 141(3):980-987, 2000.

Kawasaki et al., "In Vitro Antiallergic Activity of Flavonoids in Histamine Release Assay Using Rat Basophilic Leukemia (RBL-2H3) Cells," *Journal of the Food Hygienic Society of Japan* 33(5): 497-503, Oct. 1994.

Khanna et al., "Natural products as a gold mine for arthritis treatment," *Current Opinion in Pharmacology* 7:344-351, 2007.

Kirchner et al., "Effects of tepoxalin, a dual inhibitor of cyclooxygenase/5-lipoxygenase, on events associated with NSAID-induced gastrointestinal inflammation," *Prostaglandins, Leukotrienes and Essential Fatty Acids* 56(6):417-423, Jun. 1997.

Kirschenbaum et al., "The role of Cyclooxygenase-2 in Prostate Cancer," *Urology* 58(Suppl 2A):127-131, Aug. 2001.

Klickstein et al., "Lipoxygenation of Arachidonic Acid as a Source of Polymorphonuclear Leukocyte Chemotactic Factors in Synovial Fluid and Tissue in Rheumatoid Arthritis and Spondyloarthritis," *Journal of Clinical Investigation* 66(5):1166-1170, Nov. 1980.

Koga et al., "Effect of plasma metabolites of (+)-catechin and quercetin on monocyte adhesion to human aortic andothelial cells," *American Journal of Clinical Nutrition* 73:941-948, 2001.

Kong, "Aspirin in Cardiovascular Disorders—What is Optimum Dose?," *American Journal of Cardiovascular Drugs* 4(3):151-158, 2004.

Kubo et al., "Studies on Scutellariae Radix, Part II: The Antibacterial Substance," *Planta Medica* 43:194-201, 1981, 9 pages.

Kulkarni et al., "Licofelone—A Novel Analgesic and Anti-Inflammatory Agent," *Current Topics in Medicinal Chemistry* 7(3):251-263, 2007.

Kuppusamy et al., "Potentiation of β-Adrenoceptor Agonist-Mediated Lipolysis by Quercetin and Fisetin in Isolated Rat Adipocytes," *Biochemical Pharmacology* 47(3):521-529, 1994.

Kuppusamy et al., "Effects of Flavonoids on Cyclic Amp Phosphodiesterase and Lipid Mobilization in Rat Adipocytes," *Biochemical Pharmacology* 44(7):1307-1315, 1992.

Lamarque, "Safety of the selective inhibitors the inducible cyclooxygenase-2 taken for long period," *Bulletin du Cancer* 91:S117-S124, 2004.

Laughton et al., "Inhibition of Mammalian 5-Lipoxygenase and Cyclo-Oxygenase by Flavonoids and Phenolic Dietary Additives," *Biochemical Pharmacology* 42(9): 1673-1681, 1991.

Lee et al., "Antitumor Agents. 49.1 Tricin,Kaempferol-3-0-β-D-Glucopyranoside and (+)-Nortrachelogenin, Antileukemic Principles from Wikstroemia indica," *Journal of Natural Products* 44:530-535, Sep.-Oct. 1981.

Lee et al., "Inhibition of oxidative DNA damage, 8-OHdG, and carbonyl contents in smokers treated with antioxidants (vitamin E, vitamin C, β-carotene and red ginseng)," *Cancer Letters* 132:219-227, 1998.

Lee et al., "Pharmacokinetics of Tea Catechins after Ingestion of Green Tea and (—)-Epigallocatechin-3-gallate by Humans: Formation of Different Metabolites and Individual Variability," *Cancer Epidemiology, Biomarkers & Prevention* 11:1025-1032, Oct. 2002.

Lenton et al., "Ability of human plasma to protect against ionising radiation is inversely correlated with age," *Mechanisms of Ageing and Development* 107:15-20, Feb. 1, 1999.

Levy et al., "Safety and efficacy of flavocoxid compared with naproxen in subjects with osteoarthritis of the knee: a pilot study," *ICRS 2007*, 5 pages.

Leyden, "A review of the use of combination therapies for the treatment of acne vulgaris," *Journal of the American Academy of Dermatology* 49(3 Suppl):S200-S210, 2003, 1 page. (English abstract only).

Li et al., "The effect of Redix Scutellariae on butyrate of Porphyromonas endodantalis in vitro," *West China Journal of Stomatology* 22(1):57-61, 2004, 1 page. (English abstract only).

Li et al., "Chemoprevention of 7,12-dimethylbenz[α]anthracene (DMBA)-induced oral carcinogenesis in hamster cheek pouch by a cyclooxygenase 2 inhibitor (Celecoxib) and a 5-lipoxygenase inhibitor (Zileuton)," *AACR Meeting Abstracts*, Abstract No. 546-a, 2004, 2 pages.

Liao et al., "Selective Inhibition of Steroid 5α-Reductase Isozymes by Tea Epicatechin-3-Gallate and Epigallaocatechin-3-Gallate," *Biochemical and Biophysical Research Communications* 214(3):833-838, 1995.

Lotioncrafter.com, "PEG-7 Glyceryl Cocoate," retrieved Apr. 17, 2008, from http://www.lotioncrafter.com/store/PEG-7-Glyceryl-Cocoate-pr-16444.html, 1 page.

Lubrizol, Material Safety Data Sheet: CARBOPOL* ULTREZ 21 Polymer, effective date Oct. 17, 2007, 8 pages.

Lynch, "Age-Related Impairment in Long-Term Potentiation in Hippocampus: A Role for the Cytokine, Interleukin-1β?," *Progress in Neurobiology* 56:571-589, Dec. 1998.

Matsumoto et al., "Concordant Induction of Prostaglandin $E_2$ Synthase with Cyclooxygenase-2 Leads to Preferred Production of Prostaglandin $E_2$ over Thromboxane and Prostaglandin $D_2$ in Lipopolysaccharide-Stimulated Rat Peritoneal Macrophages," *Biochemical and Biophysical Research Communications* 230(1):110-114, 1997.

Mayo Clinic, "Alzheimer's disease," Feb. 10, 2009, 2 pages.

McAdam et al., "Systemic biosynthesis of prostacyclin by cyclooxygenase (COX)-2: The human pharmacology of a selective inhibitor of COX-2," *Proceedings of the National Academy of Sciences USA* 96:272-277, Jan. 1999.

MedicineNet.com, "Rheumatoid Arthritis (RA)," retrieved from www.medicinenet.com/rheumatoid_arthritis/article.htm, Jun. 4, 2009, 4 pages.

Miyamoto et al., "Studies on selection method of crude drugs by statistical analysis. Research on Rhubarb having anti-inflammatory activity," *Natural Medicines* 55(4): 159-164, 2001. (with English abstract).

Mohammad Akmal Khan, Qaraabaadeen Azam wa Akmal (20$^{th}$ century AD), Matba Siddiqi, Delhi/Matba Mustafai, Delhi, 1909 AD p. 173, Formulation ID: BA3/1032, Formulation Name: Nuskha Sanoon, 3 pages. (with English translation).

Mohammad Akmal Khan, Qaraabaadeen Azam wa Akmal (20$^{th}$ century AD), Matba Siddiqi, Delhi/Matba Mustafai, Delhi, 1909 AD p. 410, Formulation ID: AH5/610, Formulation Name: Sanoon Bara-e-Zirs, 3 pages. (with English translation).

Mohammad Najmul Ghani Khan; Qaraabaadeen Najm-al-Ghani (20$^{th}$ century AD), Munshi Nawal Kishore, Lucknow, (Second Edition), 1928 AD p. 667, Formulation ID: NA4/4357, Formulation Name: Raughan, 4 pages. (with English translation).

Montine et al., "Antioxidants significantly affect the formation of different classes of isoprostanes and neuroprostanes in rat cerebral synaptosomes," *Biochemical Pharmacology* 65(4):611-617, Feb. 15, 2003.

Moore et al., "COX-2 Inhibition, Apoptosis, and Chemoprevention by Nonsteroidal Anti-inflammatory Drugs," *Current Medicinal Chemistry* 7(11):1131-1144, 2000.

Moore, *Prostanoids: pharmacololgical, physiological and clinical relevance.* Cambridge University Press, N.Y., 229-230, 1985.

Morimoto et al., "*Effects of Bofu-tsusho-san*, a traditional Chinese medicine on body fat accumulation in fructose-loaded rats," *Folia Pharmacologica Japonica* (*Nippon Yakurigaky Zasshi*) 117: 77-86, 2001. (with English abstract).

Murari et al., "A Study of the Components of Cutch: Isolation of Catechin, Gallocatechin, Dicatechin & Catechin Tetramer as Methyl Ethers," *Indian Journal of Chemistry* 14B(9):661-664, 1976.

Murase et al., "Beneficial effects of tea catechins on diet-induced obesity: stimulation of lipid catabolism in the liver," *International Journal of Obesity* 26: 1459-1464, 2002.

(56) References Cited

OTHER PUBLICATIONS

Murray et al., "Dietary Supplementation with Vitamin E Reverses the Age-related deficit in Long Term Potentiation in Dentate Gyrus," *Journal of Biological Chemistry* 273(20):12161-12168, May 15, 1998.
Nadkarni, ed., Dr. K.M. Nadkarni's *Indian Materia Medica: With Ayurvedic, Unani-Tibbi, Siddha, Allopathic, Homeopathic, Naturopathic & Home Remedies, Appendices & Indexes*: vol. 1, Popular Prakashan, Bombay, 1996, pp. 8-17, 7 pages.
Nagai et al., "Inhibition of Mouse Liver Sialidase by the Root of *Scutellaria baicalensis*," *Planta Medica* 55:27-29, 1989, 4 pages.
Nakagami et al., "Anti-complementary substance used as therapeutic agent—comprises gallic acid, methyl gallate, acetyl-salicylic acid, caffeic acid, catechin, epi-galla-catechin gallate, myricetin, quercitrin and/or baicalein, or their salts," WPI/Thomson Database, Accession No. 1995-325471 [42], Feb. 14, 1994, 1 page.
Niwa et al., "Application of New Drugs to the Elderly (12)—COX-2 Selective Inhibitor," *Geriatric Gastroenterology* 10(3):181-184, 1998, 9 pages. (with English translation).
Nutracon 2008 NutriAward, retrieved May 1, 2008, from http://www.nutraconference.com/nutraward.index.cfm, 2 pages.
Oringer, "Modulation of the Host Response in Periodontal Therapy," *Journal of Periodontology* 73(4):460-470, Apr. 2002.
Otani et al., "Histo-chemical Studies on the Anti-ulcer Effect of Bamboo Grass in Rats," *International Journal of Tissue Reactions* XII(6):319-332, 1990.
Parente, "Pros and Cons of Selective Inhibition of Cyclooxygenase-2 versus Dual Lipoxygenase/Cyclooxygenase Inhibition: Is Two Better than One?," *Journal of Rheumatology* 28:2375-2382, Nov. 2001, 22 pages.
Patrono et al., "Drug Therapy: Low-Dose Aspirin for the Prevention of Atherothrombosis," *New England Journal of Medicine* 353(22):2373-2386, Dec. 2005.
Patrono et al., "Functional Significance of Renal Prostacyclin and Thromboxane $A_2$ Production in Patients with Systemic Lupus Erythematosus," *Journal of Clinical Investigation* 76:1011-1018, 1985.
Pelletier et al., "Therapeutic role of dual inhibitors of 5-LOX and COX, selective and non-selective non-steroidal anti-inflammatory drugs," *Annals of the Rheumatic Diseases* 62:501-509, 2003.
Rae et al., "Leukotriene $B_4$, An Inflammatory Mediator in Gout," *Lancet* 320(8308):1122-1124, Nov. 1982.
Rainsford, "The ever-emerging anti-inflammatories. Have there been any real advances?," *Journal of Physiology—Paris* 95:11-19, 2001.
Ramesiiwaii et al., "Chemical Constituents of Acacia," 1997.
Raz et al., "Differential modification of cyclo-oxygenase and peroxidase activities of prostaglandin endoperoxidase synthase by proteolytic digestion and hydroperoxides," *Biochemical Journal* 269(3):603-607, 1990.
Raz et al., "Regulation of Fibroblast Cyclooxygenase Synthesis by Interleukin-1," *Journal of Biological Chemistry* 263(6):3022-3028, Feb. 25, 1988.
Rioja et al., "An anti-inflammatory ditriazine inhibiting leukocyte functions and expression of inducible nitric oxide synthase and cyclo-oxygenase-2," *European Journal of Pharmacology* 397(1):207-217, May 2000.
Rocca et al., "Cyclooxygenase-2 expression is induced during human megakaryopoiesis and characterizes newly formed platelets," *Proceedings of the National Academy of Sciences USA* 99(11):7634-7639, May 2002.
Saleem et al., "Chemistry of the Medicinal Plants of Genus *Acacia*," *Hamdard Medicus* 41(1):63-67, 1998.
Sartor et al., "Inhibition of matrix-proteases by polyphenols: chemical insights for anti-inflammatory and anti-invasion drug design," *Biochemical Pharmacology* 64:229-237, 2002.
Sharma, "Chemical Constituents of *Acacia catechu* Leaves," *Journal of Indian Chemical Society* 74:60, Jan. 1997.
Sharon et al., "Production of Leukotrienes by Colonic Mucosa from Patients with Inflammatory Bowel Disease (IBD)," *Gastroenterology* 84(5, Part 2):1306, 1983.
Shen, "Inhibition of thrombin: relevance to anti-thrombosis strategy," *Frontiers in Bioscience* 11:113-120, Jan. 2006.
Shibata et al., "Pharmacological Study of Kumazasa (Report 1) Acute toxicity, anti-inflammatory and antiulcerative effects of kumazasa water soluble fraction (Folin)," *Folia Pharmacologica Japonica* 71(5):481-490, 1975, 11 pages. (with English translation).
Smalley et al., "Use of Nonsteroidal Anti-inflammatory Drugs and Incidence of Colorectal Cancer," *Archives of Internal Medicine* 159(2):161-166, Jan. 25, 1999.
SmartSkinCare.com, "What green tea can and cannot do for your skin," retrieved Jun. 5, 2009, from http://www.smartskincare.com/treatments/topical/greentea.html, 3 pages.
Sodhala; Gadanigrahah ed, Ganga Sahayah Pandeya & Com., Indradeva Tripathi, Part-1(Prayoga Khanda) Chaukhamba Sanskrit Sansthan, Varanasi, Ed. $3^{rd}$ 1999, p. 107-108, Formulation ID: AK2/158, Formulation Name: Khadiradyam Tailam, 6 pages. (with English translation).
Sodhala; Gadanigrahah ed, Ganga Sahayah Pandeya & Com., Indradeva Tripathi, Part-3(Salakya-Pancakarma Khanda) Chaukhamba Sanskrit Sansthan(Varanasi) Ed. $3^{rd}$ 1999, p. 225, Formulation ID: RG2/525, Formulation Name: Dantasula Cikitsa, 3 pages. (with English translation).
Stadtman et al., "Reactive Oxygen-Mediated Protein Oxidation in Aging and Disease," *Drug Metabolism Reviews* 30:225-243, May 1998.
Stanke-Labesque et al., "Angiotensin II-induced contractions in human internal mammary artery: effects of cyclooxygenase and lipoxygenase inhibition," *Cardiovascular Research* 47:376-383, 2000.
Sugiyama, "The roots of Cha and Gambir," *Yakushigaku Zasshi* 40(2):98-106, 2005, 2 pages. (English abstract only).
Szekanecz et al., "Temporal expression of cytokines and chemokines in rat adjuvant-induced arthritis," from *Abstracts of the $21^{st}$ European Workshop for Rheumatology Research*, in *Arthritis Research* 3:A1-A47, Abstract p. 24, 2001, 47 pages.
Vāgbhata; Astānga Samgraha—(commentary by Indu), Part-I(KA); Central Council for Research in Ayurveda & Siddha, New Delhi, 1991, Time of origin 5-$10^{th}$ century, p. 27, Formulation ID: AT/2103, Formulation Name: Gandūsadhāranādigunaāh, 3 pages. (with English translation).
Vautrin, "Etude botanique chimique et pharmacaologique du genre *Acacia*. (Botanical, chemical and pharmacological study of the *Acacia* species).," Université de Dijon (France), 94pp., 1996, Abstract #58/646c in *Dissertation Abstracts International* 58(1):177-C, 1997, 3 pages.
Verheugt, "New anticoagulants in ischemic heart disease," *La Presse Médicale* 34:1325-1329, Oct. 2005.
Wakdikar, "Global health care challenge: Indian experiences and new prescriptions," *Electronic Journal of Biotechnology* 7(3):217-223, Dec. 15, 2004.
Wallace et al., "Limited anti-inflammatory efficacy of cyclooxygenase-2 inhibition in carrageenan-airpouch inflammation," *British Journal of Pharmacology* 126:1200-1204, 1999.
Weinberg, "Nitric Oxide Synthase 2 and Cyclooxygenase 2 Interactions in Inflammation," *Immunologic Research* 22(2-3):319-341, 2000.
Whelton et al., "Cyclooxygenase-2 Specific Inhibitors and Cardiorenal Function: A Randomized, Controlled Trial of Celecoxib and Rofecoxib in Older Hypertensive Osteoarthritis Patients," *American Journal of Therapeutics* 85:85-95, 2001.
Whelton et al., "Nonsteroidal Anti-Inflammatory Drugs: Effects on Kidney Function," *Journal of Clinical Pharmacology* 31:588-598, 1991.
Whiteman et al., "Protection Against Peroxynitrite-Dependent Tyrosine Nitration and $\alpha_1$-Antiproteinase Inactivation by Ascorbic Acid. A Comparison with Other Biological Antioxidants," *Free Radical Research* 25(3):275-283, Sep. 1996.
Wikipedia, "Cyclooxygenase," retrieved Sep. 30, 2009, 5 pages.
Wikipedia, "Lipid peroxidation," retrieved Sep. 30, 2009, 2 pages.
Wikipedia, "Peroxidase," retrieved Sep. 30, 2009, 2 pages.
Winter, "Unigen's Univestin targets joint inflammation," *Functional Foods & Nutraceuticals* May 2005, p. 14.

(56) References Cited

OTHER PUBLICATIONS

Wollheim, "Approaches to rheumatoid arthritis in 2000," *Current Opinion in Rheumatology* 13(3):193-201, 2001.

Xiaozhen et al., "Induction of $PGE_2$ Production and COX-2 Expression in Human Gingival Fibroblasts Stimulated with LPS," *Medical Journal of Wuhan University* 23(4):301-305, Oct. 2002. (with English abstract).

Xie et al., "Mitogen-Inducible Prostaglandin G/H Synthase: A New Target for Nonsteroidal Antiinflammatory Drugs," *Drug Development Research* 25(4):249-265, 1992.

Xu et al., "[Stduy on flavonoids in *Ligustrum lucidum*]," *Zhong Yao Cai* 30(5):538-540, May 2007, 1 page. (English abstract only).

Yang et al., "Effects of Green Tea Catechin on Phospholipase $A_2$ Activity and Antithrombus in Streptozotocin Diabetic Rats," *Journal of Nutritional Science and Vitaminology* 45:337-346, Jun. 1999.

Ye et al., "Anticancer Activity of *Sculletaria baicalensis* and Its Potential Mechanism," *Journal of Alternative & Complementary Medicine* 8(5):567-572, Nov. 5, 2002.

Yoshida et al., "Thermogenic, anti-obesity effects of *bofu-tsusho-san* in MSG-obese mice," *International Journal of Obesity* 19:717-722, 1995.

Yoshimura et al., "Vitamin E Prevents Increase in Oxidative Damage to Lipids and DNA in Liver of ODS Rats Given Total Body X-ray Irradiation," *Free Radical Research* 36(1):107-112, Jan. 2002.

Young et al., "The Mouse Ear Inflammatory Response to Topical Arachidonic Acid," *Journal of Investigative Dermatology* 82(4):367-371, 1984.

Zhang et al., *China Journal of the Chinese Materia Medical* 27(4):254-257, 2002, 5 pages. (with English translation).

Zhang et al., "Inhibition of Cancer Cell Proliferation and Prostaglandin $E_2$ Synthesis by *Scutellaria baicalensis*," *Cancer Research* 63:4037-4043, Jul. 15, 2003.

Kaiyadeva, Kaiyadevanighantau—(Pathyāpthyavibodhakah), [1st] Ed., P.V. Sharma and G.P. Sharma, Eds., p. 153, Chaukhambha Orientalia, Varanasi, India, 1979. (8 pages) (with English Translation).

Khan, Mohammad Azam, Ikseer Azam, vol. IV (19th Century AD), p. 309, Matba Nizami, Kanpur India, 1872. (7 pages).

Suśruta, Suśruta Samhitā (commentary by Dalhanna), vol. II, 1st Ed., P.V. Sharma, Ed., pp. 461-462, Chaukhambha Visvabharati, Varanasi, India, 2000. (9 pages) (with English Translation).

Vāgbhata, Astānga Hrdaya (commentaries by Arunadatta and Hemēdri), 8th Ed., B. H. P. Vaidya, Ed., p. 715, Chaukhambha Orientalia, Varanasi, India, 1998. (9 pages) (with English translation).

\* cited by examiner

FORMULATION OF DUAL CYCLOXYGENASE (COX) AND LIPOXYGENASE (LOX) INHIBITORS FOR MAMMAL SKIN CARE

FIELD OF THE INVENTION

This invention relates generally to a method for the prevention and treatment of diseases and conditions mediated by cyclooxygenase (COX) and lipoxygenase (LOX). Specifically, the present invention relates to a novel composition of matter comprised of a mixture of a blend of two specific classes of compounds—Free-B-Ring flavonoids and flavans—for use in the prevention and treatment of diseases and conditions of the skin mediated by the COX and LOX pathways. Included in the present invention is a method for the prevention and treatment of COX and LOX mediated diseases and conditions, including but not limited to sun burns, thermal burns, acne, topical wounds, minor inflammatory conditions caused by fungal, microbial and viral infections, vitilago, systemic lupus erythromatosus, psoriasis, carcinoma, melanoma, as well as other mammal skin cancers, skin damage resulting from exposure to ultraviolet (UV) radiation, chemicals, heat, wind and dry environments, wrinkles, saggy skin, lines and dark circles around the eyes, dermatitis and other allergy related conditions of the skin. Use of the composition described herein also affords the benefit of smooth and youthful skin with improved elasticity, reduced and delayed aging, enhanced youthful appearance and texture, and increased flexibility, firmness, smoothness and suppleness.

BACKGROUND OF THE INVENTION

Sunlight has a significant effect on the skin causing premature aging, skin cancer and a host of other skin changes such as erythema and tanning. The majority of the damage caused by sunlight is attributed to ultraviolet (UV) radiation, which has a wavelength from 200 nm to 400 nm. Ultraviolet radiation is divided into three categories, UVA, UVB or UVC, depending on wavelength. UVA, which has a wavelength range from 320-400 nm, can cause tanning and mild sunburn. UVB, which has a wavelength range from 290-320 nm, can cause sunburn and stimulate pigmentation. UVC, which has a wavelength range from 100-290 nm, can cause damage but not tanning. Exposure of the skin to UV radiation induces biphasic reactions. Thus, upon initial exposure an immediate erythema reaction occurs, which is a weak reaction that fades within 30 minutes. A delayed erythema reaction occurs after 2-5 hours of exposure and peaks around 10-24 hours. Enhanced prostaglandin and leukotriene production are the major mechanisms of action for UV, sun and chemical/thermal caused erythema. (Wang (2002) Adv. Dermatol. 18:247).

The liberation and metabolism of arachidonic acid (AA) from the cell membrane results in the generation of proinflammatory metabolites by several different pathways. Arguably, two of the most important pathways to inflammation are mediated by the enzymes lipoxygenase (LOX) and cyclooxygenase (COX). These are parallel pathways that result in the generation of leukotrienes and prostaglandins, respectively, which play important roles in the initiation and progression of the inflammatory response. These vasoactive compounds are chemotaxins, which both promote infiltration of inflammatory cells into tissues and serve to prolong the inflammatory response. Consequently, the enzymes responsible for generating these mediators of inflammation have become the targets in the current invention to develop topically administered therapeutic agents aimed at the dual inhibition of inflammation resulting from both pathways which contribute to the physiological and pathological processes of diseases and conditions such as sun burn, thermal burns, scald, acne, topical wounds, lupus erythromatosus, psoriasis, carcinoma, melanoma, and other mammalian skin cancers.

Inhibition of the COX enzyme is the mechanism of action attributed to most non-steroidal anti-inflammatory drugs (NSAIDS). There are two distinct isoforms of the COX enzyme (COX-1 and COX-2), which share approximately 60% sequence homology, but differ in expression profiles and function. COX-1 is a constitutive form of the enzyme that has been linked to the production of physiologically important prostaglandins, which help regulate normal physiological functions, such as platelet aggregation, protection of cell function in the stomach and maintenance of normal kidney function. (Dannhardt and Kiefer (2001) Eur. J. Med. Chem. 36:109-26). The second isoform, COX-2, is a form of the enzyme that is inducible by pro-inflammatory cytokines, such as interleukin-1β (IL-1β) and other growth factors. (Herschmann (1994) Cancer Metastasis Rev. 134:241-56; Xie et al. (1992) Drugs Dev. Res. 25:249-65). This isoform catalyzes the production of prostaglandin $E_2$ (PGE2) from arachidonic acid (AA). Inhibition of COX is responsible for the anti-inflammatory activity of conventional NSAIDs.

Inhibitors that demonstrate dual specificity for COX and LOX would have the obvious benefit of inhibiting multiple pathways of arachidonic acid metabolism. Such Inhibitors would block the inflammatory effects of prostaglandins (PG), as well as, those of multiple leukotrienes (LT) by limiting their production. This includes the vasodilation, vasopermeability and chemotactic effects of PGE2, LTB4, LTD4 and LTE4, also known as the slow reacting substance of anaphalaxis. Of these, LTB4 has the most potent chemotactic and chemokinetic effects. (Moore (1985) in *Prostanoids: pharmacological, physiological and clinical relevance*, Cambridge University Press, N.Y., pp. 229-230).

Because the mechanism of action of COX inhibitors overlaps that of most conventional NSAID's, COX inhibitors are used to treat many of the same symptoms, including pain and swelling associated with inflammation in transient conditions and chronic diseases in which inflammation plays a critical role. Transient conditions include treatment of inflammation associated with minor abrasions or contact dermatitis, as well as, skin conditions that are directly associated with the prostaglandin and leukotriene pathways, such as skin hyperpigmentation, age spots, vitilago, systemic lupus erythromatosus, psoriasis, carcinoma, melanoma, and other mammalian skin cancers. The use of COX inhibitors has been expanded to include diseases, such as systemic lupus erythromatosus (SLE) (Goebel et al. (1999) Chem. Res. Toxicol. 12:488-500; Patrono et al. (1985) J. Clin. Invest. 76:1011-1018), as well as, rheumatic skin conditions, such as scleroderma. COX inhibitors are also used for the relief of inflammatory skin conditions that are not of rheumatic origin, such as psoriasis, in which reducing the inflammation resulting from the overproduction of prostaglandins could provide a direct benefit. (Fogh et al. (1993) Acta Derm Venerologica 73:191-193). Recently over expression of 5-lipoxygenase in the skin of patients with system sclerosis has been reported. This has led to the suggestion that the LOX pathway may be of significance in the pathogenesis of system sclerosis and may represent a valid therapeutic target. (Kowal-Bielecka (2001) Arthritis Rheum. 44(8):1865). Finally, the increased enzymatic activity of both the COX-2 and 5-LOX at the site of allergen injections suggests the potential for using dual COX/

LOX inhibitors to treat the symptoms of both the early and late phases of the skin allergic response. (Church (2002) Clin. Exp. Allergy. 32(7):1013).

Topical application of a selective cyclooxygenase inhibitor has been shown to suppress UVB mediated cutaneous inflammation following both acute and long-term exposure. Additionally, edema, dermal neutrophil infiltration and activation, PGE2 levels and the formation of sunburn cells were reduced by the topical application of a COX inhibitor. (Wilgus (2000) Prostaglandins Other Lipid Mediat. 62(4):367). The COX inhibitor Celebrex™ has been shown to reduce the effects of UV induced inflammation when administered systematically (Wilgus et al. (2002) Adv. Exp. Med. Biol. 507:85), and topically (Wilgus et al. (2000) Protaglandins Other Lipid Mediat. 62:367). In animal models, the known COX inhibitor aspirin and various lipoxygenase inhibitors exhibited vasoprotective activity against inflammation and vasodepression resulting from UV irradiation. (Kuhn (1988) Biomed. Biochim. Acta. 47:S320). Acute or long-term chronic UV exposure causes skin damage and photoageing that are characterized by degradation of collagen and accumulation of abnormal elastin in the superficial dermis. A dual COX/LOX inhibitor can be utilized to prevent and treat collagen degradation caused by inflammatory infiltration by significantly reducing the vasodilating, vasopermeability, chemotactic and chemotaxins—prostaglandins (PG), as well as, those of multiple leukotrienes (LT). (Bosset (2003) Br. J. Dermatol. 149 (4):826; Hase (2000) Br. J. Dermatol. 142(2):267). Additionally, chemically induced oxidative stress in mouth skin can be inhibited by separately administrating COX and LOX inhibitors to reduce leukocyte adhesion, infiltration and $H_2O_2$ generation. (Nakamura (2003) Free Radical Biol. Med. 35(9): 997).

In addition to their use as anti-inflammatory agents, another potential role for COX inhibitors is in the treatment of cancer. Over expression of COX has been demonstrated in various human malignancies and inhibitors of COX have been shown to be efficacious in the treatment of animals with skin tumors. While the mechanism of action is not completely understood, the over expression of COX has been shown to inhibit apoptosis and increase the invasiveness of tumorgenic cell types. (Dempke et al. (2001) J. Can. Res. Clin. Oncol. 127:411-17; Moore and Simmons (2000) Current Med. Chem. 7:1131-1144). Up regulated COX production has been implicated in the generation of actinic keratosis and squamous cell carcinoma in skin. Increased amounts of COX were also found in lesions produced by DNA damage. (Buckman et al. (1998) Carcinogenesis 19:723). Therefore, control of expression or protein function of COX would seem to lead to a decrease in the inflammatory response and the eventual progression to cancer. In fact, COX inhibitors such as indomethacin and Celebrex™ have been found to be effective in treating UV induced erythema and tumor formation. (Fischer (1999) Mol. Carcinog. 25:231; Pentland (1999) Carcinogenesis 20:1939). Recently, the over expression of lipoxygenase has also been shown to be related to epidermal tumor development (Muller (2002) Cancer Res. 62(16):4610) and melanoma carcinogenesis (Winer (2002) Melanoma Res. 12(5):429). The arachidonic acid (AA) metabolites generated from lipoxygenase pathways play important roles in tumor growth related signal transduction suggesting that that the inhibition of lipoxygenase pathways should be a valid target to prevent cancer progression. (Cuendet (2000) Drug Metabol Drug Interact 17(4):109; Steele (2003) Mutat Res. 523-524:137). Thus, the use of therapeutic agents having dual COX/LOX inhibitory activity offers significant advantages in the chemoprevention of cancer.

Prostaglandins and leukotrienes also play important roles in the physiological and pathological processes of wounds, burns, scald, acne, microbial infections, dermatitis, and many other diseases and conditions of the skin. The activation of a pro-inflammatory cascade after thermal or chemical burns with significantly elevated cyclooxygenase and lipoxygenase activities are well documented and play an important role in the development of subsequent severe symptoms and immune dysfunction that may lead to multiple organ failure. (Schwacha (2003) Burns 29(1):1; He (2001) J. Burn Care Rehabil. 22(1):58).

Acne is a disease of the pilosebaceous unit with abnormalities in sebum production, follicular epithelial desquamation, bacterial proliferation and inflammation. The inflammatory properties of acne can be detected by polarized light photography and utilized for clinical diagnosis, including an evaluation of the extent of the acne and also to determine the effectiveness of therapy. (Phillips (1997) J. Am. Acad. Dermatol. 37(6):948). Current therapeutic agents for the prevention and treatment of acne include anti-inflammatory agents, like retinoids, antimicrobial agents and hormonal drugs. (Leyden (2003) J. Am. Acad. Dermatol. 49(3 Suppl):S200). Topical application of anti-inflammatory drugs, such as retinoids (Millikan (2003) J. Am. Acad. Dermatol. 4(2):75) and the COX inhibitor salicylic acid (Lee (2003) Dermatol Surg 29(12):1196) have been clinically demonstrated as an effective and safe therapy for the treatment of acne. Additionally, the use of nonsteroidal anti-inflammatory drugs (NSAIDs) are well documented as therapeutic agents for common and uncommon dermatoses, including acne, psoriasis, sun burn, erythema nodosum, cryoglobulinemia, Sweet's syndrome, systemic mastocytosis, urticarial, liverdoid and nodular vasculitis. (Friedman (2002) J. Cutan Med. Surg. 6(5):449).

Flavonoids or bioflavonoids are a widely distributed group of natural products, which have been reported to have antibacterial, anti-inflammatory, antiallergic, antimutagenic, antiviral, antineoplastic, anti-thrombic and vasodilatory activity. The structural unit common to this group of compounds includes two benzene rings on either side of a 3-carbon ring as illustrated by the following general structural formula:

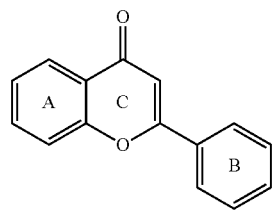

Various combinations of hydroxyl groups, sugars, oxygen and methyl groups attached to this general three ring structure create the various classes of flavonoids, which include flavanols, flavones, flavan-3-ols (catechins), anthocyanins and isoflavones.

Free-B-Ring flavones and flavonols are a specific class of flavonoids, which have no substituent groups on the aromatic B ring (referred to herein as Free-B-Ring flavonoids), as illustrated by the following general structure:

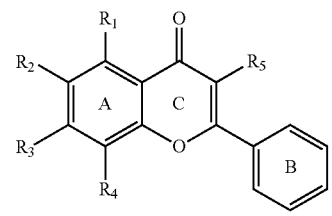

wherein $R_1$, $R_2$, $R_3$, $R_4$, and $R_5$ are independently selected from the group consisting of —H, —OH, —SH, OR, —SR, —NH$_2$, —NHR, —NR$_2$, —NR$_3^+$X$^-$, a carbon, oxygen, nitrogen or sulfur, glycoside of a single or a combination of multiple sugars including, but not limited to aldopentoses, methyl-aldopentose, aldohexoses, ketohexose and their chemical derivatives thereof;

wherein

R is an alkyl group having between 1-10 carbon atoms; and

X is selected from the group of pharmaceutically acceptable counter anions including, but not limited to hydroxyl, chloride, iodide, fluoride, sulfate, phosphate, acetate, carbonate, etc.

Free-B-Ring flavonoids are relatively rare. Out of 9,396 flavonoids synthesized or isolated from natural sources, only 231 Free-B-Ring flavonoids are known (*The Combined Chemical Dictionary*, Chapman & Hall/CRC, Version 5:1 June 2001). Free-B-Ring flavonoids have been reported to have diverse biological activity. For example, galangin (3,5, 7-trihydroxyflavone) acts as antioxidant and free radical scavenger and is believed to be a promising candidate for anti-genotoxicity and cancer chemoprevention. (Heo et al. (2001) Mutat. Res. 488(2):135-150). It is an inhibitor of tyrosinase monophenolase (Kubo et al. (2000) Bioorg. Med. Chem. 8(7):1749-1755), an inhibitor of rabbit heart carbonyl reductase (Imamura et al. (2000) J. Biochem. 127(4):653-658), has antimicrobial activity (Afolayan and Meyer (1997) Ethnopharmacol. 57(3):177-181) and antiviral activity (Meyer et al. (1997) J. Ethnopharmacol. 56(2):165-169). Baicalein and two other Free-B-Ring flavonoids, have anti-proliferative activity against human breast cancer cells. (So et al. (1997) Cancer Lett. 112(2):127-133).

Typically, flavonoids have been tested for biological activity randomly based upon their availability. Occasionally, the requirement of substitution on the B-ring has been emphasized for specific biological activity, such as the B-ring substitution required for high affinity binding to p-glycoprotein (Boumendjel et al. (2001) Bioorg. Med. Chem. Lett. 11(1): 75-77); cardiotonic effect (Itoigawa et al. (1999) J. Ethnopharmacol. 65(3): 267-272), protective effect on endothelial cells against linoleic acid hydroperoxide-induced toxicity (Kaneko and Baba (1999) Biosci Biotechnol. Biochem 63(2): 323-328), COX-1 inhibitory activity (Wang (2000) Phytomedicine 7:15-19) and prostaglandin endoperoxide synthase (Kalkbrenner et al. (1992) Pharmacology 44(1):1-12). Only a few publications have mentioned the significance of the unsubstituted B ring of the Free-B-Ring flavonoids. One example, is the use of 2-phenyl flavones, which inhibit NADPH quinone acceptor oxidoreductase, as potential anti-coagulants. (Chen et al. (2001) Biochem. Pharmacol. 61(11): 1417-1427).

The mechanism of action with respect to the anti-inflammatory activity of various Free-B-Ring flavonoids has been controversial. The anti-inflammatory activity of the Free-B-Ring flavonoids, chrysin (Liang et al. (2001) FEBS Lett. 496(1):12-18), wogonin (Chi et al. (2001) Biochem. Pharmacol. 61:1195-1203) and halangin (Raso et al. (2001) Life Sci. 68(8):921-931), has been associated with the suppression of inducible cyclooxygenase and nitric oxide synthase via activation of peroxisome proliferator activated receptor gamma (PPARγ) and influence on degranulation and AA release. (Tordera et al. (1994) Z. Naturforsch [C] 49:235-240). It has been reported that oroxylin, baicalein and wogonin inhibit 12-lipoxygenase activity without affecting cyclooxygenase. (You et al. (1999) Arch. Pharm. Res. 22(1):18-24). More recently, the anti-inflammatory activity of wogonin, baicalin and baicalein has been reported as occurring through inhibition of inducible nitric oxide synthase and cox-2 gene expression induced by nitric oxide inhibitors and lipopolysaccharide. (Chen et al. (2001) Biochem. Pharmacol. 61(11):1417-1427). It has also been reported that oroxylin acts via suppression of NFκB activation. (Chen et al. (2001) Biochem. Pharmacol. 61(11):1417-1427). Finally, wogonin reportedly inhibits inducible PGE2 production in macrophages. (Wakabayashi and Yasui (2000) Eur. J. Pharmacol. 406 (3):477-481).

Inhibition of the phosphorylation of mitogen-activated protein kinase and inhibition of Ca$^{2+}$ ionophore A23187 induced PGE$_2$ release by baicalein has been reported as the mechanism of anti-inflammatory activity of *Scutellariae radix*. (Nakahata et al. (1999) Nippon Yakurigaku Zasshi, 114, Supp. 11:215P-219P; Nakahata et al. (1998) Am. J. Chin Med. 26:311-323). Baicalin from *Scutellaria baicalensis*, reportedly inhibits superantigenic staphylococcal exotoxins stimulated T-cell proliferation and production of IL-1β, IL-6, tumor necrosis factor-α (TNF-α), and interferon-γ (IFN-γ). (Krakauer et al. (2001) FEBS Lett. 500:52-55). Thus, the anti-inflammatory activity of baicalin has been associated with inhibiting the pro-inflammatory cytokines mediated signaling pathways activated by superantigens. However, it has also been proposed that the anti-inflammatory activity of baicalin is due to the binding of a variety of chemokines, which limits their biological activity. (Li et al. (2000) Immunopharmacology 49:295-306). Recently, the effects of baicalin on adhesion molecule expression induced by thrombin and thrombin receptor agonist peptide (Kimura et al. (2001) Planta Med. 67:331-334), as well as, the inhibition of mitogen-activated protein kinase cascade (MAPK) (Nakahata et al. (1999) Nippon Yakurigaku Zasshi, 114, Supp 11:215P-219P; Nakahata et al. (1998) Am. J. Chin Med. 26:311-323) have been reported.

The Chinese medicinal plant, *Scutellaria baicalensis* contains significant amounts of Free-B-Ring flavonoids, including baicalein, baicalin, wogonin and baicalenoside. Traditionally, this plant has been used to treat a number of conditions including clearing away heat, purging fire, dampness-warm and summer fever syndromes; polydipsia resulting from high fever; carbuncle, sores and other pyogenic skin infections; upper respiratory infections, such as acute tonsillitis, laryngopharyngitis and scarlet fever; viral hepatitis; nephritis; pelvitis; dysentery; hematemesis and epistaxis. This plant has also traditionally been used to prevent miscarriage. (*Encyclopedia of Chinese Traditional Medicine*, ShangHai Science and Technology Press, ShangHai, China, 1998). Clinically *Scutellaria* is now used to treat conditions such as pediatric pneumonia, pediatric bacterial diarrhea, viral hepatitis, acute gallbladder inflammation, hypertension, topical acute inflammation, resulting from cuts and surgery, bronchial asthma and upper respiratory infections. (*Encyclopedia of Chinese Traditional Medicine*, ShangHai Science and Technology Press, ShangHai, China, 1998). The pharmacological efficacy of *Scutellaria* roots for treating bronchial asthma is reportedly related to the presence of Free-B-Ring flavonoids and their suppression of eotaxin associated recruitment of eosinophils. (Nakajima et al. (2001) Planta Med. 67(2):132-135).

To date, a number of naturally occurring Free-B-Ring flavonoids have been commercialized for varying uses. For example, liposome formulations of *Scutellaria* extracts have been utilized for skin care (U.S. Pat. Nos. 5,643,598; 5,443, 983). Baicalin has been used for preventing cancer, due to its inhibitory effects on oncogenes (U.S. Pat. No. 6,290,995). Baicalin and other compounds have been used as antiviral, antibacterial and immunomodulating agents (U.S. Pat. No. 6,083,921 and WO98/42363) and as natural anti-oxidants (WO98/49256 and Poland Pub. No. 9,849,256). *Scutellaria baicalensis* root extract has been formulated as a supplemental sun screen agent with additive effects of the cumulative SPFs of each individual component in a topical formulation (WO98/19651). Chrysin has been used for its anxiety reducing properties (U.S. Pat. No. 5,756,538). Anti-inflammatory flavonoids are used for the control and treatment of anorectal and colonic diseases (U.S. Pat. No. 5,858,371), and inhibition of lipoxygenase (U.S. Pat. No. 6,217,875). These compounds are also formulated with glucosamine collagen and other ingredients for repair and maintenance of connective tissue (U.S. Pat. No. 6,333,304). Flavonoid esters constitute active ingredients for cosmetic compositions (U.S. Pat. No. 6,235,294). U.S. application Ser. No. 10/091,362, filed Mar. 1, 2002, entitled "Identification of Free-B-Ring Flavonoids as Potent COX-2 Inhibitors," and U.S. application Ser. No. 10/427,746, filed Jul. 22, 2003, entitled "Formulation of a Mixture of Free-B-Ring Flavonoids and Flavans as a Therapeutic Agent" both disclose a method for inhibiting the cyclooxygenase enzyme COX-2 by administering a composition comprising a Free-B-Ring flavonoid or a composition containing a mixture of Free-B-Ring flavonoids to a host in need thereof. This is the first report of a link between Free-B-Ring flavonoids and COX-2 inhibitory activity. These applications are specifically incorporated herein by reference in their entirety.

Japanese Pat. No. 63027435, describes the extraction, and enrichment of baicalein and Japanese Pat. No. 61050921 describes the purification of baicalin.

Flavans include compounds illustrated by the following general structure:

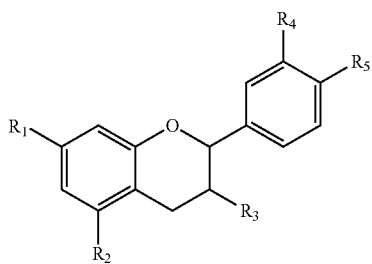

wherein $R_1$, $R_2$, $R_3$, $R_4$ and $R_5$ are independently selected from the group consisting of —H, —OH, —SH, —OCH$_3$, —SCH$_3$, —OR, —SR, —NH$_2$, —NRH, —NR$_2$, —NR$_3^+$X$^-$, esters of the mentioned substitution groups, including, but not limited to, gallate, acetate, cinnamoyl and hydroxyl-cinnamoyl esters, trihydroxybenzoyl esters and caffeoyl esters, and their chemical derivatives thereof; a carbon, oxygen, nitrogen or sulfur glycoside of a single or a combination of multiple sugars including, but not limited to, aldopentoses, methyl aldopentose, aldohexoses, ketohexose and their chemical derivatives thereof; dimer, trimer and other polymerized flavans;

wherein

R is an alkyl group having between 1-10 carbon atoms; and

X is selected from the group of pharmaceutically acceptable counter anions including, but not limited to hydroxyl, chloride, iodide, sulfate, phosphate, acetate, fluoride, and carbonate, etc.

Catechin is a flavan, found primarily in green tea, having the following structure:

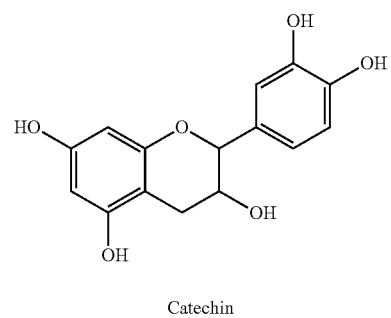

Catechin

Catechin works both alone and in conjunction with other flavonoids found in tea, and has both antiviral and antioxidant activity. Catechin has been shown to be effective in the treatment of viral hepatitis. It also appears to prevent oxidative damage to the heart, kidney, lungs and spleen and has been shown to inhibit the growth of stomach cancer cells.

Catechin and its isomer epicatechin inhibit prostaglandin endoperoxide synthase with an IC$_{50}$ value of 40 μM. (Kalkbrenner et al. (1992) Pharmacol. 44:1-12). Five flavan-3-ol derivatives, including (+)-catechin and gallocatechin, isolated from four plant species: *Atuna racemosa, Syzygium carynocarpum, Syzygium malaccense* and *Vantanea peruviana*, exhibit equal to weaker inhibitory activity against COX-2, relative to COX-1, with IC$_{50}$ values ranging from 3.3 μM to 138 μM (Noreen et al. (1998) Planta Med. 64:520-524). (+)-Catechin, isolated from the bark of *Ceiba pentandra*, inhibits COX-1 with an IC$_{50}$ value of 80 μM (Noreen et al. (1998) J. Nat. Prod. 61:8-12). Commercially available pure (+)-catechin inhibits COX-1 with an IC$_{50}$ value of around 183 to 279 μM depending upon the experimental conditions, with no selectivity for COX-2. (Noreen et al. (1998) J. Nat. Prod. 61:1-7).

Green tea catechin, when supplemented into the diets of Sprague dawley male rats, lowered the activity level of platelet PLA$_2$ and significantly reduced platelet cyclooxygenase levels. (Yang et al. (1999) J. Nutr. Sci. Vitaminol. 45:337-346). Catechin and epicatechin reportedly weakly suppress cox-2 gene transcription in human colon cancer DLD-1 cells (IC$_{50}$=415.3 μM). (Mutoh et al. (2000) Jpn. J. Cancer Res. 91:686-691). The neuroprotective ability of (+)-catechin from red wine results from the antioxidant properties of catechin, rather than inhibitory effects on intracellular enzymes, such as cyclooxygenase, lipoxygenase, or nitric oxide synthase (Bastianetto et al. (2000) Br. J. Pharmacol. 131:711-720). Catechin derivatives purified from green and black tea, such as epigallocatechin-3-gallate (EGCG), epigallocatechin (EGC), epicatechin-3-gallate (ECG), and theaflavins showed inhibition of cyclooxygenase and lipoxygenase dependent metabolism of AA in human colon mucosa and colon tumor tissues (Hong et al. (2001) Biochem. Pharmacol. 62:1175-1183) and induce cox-2 expression and PGE$_2$ production (Park et al. (2001) Biochem. Biophys. Res. Commun. 286: 721-725). Epiafzelechin isolated from the aerial parts of *Celastrus orbiculatus* exhibited dose-dependent inhibition of COX-1 activity with an IC$_{50}$ value of 15 μM and also demonstrated anti-inflammatory activity against carrageenin-induced mouse paw edema following oral administration at a dosage of 100 mg/kg. (Min et al. (1999) Planta Med. 65:460-462).

*Acacia* is a genus of leguminous trees and shrubs. The genus *Acacia* includes more than 1000 species belonging to the family of Leguminosae and the subfamily of Mimosoideae. *Acacias* are distributed worldwide in tropical and subtropical areas of Central and South America, Africa, parts of Asia, as well as, Australia, which has the largest number of endemic species. *Acacias* are very important economically, providing a source of tannins, gums, timber, fuel and fodder. Tannins, which are isolated primarily from bark, are used extensively for tanning hides and skins. Some *Acacia* barks are also used for flavoring local spirits. Some indigenous species like *A. sinuata* also yield saponins, which are any of various plant glucosides that form soapy lathers when mixed and agitated with water. Saponins are used in detergents, foaming agents and emulsifiers. The flowers of some *Acacia* species are fragrant and used to make perfume. The heartwood of many *Acacias* is used for making agricultural implements and also provides a source of firewood. *Acacia* gums find extensive use in medicine and confectionary and as sizing and finishing materials in the textile industry.

To date, approximately 330 compounds have been isolated from various *Acacia* species. Flavonoids are the major class of compounds isolated from *Acacias*. Approximately 180 different flavonoids have been identified, 111 of which are flavans. Terpenoids are second largest class of compounds isolated from species of the *Acacia* genus, with 48 compounds having been identified. Other classes of compounds isolated from *Acacia* include, alkaloids (28), amino acids/peptides (20), tannins (16), carbohydrates (15), oxygen heterocycles (15) and aliphatic compounds (10). (Buckingham, *The Combined Chemical Dictionary*, Chapman & Hall CRC, version 5:2, December 2001).

Phenolic compounds, particularly flavans are found in moderate to high concentrations in all *Acacia* species. (Abdulrazak et al. (2000) Journal of Animal Sciences. 13:935-940). Historically, most of the plants and extracts of the *Acacia* genus have been utilized as astringents to treat gastrointestinal disorders, diarrhea, indigestion and to stop bleeding. (Vautrin (1996) Universite Bourgogne (France) European abstract 58-01C:177; Saleem et al. (1998) Hamdard Midicus. 41:63-67). The bark and pods of *Acacia arabica* Willd. contain large quantities of tannins and have been utilized as astringents and expectorants. (Nadkarni (1996) India Materia Medica, Bombay Popular Prakashan, pp. 9-17). Diarylpropanol derivatives, isolated from stem bark of *Acacia tortilis* from Somalia, have been reported to have smooth muscle relaxing effects. (Hagos et al. (1987) Planta Medica. 53:27-31, 1987). It has also been reported that terpenoid saponins isolated from *Acacia victoriae* have an inhibitory effect on dimethylbenz(a)anthracene-induced murine skin carcinogenesis (Hanausek et al. (2000) Proceedings American Association for Cancer Research Annual Meeting 41:663) and induce apotosis (Haridas et al. (2000) Proceedings American Association for Cancer Research Annual Meeting. 41:600). Plant extracts from *Acacia nilotica* have been reported to have spasmogenic, vasoconstrictor and antihypertensive activity (Amos et al. (1999) Phytotherapy Research 13:683-685; Gilani et al. (1999) Phytotherapy Research. 13:665-669), and antiplatelet aggregatory activity (Shah et al. (1997) General Pharmacology. 29:251-255). Anti-inflammatory activity has been reported for *A. nilotica*. It was speculated that flavonoids, polysaccharides and organic acids were potential active components. (Dafallah and Al-Mustafa (1996) American Journal of Chinese Medicine. 24:263-269). To date, the only reported 5-lipoxygenase inhibitor isolated from *Acacia* is a monoterpenoidal carboxamide (Seikine et al. (1997) Chemical and Pharmaceutical Bulletin. 45:148-11).

The extract from the bark of *Acacia* has been patented in Japan for external use as a whitening agent (Abe, JP10025238), as a glucosyl transferase inhibitor for dental applications (Abe, JP07242555), as a protein synthesis inhibitor (Fukai, JP 07165598), as an active oxygen scavenging agent for external skin preparations (Honda, JP 07017847, Bindra U.S. Pat. No. 6,126,950), and as a hyaluronidase inhibitor for oral consumption to prevent inflammation, pollinosis and cough (Ogura, JP 07010768).

To date, Applicant is unaware of any reports of a formulation combining only Free-B-Ring-Flavonoids and flavans as the primary biologically active components for the dual inhibition of the COX/LOX enzymes that yield significant benefit to mammal skin conditions.

SUMMARY OF THE INVENTION

The present invention includes methods that are effective in simultaneously inhibiting both the cyclooxygenase (COX) and lipoxygenase (LOX) enzymes, for use in the prevention and treatment of diseases and conditions related to the skin. The method for the simultaneous dual inhibition of the COX and LOX enzymes is comprised administering, preferably topically, a composition comprised of a mixture of Free-B-Ring flavonoids and flavans synthesized and/or isolated from a single plant or multiple plants to a host in need thereof. This composition of matter is referred to herein as Soliprin™. The efficacy of this method was demonstrated with purified enzymes, in different cell lines, in multiple animal models and eventually in a human clinical study. The ratio of the Free-B-Ring flavonoids to flavans in the composition can be in the range of 99.9:0.1 of Free-B-Ring flavonoids:flavans to 0.1:99.9 Free-B-Ring flavonoids:flavans. In specific embodiments of the present invention, the ratio of Free-B-Ring flavonoids to flavans is selected from the group consisting of approximately 90:10, 80:20, 70:30, 60:40, 50:50, 40:60, 30:70, 20:80 and 10:90. In a preferred embodiment of this invention, the ratio of Free-B-Ring flavonoids:flavans in the composition of matter is 80:20. In a preferred embodiment, the Free-B-Ring flavonoids are isolated from a plant or plants in the *Scutellaria* genus of plants and the flavans are isolated from a plant or plants in the *Acacia* genus of plants.

The present invention also includes methods for the prevention and treatment of COX and LOX mediated diseases and conditions of the skin. The method for preventing and treating COX and LOX mediated diseases and conditions of the skin is comprised of administering, preferably topically, to a host in need thereof an effective amount of a composition comprising a mixture of Free-B-Ring flavonoids and flavans synthesized and/or isolated from a single plant or multiple plants and a pharmaceutically acceptable carrier. The ratio of the Free-B-Ring flavonoids to flavans in the composition can be in the range of 99.9:0.1 of Free-B-Ring flavonoids:flavans to 0.1:99.9 Free-B-Ring flavonoids:flavans. In specific embodiments of the present invention, the ratio of Free-B-Ring flavonoids to flavans is selected from the group consisting of approximately 90:10, 80:20, 70:30, 60:40, 50:50, 40:60, 30:70, 20:80 and 10:90. In a preferred embodiment of this invention, the ratio of Free-B-Ring flavonoids:flavans in the composition of matter is 80:20. In a preferred embodiment, the Free-B-Ring flavonoids are isolated from a plant or plants in the *Scutellaria* genus of plants and the flavans are isolated from a plant or plants in the *Acacia* genus of plants.

The Free-B-Ring flavonoids, also referred to herein as Free-B-Ring flavones and flavonols, that can be used in accordance with the following invention include compounds illustrated by the following general structure:

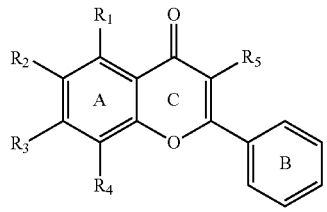

wherein $R_1$, $R_2$, $R_3$, $R_4$, and $R_5$ are independently selected from the group consisting of —H, —OH, —SH, OR, —SR, —$NH_2$, —NHR, —$NR_2$, —$NR_3^+X^-$, a carbon, oxygen, nitrogen or sulfur, glycoside of a single or a combination of multiple sugars including, but not limited to aldopentoses, methyl-aldopentose, aldohexoses, ketohexose and their chemical derivatives thereof;

wherein

R is selected from an alkyl group having between 1-10 carbon atoms; and

X is selected from the group of pharmaceutically acceptable counter anions including, but not limited to hydroxyl, chloride, iodide, sulfate, phosphate, acetate, fluoride, carbonate, etc.

The Free-B-Ring flavonoids of this invention may be obtained by synthetic methods or extracted from the family of plants including, but not limited to Annonaceae, Asteraceae, Bignoniaceae, Combretaceae, Compositae, Euphorbiaceae, Labiatae, Lauranceae, Leguminosae, Moraceae, Pinaceae, Pteridaceae, Sinopteridaceae, Ulmaceae and Zingiberacea. The Free-B-Ring flavonoids can be extracted, concentrated, and purified from the following genus of high plants, including but not limited to *Desmos, Achyrocline, Oroxylum, Buchenavia, Anaphalis, Cotula, Gnaphalium, Helichrysum, Centaurea, Eupatorium, Baccharis, Sapium, Scutellaria, Molsa, Colebrookea, Stachys, Origanum, Ziziphora, Lindera, Actinodaphne, Acacia, Derris, Glycyrrhiza, Millettia, Pongamia, Tephrosia, Artocarpus, Ficus, Pityrogramma, Notholaena, Pinus, Ulmus* and *Alpinia.*

The flavans that can be used in accordance with the following invention include compounds illustrated by the following general structure:

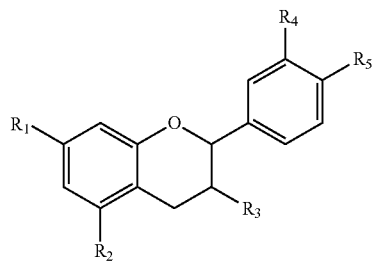

wherein $R_1$, $R_2$, $R_3$, $R_4$ and $R_5$ are independently selected from the group consisting of H, —OH, —SH, —$OCH_3$, —$SCH_3$, —OR, —SR, —$NH_2$, —NRH, —$NR_2$, —$NR_3^+X^-$, esters of the mentioned substitution groups, including, but not limited to, gallate, acetate, cinnamoyl and hydroxyl-cinnamoyl esters, trihydroxybenzoyl esters and caffeoyl esters; thereof carbon, oxygen, nitrogen or sulfur glycoside of a single or a combination of multiple sugars including, but not limited to, aldopentoses, methyl aldopentose, aldohexoses, ketohexose and their chemical derivatives thereof; dimer, trimer and other polymerized flavans;

wherein

R is selected from an alkyl group having between 1-10 carbon atoms; and

X is selected from the group of pharmaceutically acceptable counter anions including, but not limited to hydroxyl, chloride, iodide, sulfate, phosphate, acetate, fluoride, carbonate, etc.

The flavans of this invention may be obtained from a plant or plants selected from the genus of *Acacia*. In a preferred embodiment, the plant is selected from the group consisting of *Acacia catechu, Acacia concinna, Acacia farnesiana, Acacia Senegal, Acacia speciosa, Acacia arabica, A. caesia, A. pennata, A. sinuata. A. mearnsii, A. picnantha, A. dealbata, A. auriculiformis, A. holoserecia* and *A. mangium.*

In one embodiment, the present invention includes a method for preventing and treating a number of COX and LOX mediated diseases and conditions of the skin including, but not limited to sun burns, thermal burns, acne, topical wounds, minor inflammatory conditions caused by fungal, microbial and viral infections, vitilago, systemic lupus erythromatosus, psoriasis, carcinoma, melanoma, as well as other mammal skin cancers. In another embodiment the present invention includes a method for preventing and treating skin damage resulting from exposure to ultraviolet (UV) radiation, chemicals, heat, wind and dry environments. In yet another embodiment the present invention includes a method for preventing and treating wrinkles, saggy skin, lines and dark circles around the eyes, dermatitis and other allergy related conditions of the skin.

The present invention further includes therapeutic compositions comprising the therapeutic agents of the present invention. In addition to their use for the prevention and treatment of the above described diseases and conditions of the skin, the therapeutic compositions described herein can also be used to sooth sensitive skin and to provide smooth and youthful skin with improved elasticity, reduced and delayed aging, enhanced youthful appearance and texture, and increased flexibility, firmness, smoothness and suppleness.

The method of prevention and treatment according to this invention comprises administering topically to a host in need thereof a therapeutically effective amount of the formulated Free-B-Ring flavonoids and flavans isolated from a single source or multiple sources. The purity of the individual and/or a mixture of multiple Free-B-Ring flavonoids and flavans includes, but is not limited to 0.01% to 100%, depending on the methodology used to obtain the compound(s). In a preferred embodiment, doses of the mixture of Free-B-Ring flavonoids and flavans containing the same are an efficacious, nontoxic quantity generally selected from the range of 0.001% to 100% based on total weight of the topical formulation. Persons skilled in the art using routine clinical testing are able to determine optimum doses for the particular ailment being treated.

The present invention includes an evaluation of different compositions of Free-B-Ring flavonoids and flavans using enzymatic and in vivo models to optimize the formulation and obtain the desired physiological activity. The efficacy and safety of this formulation is also demonstrated in human clinical studies. The compositions of this invention can be administered by any method known to one of ordinary skill in the art. The modes of administration include, but are not limited to, enteral (oral) administration, parenteral (intravenous, subcutaneous, and intramuscular) administration and topical application. In the preferred embodiment the method of treatment according to this invention comprises administering topically to a host in need thereof a therapeutically effective amount of a mixture of Free-B-Ring flavonoids and flavans synthesized and/or isolated from a single plant or multiple plants.

It is to be understood that both the foregoing general description and the following detailed description are exemplary and explanatory only and are not restrictive of the invention as claimed.

BRIEF DESCRIPTION OF THE FIGURES

With reference to FIG. 15, it can be seen that topical applications of Soliprin™, both before and after UV radiation, significantly reduced erythema scores as compared with the control group and the group that was administered the standard treatment agent-Sooth-a-caine.

DETAILED DESCRIPTION OF THE INVENTION

Figure 1:
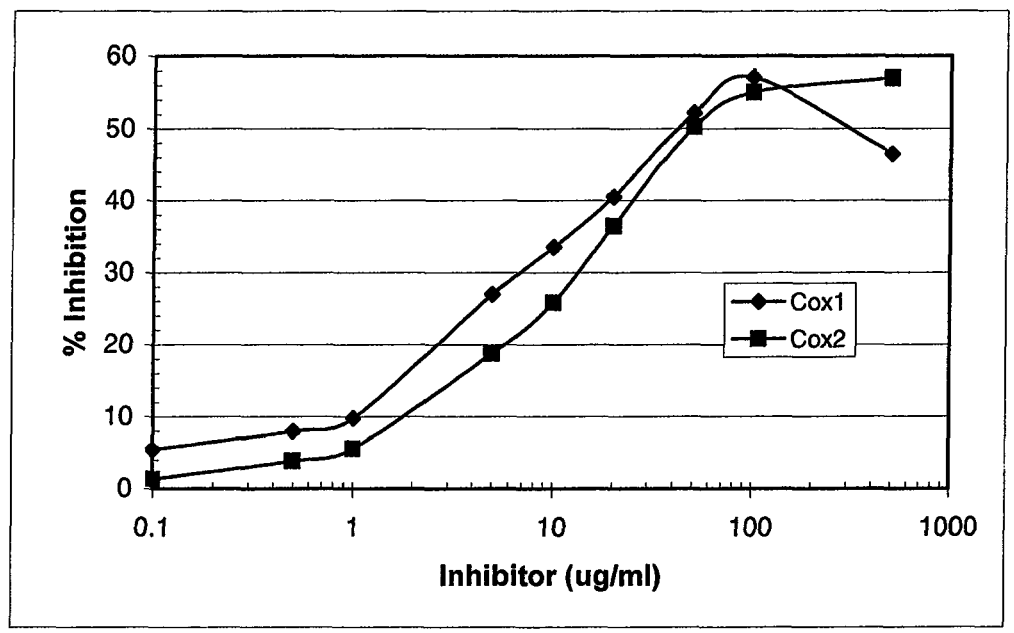
FIG. 1 depicts graphically a profile of the inhibition of COX-1 and COX-2 by a standardized Free-B-Ring flavonoid extract (83% baicalin based on HPLC) which was isolated from *Scutellaria baicalensis*. The extract was examined for its inhibition of the peroxidase activity of recombinant ovine COX-1 (♦) and ovine COX-2 (■). The data is presented as percent inhibition vs. inhibitor concentration (µg/mL). The $IC_{50}$ for COX-1 was calculated as 0.24 µg/mL/unit of enzyme while the $IC_{50}$ for COX-2 was calculated as 0.48 µg/mL/unit.

Various terms are used herein to refer to aspects of the present invention. To aid in the clarification of the description of the components of this invention, the following definitions are provided.

It is to be noted that the term "a" or "an" entity refers to one or more of that entity; for example, a flavonoid refers to one or more flavonoids. As such, the terms "a" or "an", "one or more" and "at least one" are used interchangeably herein.

"Free-B-Ring Flavonoids" as used herein are a specific class of flavonoids, which have no substitute groups on the aromatic B-ring, as illustrated by the following general structure:

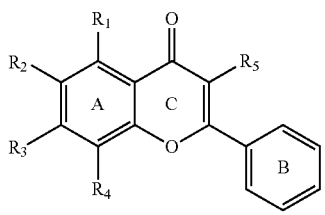

wherein $R_1$, $R_2$, $R_3$, $R_4$, and $R_5$ are independently selected from the group consisting of —H, —OH, —SH, OR, —SR, —NH$_2$, —NHR, —NR$_2$, —NR$_3$$^+$X$^-$, a carbon, oxygen, nitrogen or sulfur, glycoside of a single or a combination of multiple sugars including, but not limited to aldopentoses, methyl-aldopentose, aldohexoses, ketohexose and their chemical derivatives thereof;

wherein

R is an alkyl group having between 1-10 carbon atoms; and

X is selected from the group of pharmaceutically acceptable counter anions including, but not limited to hydroxyl, chloride, iodide, sulfate, phosphate, acetate, fluoride, carbonate, etc.

"Flavans" as used herein refer to a specific class of flavonoids, which can be generally represented by the following general structure:

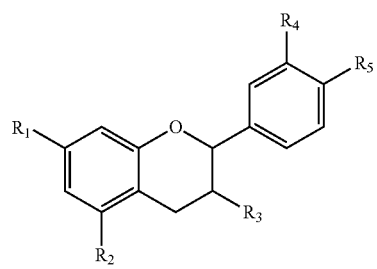

wherein $R_1$, $R_2$, $R_3$, $R_4$ and $R_5$ are independently selected from the group consisting of H, —OH, —SH, —OCH$_3$, —SCH$_3$, —OR, —SR, —NH$_2$, —NRH, —NR$_2$, —NR$_3$$^+$X$^-$, esters of substitution groups, including, but not limited to, gallate, acetate, cinnamoyl and hydroxyl-cinnamoyl esters, trihydroxybenzoyl esters and caffeoyl esters and their chemical derivatives thereof; carbon, oxygen, nitrogen or sulfur glycoside of a single or a combination of multiple sugars including, but not limited to, aldopentoses, methyl aldopentose, aldohexoses, ketohexose and their chemical derivatives thereof; dimer, trimer and other polymerized flavans;

wherein

R is an alkyl group having between 1-10 carbon atoms; and

X is selected from the group of pharmaceutically acceptable counter anions including, but not limited to hydroxyl, chloride, iodide, sulfate, phosphate, acetate, fluoride, carbonate, etc.

"Therapeutic" as used herein, includes treatment and/or prophylaxis. When used, therapeutic refers to humans as well as other animals.

"Pharmaceutically or therapeutically effective dose or amount" refers to a dosage level sufficient to induce a desired biological result. That result may be the alleviation of the signs, symptoms or causes of a disease or any other alteration of a biological system that is desired.

"Placebo" refers to the substitution of the pharmaceutically or therapeutically effective dose or amount dose sufficient to induce a desired biological that may alleviate the signs, symptoms or causes of a disease with a non-active substance.

A "host" or "patient" is a living subject, human or animal, into which the compositions described herein are administered. Thus, the invention described herein may be used for veterinary as well as human applications and the terms "patient" or "host" should not be construed in a limiting manner. In the case of veterinary applications, the dosage ranges can be determined as described below, taking into account the body weight of the animal.

Note that throughout this application various citations are provided. Each citation is specifically incorporated herein in its entirety by reference.

The current invention provides methods for the extraction (Example 1, Table 1) of plants that contain Free-B-Ring flavonoids and flavans with organic and aqueous solvents. The crude extracts were assayed for cyclooxygenase inhibitory activity (Example 2, Tables 2 and 3). Purified Free-B-Ring flavonoids and flavans demonstrated inhibitory activity against cyclooxygenase (COX) and lipoxygenase (LOX), respectively, as shown in Examples 3 and 4. Methods for analyzing and quantifying the extracts are described in Examples 5 and 6 and the procedures to generate standardized Free-B-Ring flavonoids and flavans from botanical origins are provided in Examples 7 and 8.

In one embodiment of the present invention, the standardized Free-B-Ring flavonoid extract is comprised of the active compounds having a purity of between 1-99% (by weight) of total Free-B-Ring flavonoids as defined in Examples 1, 2, 5 and 8. Baicalin is the major active component in the extract, which accounts for approximately 50-90% (by weight) of the total Free-B-Ring flavonoids. In a preferred embodiment, the standardized extract contains >70% total Free-B-Ring flavonoids in which >75% of the Free-B-Ring flavonoids is baicalin.

In one embodiment, the standardized flavan extract is comprised of the active compounds having a purity of between 1-99% (by weight) total flavans as defined in Examples 1, 4, 6 and 7. Catechin is the major active component in the extract and accounts for 50-95% (by weight) of the total flavans. In a preferred embodiment, the standardized flavan extract contains >80% total flavans in which >70% of flavans is catechin.

In one embodiment, Soliprin™ is produced by mixing the above two extracts or synthetic compounds in a ratio from 99:1 to 1:99. The preferred ratios of Free-B-Ring flavonoids to flavans are 80:20 as defined in Example 9 and Table 10 and 15:85 as defined in Example 9.

The concentration of Free-B-Ring flavonoids in Soliprin™ can be from about 1% to 99% and the concentration of flavans in Soliprin™ can be from 99% to 1%. In a preferred embodiment of the invention, the concentration of total Free-B-Ring flavonoids in Soliprin™ is approximately 20% with a baicalin content of approximately 15% of total weight of the Soliprin™; and the concentration of total flavans in Soliprin™ is approximately 75% with a catechin content of approximately 70%. In this embodiment, the total active components (Free-B-Ring flavonoids plus flavans) in Soliprin™ are >90% of the total weight.

The present invention includes methods that are effective in simultaneously inhibiting both the cyclooxygenase (COX) and lipoxygenase (LOX) enzymes, for use in the prevention and treatment of diseases and conditions related to the skin. The method for the simultaneous dual inhibition of the COX and LOX enzymes is comprised of administering, preferably topically a composition comprised of a mixture of Free-B-Ring flavonoids and flavans synthesized and/or isolated from a single plant or multiple plants to a host in need thereof. This composition of matter is referred to herein as Soliprin™. The efficacy of this method was demonstrated with purified enzymes, in different cell lines, in multiple animal models and eventually in a human clinical study. The ratio of the Free-B-Ring flavonoids to flavans in the composition can be in the range of 99.9:0.1 of Free-B-Ring flavonoids:flavans to 0.1:99.9 Free-B-Ring flavonoids:flavans. In specific embodiments of the present invention, the ratio of Free-B-Ring flavonoids to flavans is selected from the group consisting of approximately 90:10, 80:20, 70:30, 60:40, 50:50, 40:60, 30:70, 20:80 and 10:90. In a preferred embodiment of this invention, the ratio of Free-B-Ring flavonoids:flavans in the composition of matter is 20:80. In a preferred embodiment, the Free-B-Ring flavonoids are isolated from a plant or plants in the *Scutellaria* genus of plants and the flavans are isolated from a plant or plants in the *Acacia* genus of plants.

The present invention also includes methods for the prevention and treatment of COX and LOX mediated diseases and conditions of the skin. The method for preventing and treating COX and LOX mediated diseases and conditions of the skin is comprised of administering, preferably topically, to a host in need thereof an effective amount of a composition comprised of a mixture of Free-B-Ring flavonoids and flavans synthesized and/or isolated from a single plant or multiple plants and a pharmaceutically acceptable carrier. The ratio of the Free-B-Ring flavonoids to flavans in the composition can be in the range of 99.9:0.1 of Free-B-Ring flavonoids:flavans to 0.1:99.9 Free-B-Ring flavonoids:flavans. In specific embodiments of the present invention, the ratio of Free-B-ring flavonoids to flavans is selected from the group consisting of approximately 90:10, 80:20, 70:30, 60:40, 50:50, 40:60, 30:70, 20:80 and 10:90. In a preferred embodiment of this invention, the ratio of Free-B-Ring flavonoids:flavans in the composition of matter is 20:80. In a preferred embodiment, the Free-B-Ring flavonoids are isolated from a plant or plants in the *Scutellaria* genus of plants and the flavans are isolated from a plant or plants in the *Acacia* genus of plants.

In one embodiment, the present invention includes a method for preventing and treating a number of COX and LOX mediated diseases and conditions of the skin including, but not limited to sun burns, thermal burns, acne, topical wounds, minor inflammatory conditions caused by fungal, microbial and viral infections, vitilago, systemic lupus erythromatosus, psoriasis, carcinoma, melanoma, as well as other mammal skin cancers. In another embodiment the present invention includes a method for preventing and treating skin damage resulting from exposure to UV radiation, chemicals, heat, wind and dry environments. In yet another embodiment the present invention includes a method for preventing and treating wrinkles, saggy skin, lines and dark circles around the eyes, dermatitis and other allergy related conditions of the skin.

The present invention further includes therapeutic compositions comprising the therapeutic agents of the present invention. In addition to their use for the prevention and treatment of the above described diseases and conditions of the skin, the therapeutic compositions described herein can be used to sooth sensitive skin and to provide smooth and youthful skin with improved elasticity, reduced and delayed aging, enhanced youthful appearance and texture, and increased flexibility, firmness, smoothness and suppleness.

The Free-B-Ring flavonoids that can be used in accordance with the instant invention include compounds illustrated by the general structure set forth above. The Free-B-Ring flavonoids of this invention may be obtained by synthetic methods or may be isolated from the family of plants including, but not limited to Annonaceae, Asteraceae, Bignoniaceae, Combretaceae, Compositae, Euphorbiaceae, Labiatae, Lauranceae, Leguminosae, Moraceae, Pinaceae, Pteridaceae, Sinopteridaceae, Ulmaceae, and Zingiberacea. The Free-B-Ring flavonoids can be extracted, concentrated, and purified from the following genus of high plants, including but not limited to *Desmos, Achyrocline, Oroxylum, Buchenavia, Anaphalis, Cotula, Gnaphalium, Helichrysum, Centaurea, Eupatorium, Baccharis, Sapium, Scutellaria, Molsa, Colebrookea, Stachys, Origanum, Ziziphora, Lindera, Actinodaphne, Acacia, Derris, Glycyrrhiza, Millettia, Pongamia, Tephrosia, Artocarpus, Ficus, Pityrogramma, Notholaena, Pinus, Ulmus* and *Alpinia*.

The flavonoids can be found in different parts of plants, including but not limited to stems, stem barks, twigs, tubers, roots, root barks, young shoots, seeds, rhizomes, flowers and other reproductive organs, leaves and other aerial parts. Methods for the isolation and purification of Free-B-Ring flavonoids are described in U.S. application Ser. No. 10/091,362, filed Mar. 1, 2002, entitled "Identification of Free-B-Ring Flavonoids as Potent Cox-2 Inhibitors," which is incorporated herein by reference in its entirety.

The flavans that can be used in accordance with the method of this invention include compounds illustrated by the general structure set forth above. The flavans of this invention are isolated from a plant or plants selected from the *Acacia* genus of plants. In a preferred embodiment, the plant is selected from the group consisting of *Acacia catechu* (*A. catechu*), *A. concinna*, *A. farnesiana*, *A. Senegal*, *A. speciosa*, *A. arabica*, *A. caesia*, *A. pennata*, *A. sinuata. A. mearnsii*, *A. picnantha*, *A. dealbata*, *A. auriculiformis*, *A. holoserecia* and *A. mangium*.

The flavans can be found in different parts of plants, including but not limited to stems, stem barks, trunks, trunk barks, twigs, tubers, roots, root barks, young shoots, seeds, rhizomes, flowers and other reproductive organs, leaves and other aerial parts. Methods for the isolation and purification of flavans are described in U.S. application Ser. No. 10/104,477, filed Mar. 22, 2002, entitled "Isolation of a Dual Cox-2 and 5-Lipoxygenase Inhibitor from *Acacia*," which is incorporated herein by reference in its entirety.

The present invention implements a strategy that combines a series of in vivo inflammation and toxicity studies as well as in vitro biochemical, cellular, and gene expression screens to identify active plant extracts that specifically inhibit COX and LOX enzymatic activity, impact mRNA gene expression and reduce inflammation. The methods used herein to identify active plant extracts that specifically inhibit COX and LOX are described in Examples 1 and 2, as well as in U.S. application Ser. No. 10/091,362, filed Mar. 1, 2002, entitled "Identification of Free-B-Ring Flavonoids as Potent Cox-2 Inhibitors;" U.S. application Ser. No. 10/104,477, filed Mar. 22, 2002, entitled "Isolation of a Dual Cox-2 and 5-Lipoxygenase Inhibitor from *Acacia*," and U.S. application Ser. No. 10/427,746, filed Apr. 30, 2003, entitled "Formulation With Dual Cox-2 And 5-Lipoxygenase Inhibitory Activity," each of which is incorporated herein by reference in its entirety.

Figure 6:
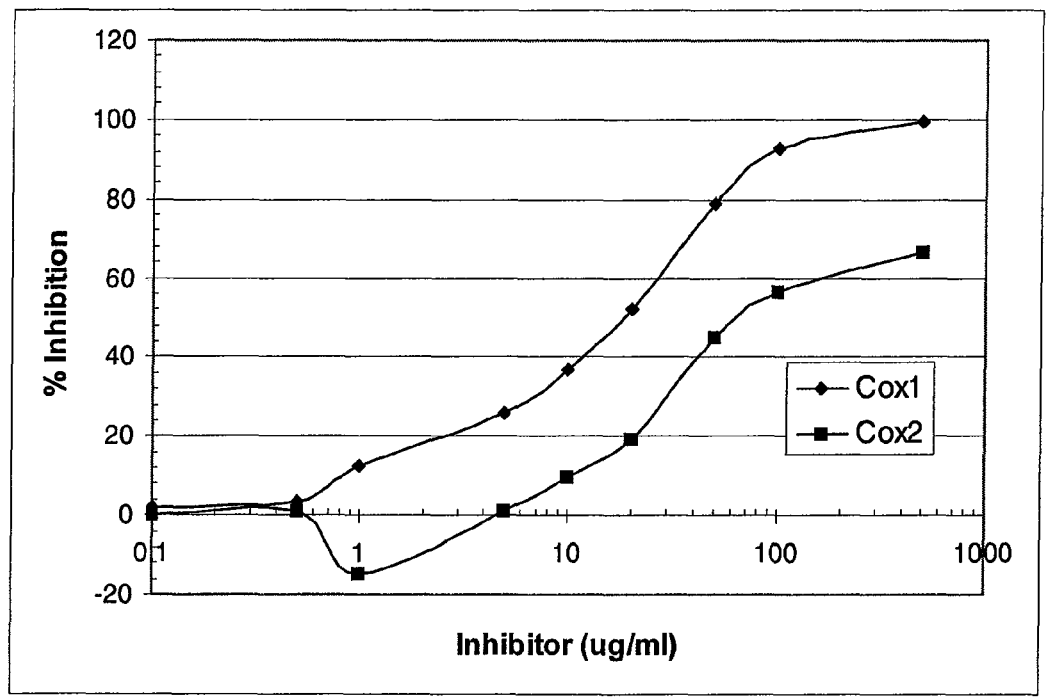
FIG. 6 depicts graphically a profile of the inhibition of COX-1 and COX-2 by a formulation produced by combining an extract of Free-B-Ring flavonoids isolated from the roots of *Scutellaria baicalensis* and an extract of flavans isolated from the bark of *Acacia catechu* in a ratio of 80:20. This composition of matter, referred to hereinafter as Soliprin™, was examined for its inhibition of the peroxidase activity of recombinant ovine COX-1 (♦) and ovine COX-2 (■). The data is presented as percent inhibition vs. inhibitor concentration (µg/mL). The $IC_{50}$ for COX-1 was calculated as 0.76 µg/mL/unit of enzyme and the $IC_{50}$ for COX-2 was calculated as 0.80 µg/mL/unit.
Figure 7:
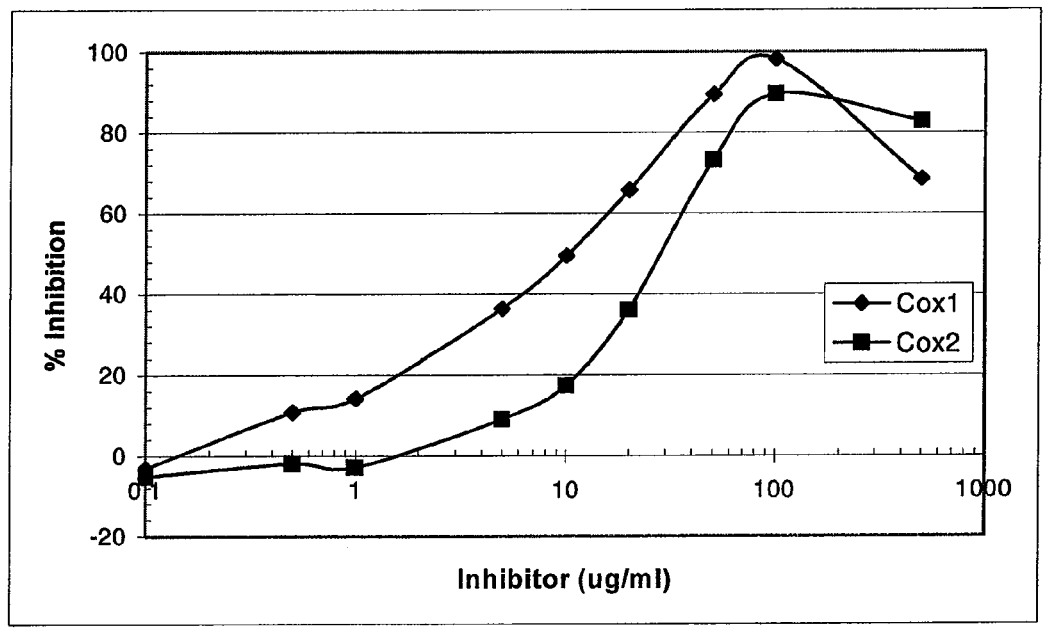
FIG. 7 depicts graphically a profile of the inhibition of COX-1 and COX-2 by a formulation produced by combining an extract of Free-B-Ring flavonoids isolated from the roots of *Scutellaria baicalensis* and an extract of flavans isolated from the bark of *Acacia catechu* in a ratio of about 50:50. The composition, Soliprin™, was examined for its inhibition of the peroxidase activity of recombinant ovine COX-1 (♦) and ovine COX-2 (■). The data is presented as percent inhibition vs. inhibitor concentration (µg/mL). The $IC_{50}$ for COX-1 was calculated as 0.38 µg/mL/unit of enzyme and the $IC_{50}$ for COX-2 was determined to be 0.84 µg/mL/unit.
Figure 8:
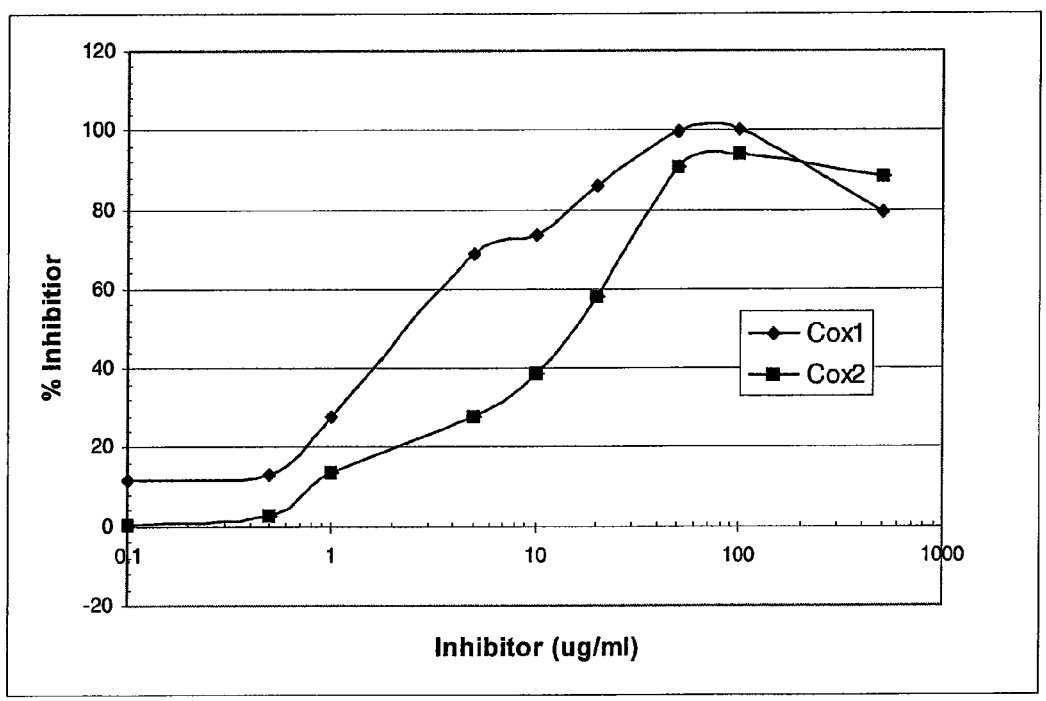
FIG. 8 depicts graphically a profile of the inhibition of COX-1 and COX-2 by a formulation produced by combining an extract of Free-B-Ring flavonoids isolated from the roots of *Scutellaria baicalensis* and an extract of flavans isolated from the bark of *Acacia catechu* in a ratio of about 20:80. The composition, Soliprin™, was examined for its inhibition of the peroxidase activity of recombinant ovine COX-1 (♦) and ovine COX-2 (■). The data is presented as percent inhibition vs. inhibitor concentration (µg/mL). The $IC_{50}$ of this composition for COX-1 was 0.18 µg/mL/unit of enzyme and the $IC_{50}$ for COX-2 was 0.41 µg/mL/unit.
Figure 9:
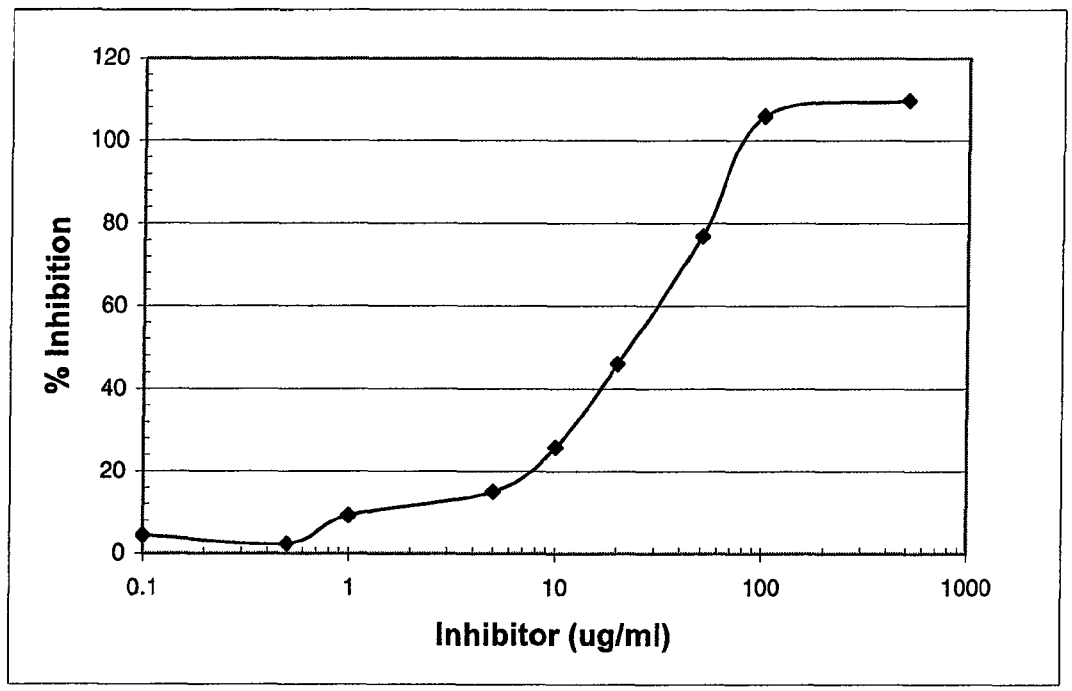
FIG. 9 depicts graphically a profile of the inhibition of 5-LO by the flavan extract from *Acacia catechu*. The composition was examined for its inhibition of recombinant potato 5-lipoxygenase activity (♦) as described in Example 4. The data is presented as percent inhibition of assays without inhibitor. The $IC_{50}$ for 5-LO was 1.38 µg/mL/unit of enzyme.
Figure 11:
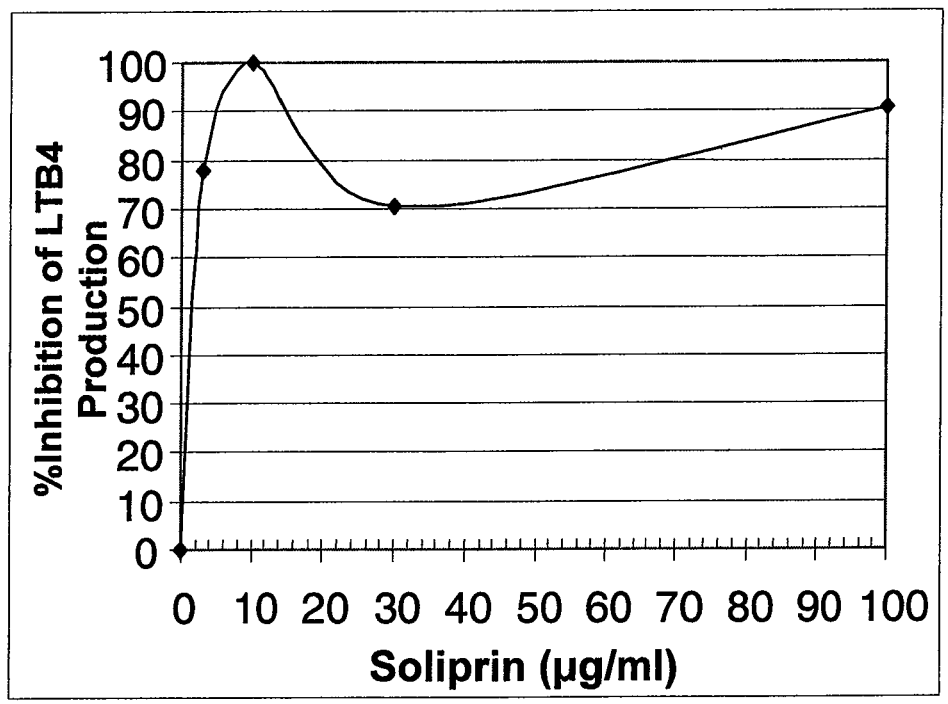
FIG. 11 depicts graphically the effect of increasing concentrations of Soliprin™ on the amount of LPS-induced newly synthesized $LTB_4$ (♦) as determined by ELISA in THP-1 or HT-29 cells (ATCC) as described in Example 10. The Soliprin™ was produced through the combination of standardized extracts of Free-B-Ring flavonoids isolated from the roots of *Scutellaria baicalensis* and flavans isolated from the bark of *Acacia catechu* in a ratio of 80:20. The activity of the Soliprin™ formulation is expressed as % inhibition of induced $LTB_4$ synthesis.
Figure 12:
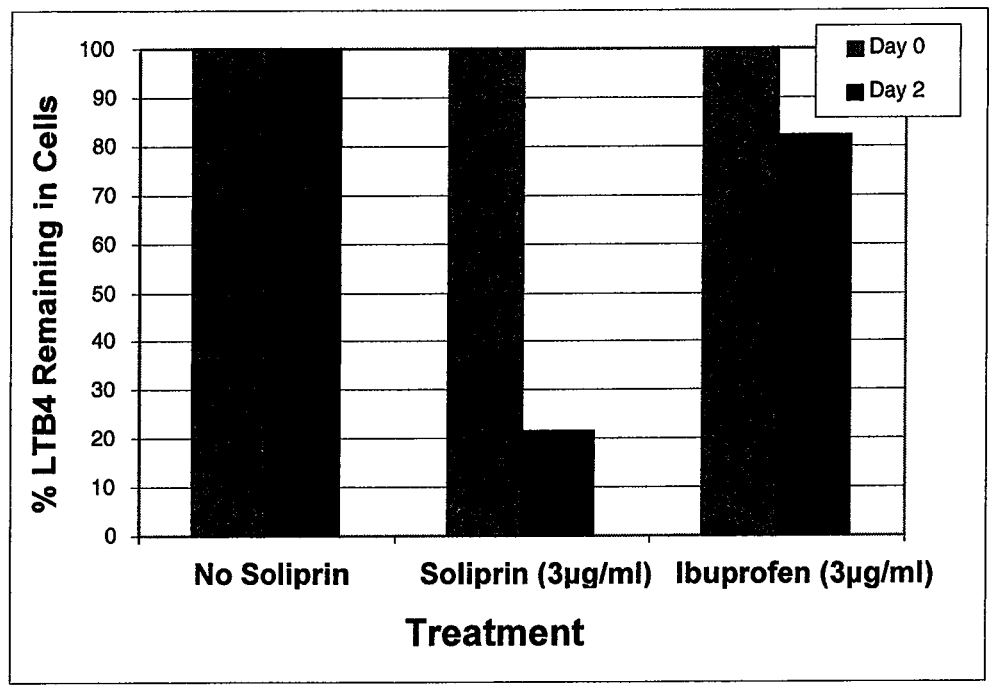
FIG. 12 compares the $LTB_4$ levels as determined by ELISA that remain in HT-29 cells after treatment with 3 µg/mL Soliprin™ in non-induced cells to treatment with 3 µg/mL ibuprofen as described in Example 10. The Soliprin™ formulation demonstrated 80% inhibition of LTB4 production in the HT-29 cells after two days of treatment.

The biochemical assay, used to measure inhibition of COX, relies on the protein's peroxidase activity in the presence of heme and arachidonic acid. This study which is described in Example 3, showed that the purified Free-B-Ring flavonoids, baicalin and baicalein isolated from *Scutellaria baicalensis* and the flavan extract isolated from *Acacia catechu*, and each individual standardized extract containing high concentrations of Free-B-Ring flavonoids and flavans inhibited COX activity (FIGS. 1-5). Additionally, compositions having different ratios of each of the individual standardized extracts (i.e., 80:20, 50:50 and 20:80 Free-B-Ring flavonoids:flavans), prepared as illustrated in Example 9, were all highly effective at inhibiting the COX activity in vitro (FIGS. 6-8). The inhibition of LOX activity by a flavan extract isolated from *Acacia catechu*, was assessed using a lipoxygenase screening assay in vitro as described in Example 4. The results are illustrated in FIG. 9. In addition, cell assays that targeted inhibition of compounds in the breakdown of arachidonic acid in the LOX pathway, namely leukotriene B4 were performed using a Soliprin™ sample as described in Example 10. The $LTB_4$ inhibition results by Soliprin™ are illustrated in FIGS. 11 and 12.

In vivo efficacy was demonstrated by the application of skin irritating substances, such as AA, to the ears and ankle joint of mice and measuring the reduction of swelling in mice treated with Soliprin™ as described in Example 11. The results are set forth in FIGS. 13 and 14. Finally, the efficacy of topical application of Soliprin™ formulation in preventing and treating UV induced skin erythema is illustrated in Example 12 and FIG. 15. In the study described in Example 12, Soliprin™ in a blend ratio of 80:20 as of Free-B-Ring flavonoids:flavans was dissolved in water and applied topically at two concentration to the skin of hairless mice both before and after UV exposure, respectively. The erythema scores of the hairless mice from four Soliprin™ groups, in both concentrations and regardless the applications time as before or after UV exposure, all showed much less redness in smaller skin areas as compared to severe and extended erythema in both the control group and the group that was treated with Sooth-A Cain.

Example 13 (Tables 11 and 12) describes a general method for the preparation of a Soliprin™ cream using pharmacologically, dermatologically and cosmetic acceptable excipients. For purposes of illustration this Example provides a detailed procedure for the preparation of both a 0.5 wt % and 1.5 wt % Soliprin™ cream. Finally, both of the Soliprin™ creams prepared as described in Example 13 were evaluated on human skin for potential irritation and induction of contact sensitization. A total of 97 and 101 subjects completed induction and challenge with the 0.5% and 1.5% Soliprin™ creams, respectively. Test results show that Soliprin™ creams at 0.5% and 1.5% concentration produced minimal irritation and did not elicit evidence of induced contact sensitization.

In summary, the present invention includes methods that are effective in simultaneously inhibiting both the COX and LOX enzymes. The method for the simultaneous dual inhibition of the COX and LOX pathways is comprised of administering a composition comprising a mixture of Free-B-Ring flavonoids and flavans synthesized and/or isolated from a single plant or multiple plants to a host in need thereof. The ratio of Free-B-Ring flavonoids to flavans in the composition can be in the range of 99:1 Free-B-Ring flavonoids:flavans to 1:99 of Free-B-Ring flavonoids:flavans. In specific embodiments of the present invention, the ratio of Free-B-Ring flavonoids to flavans is selected from the group consisting of approximately 90:10, 80:20, 70:30, 60:40, 50:50, 40:60, 30:70, 20:80 and 10:90. In a preferred embodiment of the invention, the ratio of Free-B-Ring flavonoids:flavans in the composition of matter is approximately 20:80. In a preferred embodiment, the Free-B-Ring flavonoids are isolated from a plant or plants in the *Scutellaria* genus of plants and flavans are isolated from a plant or plants in the *Acacia* genus of plants.

The present further includes methods for the prevention and treatment of COX and LOX mediated skin diseases and conditions. The method for preventing and treating COX and LOX mediated skin diseases and conditions is comprised of administering to a host in need thereof an effective amount of a composition comprising a mixture of Free-B-Ring flavonoids and flavans synthesized and/or isolated from a single plant or multiple plants together with a pharmaceutically acceptable carrier. The ratio of Free-B-Ring flavonoids to flavans can be in the range of 99:1 Free-B-Ring flavonoids:flavans to 1:99 of Free-B-Ring flavonoids:flavans. In specific embodiments of the present invention, the ratio of Free-B-Ring flavonoids to flavans is selected from the group consisting of approximately 90:10, 80:20, 70:30, 60:40, 50:50, 40:60, 30:70, 20:80 and 10:90. In a preferred embodiment of the invention, the ratio of Free-B-Ring flavonoids:flavans in the composition of matter is approximately 20:80. In a preferred embodiment, the Free-B-ring flavonoids are isolated from a plant or plants in the *Scutellaria* genus of plants and flavans are isolated from a plant or plants in the *Acacia* genus of plants.

Applicant believes that U.S. application Ser. No. 10/104,477, filed Mar. 22, 2002, entitled "Isolation of a Dual COX-2 and 5-Lipoxygenase Inhibitor from *Acacia*," is the first report of a composition of matter isolated from the *Acacia* genus of plants that demonstrates dual specificity for COX and LOX and that U.S. application Ser. No. 10/091,362, filed Mar. 1, 2002, entitled "Identification of Free-B-Ring Flavonoids as Potent COX-2 Inhibitors," is the first report of a correlation between Free-B-Ring flavonoid structure and COX inhibitory activity. These discoveries led to a novel blending of two classes of specific compounds—Free-B-Ring Flavonoids and flavans—to form a composition of matter, referred to herein as Soliprin™, which can be used for the prevention and treatment of COX and LOX mediated diseases and conditions, as described in U.S. application Ser. No. 10/427,746, filed Apr. 30, 2003, entitled "Formulation With Dual Cox-2 And 5-Lipoxygenase Inhibitory Activity." COX and LOX mediated diseases and conditions include, but are not limited to diseases and conditions of the skin including, but are not limited to sun burns, thermal burns, acne, topical wounds, minor inflammatory conditions caused by fungal, microbial and viral infections, vitilago, systemic lupus erythromatosus, psoriasis, carcinoma, melanoma, as well as other mammal skin cancers, skin damage resulting from exposure to UV radiation, chemicals, heat, wind and dry environments, wrinkles, saggy skin, lines and dark circles around the eyes, dermatitis and other allergy related conditions of the skin. Although not limited by theory, it is believed that the mechanism of action of this class of compounds is the direct dual inhibition of both COX and LOX enzymatic activity.

The present invention further includes therapeutic compositions comprising the therapeutic agents of the present invention including various formulations thereof. Methods for the preparation of these compositions, together with methods for the determination of their purity and specific composition are described in Examples 5-9 and FIG. 10.

In a preferred embodiment, the method of prevention and treatment of COX and LOX mediated skin related diseases and conditions according to this invention comprises administering topically to a host in need thereof a therapeutically effective amount of the formulated Free-B-Ring flavonoids and/or flavans isolated from a single source or multiple sources. The purity of the individual and/or a mixture of Free-B-Ring flavonoids and flavans includes, but is not limited to 0.01% to 100%, depending on the methodology used to obtain the compound(s). In a preferred embodiment, doses of the mixture of Free-B-Ring flavonoids and/or flavans containing that same are an efficacious, nontoxic quantity generally selected from the range of 0.001% to 100% based on total weight of the topical formulation. Persons skilled in the art using routine clinical testing are able to determine optimum doses for the particular ailment being treated.

The present invention includes evaluation of the different composition of Free-B-Ring flavonoids and flavan using enzymatic and in vivo anti-inflammation models to optimize the formulation and obtain the greatest potency as described below. The present invention provides a commercially viable process for the isolation, purification and combination of *Acacia* flavans with Free-B-Ring flavonoids to yield a composition of matter having desirable physiological activity. In addition to their use for the prevention and treatment of the above described diseases and conditions of the skin, the therapeutic compositions described herein can also be used to sooth sensitive skin and to provide smooth and youthful skin with improved elasticity, reduced and delayed aging, enhanced youthful appearance and texture, and increased flexibility, firmness, smoothness and suppleness.

The compositions of the present invention can be formulated as pharmaceutical compositions which include other components such as a pharmaceutically and/or cosmetically acceptable excipient, an adjuvant, and/or a carrier. For example, compositions of the present invention can be formulated in an excipient that the host to be treated can tolerate. An excipient is an inert substance used as a diluent or vehicle for a drug. Examples of such excipients include, but are not limited to water, buffers, saline, Ringer's solution, dextrose solution, mannitol, Hank's solution, preservatives and other aqueous physiologically balanced salt solutions. Nonaqueous vehicles, such as fixed oils, sesame oil, ethyl oleate, or triglycerides may also be used. Other useful formulations include suspensions containing viscosity enhancing agents, such as sodium carboxymethylcellulose, sorbitol, or dextran. Excipients can also contain minor amounts of additives, such as substances that enhance isotonicity and chemical stability. Examples of buffers include phosphate buffer, bicarbonate buffer, tris buffer, histidine, citrate, and glycine, or mixtures thereof, while examples of preservatives include, but are not limited to thimerosal, m- or o-cresol, formalin and benzyl alcohol. Standard formulations can either be liquid or solids, which can be taken up in a suitable liquid as a suspension or solution for administration. Thus, in a non-liquid formulation, the excipient can comprise dextrose, human serum albumin, preservatives, etc., to which sterile water or saline can be added prior to administration.

In one embodiment of the present invention, the composition can also include an adjuvant or a carrier. Adjuvants are typically substances that generally enhance the biological response of a mammal to a specific bioactive agent. Suitable adjuvants include, but are not limited to, Freund's adjuvant; other bacterial cell wall components; aluminum-based salts; calcium-based salts; silica; polynucleotides; toxoids; serum proteins; viral coat proteins; other bacterial-derived preparations; gamma interferon; block copolymer adjuvants, such as Hunter's Titermax adjuvant (Vaxcel™, Inc. Norcross, Ga.); Ribi adjuvants (available from Ribi ImmunoChem Research, Inc., Hamilton, Mont.); and saponins and their derivatives, such as Quil A (available from Superfos Biosector A/S, Denmark). Carriers are typically compounds that increase the half-life of a therapeutic composition in the treated host. Suitable carriers include, but are not limited to, polymeric controlled release formulations, biodegradable implants, liposomes, bacteria, viruses, oils, esters, and glycols.

In one embodiment, the composition is prepared as a controlled release formulation, which slowly releases the composition of the present invention into the host. As used herein, a controlled release formulation comprises a composition of the present invention in a controlled release vehicle. Suitable controlled release vehicles will be known to those skilled in the art. Preferred controlled release formulations are biodegradable (i.e., bioerodible).

The therapeutic agents of the instant invention are preferably administered topically by any suitable means, known to those of skill in the art for topically administering therapeutic compositions including, but not limited to as an ointment, gel, lotion, or cream base or as an emulsion, as a patch, dressing or mask, a nonsticking gauze, a bandage, a swab or a cloth wipe. Such topical application can be locally administered to any affected area, using any standard means known for topical administration. A therapeutic composition can be administered in a variety of unit dosage forms depending upon the method of administration. For particular modes of delivery, a therapeutic composition of the present invention can be formulated in an excipient of the present invention. A therapeutic reagent of the present invention can be administered to any host, preferably to mammals, and more preferably to humans. The particular mode of administration will depend on the condition to be treated.

In one embodiment, a suitable ointment is comprised of the desired concentration of the mixture of Free-B-Ring flavonoids and flavans, that is an efficacious, nontoxic quantity generally selected from the range of 0.001% to 100% based on total weight of the topical formulation, from 65 to 100% (preferably 75 to 96%) of white soft paraffin, from 0 to 15% of liquid paraffin, and from 0 to 7% (preferably 3 to 7%) of lanolin or a derivative of synthetic equivalent thereof. In another embodiment the ointment may comprise a polyethylene—liquid paraffin matrix.

In one embodiment, a suitable cream is comprised of an emulsifying system together with the desired concentration of the mixture of Free-B-Ring flavonoids and flavans as provided above. The emulsifying system is preferably comprised of from 2 to 10% of polyoxyethylene alcohols (e.g. the mixture available under the trademark Cetomacrogol™1000), from 10 to 25% of stearyl alcohol, from 20 to 60% of liquid paraffin, and from 10 to 65% of water; together with one or more preservatives, for example from 0.1 to 1% of N,N"-methylenebis[N'-[3-(hydroxymethyl)-2,5-dioxo-4-imidazolidinyl]urea] (available under the name Imidurea USNF), from 0.1 to 1% of alkyl 4-hydroxybenzoates (for example the mixture available from Nipa Laboratories under the trade mark Nipastat), from 0.01 to 0.1% of sodium butyl 4-hydroxybenzoate (available from Nipa Laboratories under the trade mark Nipabutyl sodium), and from 0.1 to 2% of phenoxyethanol. Example 13 describes the formulation of two different concentrations of the composition of this invention as a cream and Example 14 describes a study undertaken to evaluate the cream for irritation and sensitization of the skin. From this study it was determined that Soliprin™ is a safe composition that can be applied topically at an efficacious concentration without causing irritation or sensitization of the skin.

In one embodiment, a suitable gel is comprised of a semi-solid system in which a liquid phase is constrained within a three dimensional polymeric matrix with a high degree of cross-linking. The liquid phase may be comprised of water, together with the desired amount of the mixture of Free-B-Ring flavonoids and flavans, from 0 to 20% of water-miscible additives, for example glycerol, polyethylene glycol, or propylene glycol, and from 0.1 to 10%, preferably from 0.5 to 2%, of a thickening agent, which may be a natural product, for example tragacanth, pectin, carrageen, agar and alginic acid, or a synthetic or semi-synthetic compound, for example methylcellulose and carboxypolymethylene (carbopol); together with one or more preservatives, for example from 0.1 to 2% of methyl 4-hydroxybenzoate (methyl paraben) or phenoxyethanol-differential. Another suitable base, is comprised of the desired amount of the mixture of Free-B-Ring flavonoids and flavans, together with from 70 to 90% of polyethylene glycol (for example, polyethylene glycol ointment containing 40% of polyethylene glycol 3350 and 60% of polyethylene glycol 400, prepared in accordance with the U.S. National Formulary (USNF)), from 5 to 20% of water, from 0.02 to 0.25% of an anti-oxidant (for example butylated hydroxytoluene), and from 0.005 to 0.1% of a chelating agent (for example ethylenediamine tetraacetic acid (EDTA)).

The term soft paraffin as used above encompasses the cream or ointment bases white soft paraffin and yellow soft paraffin. The term lanolin encompasses native wool fat and purified wool fat. Derivatives of lanolin include in particular lanolins which have been chemically modified in order to alter their physical or chemical properties and synthetic equivalents of lanolin include in particular synthetic or semi-synthetic compounds and mixtures which are known and used in the pharmaceutical and cosmetic arts as alternatives to lanolin and may, for example, be referred to as lanolin substitutes.

One suitable synthetic equivalent of lanolin that may be used is the material available under the trademark Softisan™ known as Softisan 649. Softisan 649, available from Dynamit Nobel Aktiengesellschaft, is a glycerine ester of natural vegetable fatty acids, of isostearic acid and of adipic acid; its properties are discussed by H. Hermsdorf in Fette, Seifen, Anstrichmittel, Issue No. 84, No. 3 (1982), pp. 3-6.

The other substances mentioned hereinabove as constituents of suitable ointment or cream bases and their properties are discussed in standard reference works, for example pharmacopoeia. Cetomacrogol 1000 has the formula $CH_3(CH_2)_m(OCH_2CH_2)_nOH$, wherein m may be 15 or 17 and n may be 20 to 24. Butylated hydroxytoluene is 2,6-di-tert-butyl-p-cresol. Nipastat is a mixture of methyl, ethyl, propyl and butyl 4-hydroxybenzoates.

The compositions of the invention may be produced by conventional pharmaceutical techniques. Thus the aforementioned compositions, for example, may conveniently be prepared by mixing together at an elevated temperature, preferably 60-70° C., the soft paraffin, liquid paraffin if present, and lanolin or derivative or synthetic equivalent thereof. The mixture may then be cooled to room temperature, and, after addition of the hydrated crystalline calcium salt of mupirocin, together with the corticosteroid and any other ingredients, stirred to ensure adequate dispersion.

Regardless of the manner of administration, the specific dose is calculated according to the approximate body weight of the host. Further refinement of the calculations necessary to determine the appropriate dosage for treatment involving each of the above mentioned formulations is routinely made by those of ordinary skill in the art and is within the scope of tasks routinely performed by them without undue experimentation, especially in light of the dosage information and assays disclosed herein. These dosages may be ascertained through use of the established assays for determining dosages utilized in conjunction with appropriate dose-response data.

It should be noted that the invention described herein may be used for veterinary as well as human applications and that the term "host" should not be construed in a limiting manner. In the case of veterinary applications, the dosage ranges can be determined as described above, taking into account the body weight of the animal.

The compositions of this invention can be administered by any method known to one of ordinary skill in the art. The modes of administration include, but are not limited to, enteral (oral) administration, parenteral (intravenous, subcutaneous, and intramuscular) administration and topical application. The method of treatment according to this invention comprises administering internally or topically to a patient in need thereof a therapeutically effective amount of a mixture of Free-B-Ring flavonoids and flavans synthesized and/or isolated from a single plant or multiple plants. In a preferred embodiment the composition is administered topically.

The following examples are provided for illustrative purposes only and are not intended to limit the scope of the invention.

EXAMPLES

Example 1

Preparation of Organic and Aqueous Extracts from *Acacia* and *Scutellaria* Plants Plant material from *Acacia catechu* (L) Willd. barks, *Scutellaria orthocalyx* roots, *Scutellaria baicalensis* roots or *Scutellaria lateriflora* whole plant was ground to a particle size of no larger than 2 mm. Dried ground plant material (60 g) was then transferred to an Erlenmeyer flask and methanol:dichloromethane (1:1) (600 mL) was added. The mixture was shaken for one hour, filtered and the biomass was extracted again with methanol:dichloromethane (1:1) (600 mL). The organic extracts were combined and evaporated under vacuum to provide the organic extract (see Table 1 below). After organic extraction, the biomass was air dried and extracted once with ultra pure water (600 mL). The aqueous solution was filtered and freeze-dried to provide the aqueous extract (see Table 1 below).

TABLE 1

Yield of Organic and Aqueous Extracts of *Acacia* and *Scutellaria* Species

| Plant Source | Amount | Organic Extract | Aqueous Extract |
|---|---|---|---|
| *Acacia catechu* barks | 60 g | 27.2 g | 10.8 g |
| *Scutellaria orthocalyx* roots | 60 g | 4.04 g | 8.95 g |
| *Scutellaria baicalensis* roots | 60 g | 9.18 g | 7.18 g |
| *Scutellaria lateriflora* (whole plant) | 60 g | 6.54 g | 4.08 g |

Example 2

Inhibition of COX-2 and COX-1 Peroxidase Activity by Plant Extracts from *Acacia catechu*, Various *Scutellaria* Species and Other Plants The bioassay directed screening process for the identification of specific COX-2 inhibitors was designed to assay the peroxidase activity of the enzyme as described below.

Peroxidase Assay.

The assay to detect inhibitors of COX-2 was modified for a high throughput platform (Raz). Briefly, recombinant ovine COX-2 (Cayman) in peroxidase buffer (100 mM TBS, 5 mM EDTA, 1 µM Heme, 1 mg epinephrine, 0.094% phenol) was incubated with extract (1:500 dilution) for 15 minutes. Quantablu (Pierce) substrate was added and allowed to develop for 45 minutes at 25° C. Luminescence was then read using a Wallac Victor 2 plate reader. The results are presented in Table 2.

Table 2 sets forth the inhibition of enzyme by the organic and aqueous extracts obtained from five plant species, including the bark of *Acacia catechu*, roots of two *Scutellaria* species and extracts from three other plant species, which are comprised of structurally similar Free-B-Ring flavonoids. Data is presented as the percent of peroxidase activity relative to the recombinant ovine COX-2 enzyme and substrate alone. The percent inhibition by the organic extract ranged from 30% to 90%.

TABLE 2

Inhibition of COX-2 Peroxidase Activity by Various Species

| Plant Source | Inhibition of COX-2 by organic extract | Inhibition of COX-2 by aqueous extract |
|---|---|---|
| *Acacia catechu* (bark) | 75% | 30% |
| *Scutellaria orthocalyx* (root) | 55% | 77% |
| *Scutellaria baicalensis* (root) | 75% | 0% |
| *Desmodium sambuense* (whole plant) | 55% | 39% |
| *Eucaluptus globulus* (leaf) | 30% | 10% |
| *Murica nana* (leaf) | 90% | 0% |

Comparison of the relative inhibition of the COX-1 and COX-2 isoforms requires the generation of $IC_{50}$ values for each of these enzymes. The $IC_{50}$ is defined as the concentration at which 50% inhibition of enzyme activity in relation to the control is achieved by a particular inhibitor. In these experiments, $IC_{50}$ values were found to range from 6 to 50 µg/mL and 7 to 80 µg/mL for the COX-2 and COX-1 enzymes, respectively, as set forth in Table 3. Comparison of the $IC_{50}$ values of COX-2 and COX-1 demonstrates the specificity of the organic extracts from various plants for each of these enzymes. The organic extract of *Scutellaria lateriflora* for example, shows preferential inhibition of COX-2 over COX-1 with $IC_{50}$ values of 30 and 80 µg/mL, respectively. While some extracts demonstrate preferential inhibition of COX-2, others do not. Examination of the HTP fractions and purified compounds from these fractions is necessary to determine the true specificity of inhibition for these extracts and compounds.

TABLE 3

$IC_{50}$ Values of Organic Extracts for Human and Ovine COX-2 and COX-1

| Plant Source | $IC_{50}$ Human COX-2 (µg/mL) | $IC_{50}$ Ovine COX-2 (µg/mL) | $IC_{50}$ Ovine COX-1 (µg/mL) |
|---|---|---|---|
| *Acacia catechu* (bark) | 3 | 6.25 | 2.5 |
| *Scutellaria orthocalyx* (root) | Not done | 10 | 10 |
| *Scutellaria baicalensis* (root) | 30 | 20 | 20 |
| *Scutellaria lateriflora* (whole plant) | 20 | 30 | 80 |
| *Eucaluptus globulus* (leaf) | Not done | 50 | 50 |
| *Murica nana* (leaf) | 5 | 6 | 7 |

Example 3

Inhibition of COX-1 and COX-2 Peroxidase Activity

In order to screen for compounds that inhibited the COX-1 and COX-2 activities, a high throughput, in vitro assay was developed that utilized the inhibition of the peroxidase activity of both enzymes. (Needleman et al. (1986) Annu Rev Biochem. 55:69). Briefly, the composition or compound being examined was titrated against a fixed amount of COX-1 and COX-2 enzymes. A cleavable, peroxide chromophore was included in the assay to visualize the peroxidase activity of each enzyme in presence of arachidonic acid as a cofactor. Typically, assays were performed in a 96-well format. Each inhibitor, taken from a 10 mg/mL stock solution in 100% DMSO, was tested in triplicate at room temperature using the following range of concentrations: 0, 0.1, 1, 5, 10, 20, 50, 100, and 500 µg/mL. To each well, 150 µL of 100 mM Tris-HCl, pH 7.5 was added along with 10 µL of 22 µM Hematin diluted in tris buffer, 10 µL of inhibitor diluted in DMSO and 25 units of either the COX-1 or COX-2 enzyme. The components were mixed for 10 seconds on a rotating platform, followed by the addition of 20 µL of 2 mM N,N,N'N'-tetramethyl-p-phenylenediamine dihydrochloride (TMPD) and 20 µL of 1.1 mM arachidonic acid to initiate the reaction. The plate was shaken for 10 seconds and then incubated 5 minutes before reading the absorbance at 570 nm. The inhibitor concentration vs. % inhibition was plotted and the $IC_{50}$ determined by taking the half-maximal point along the isotherm and intersecting the concentration on the X-axis. The $IC_{50}$ was then normalized to the number of enzyme units in the assay. The results are summarized in Table 4.

TABLE 4

Inhibition of COX Enzyme Activity by Purified Free-B-Ring Flavonoids

| Free-B-Ring Flavonoids | Inhibition of COX-1 | Inhibition of COX-2 |
| --- | --- | --- |
| Baicalein | 107% | 109% |
| 5,6-Dihydroxy-7-methoxyflavone | 75% | 59% |
| 7,8-Dihydroxyflavone | 74% | 63% |
| Baicalin | 95% | 97% |
| Wogonin | 16% | 12% |

Figure 2:
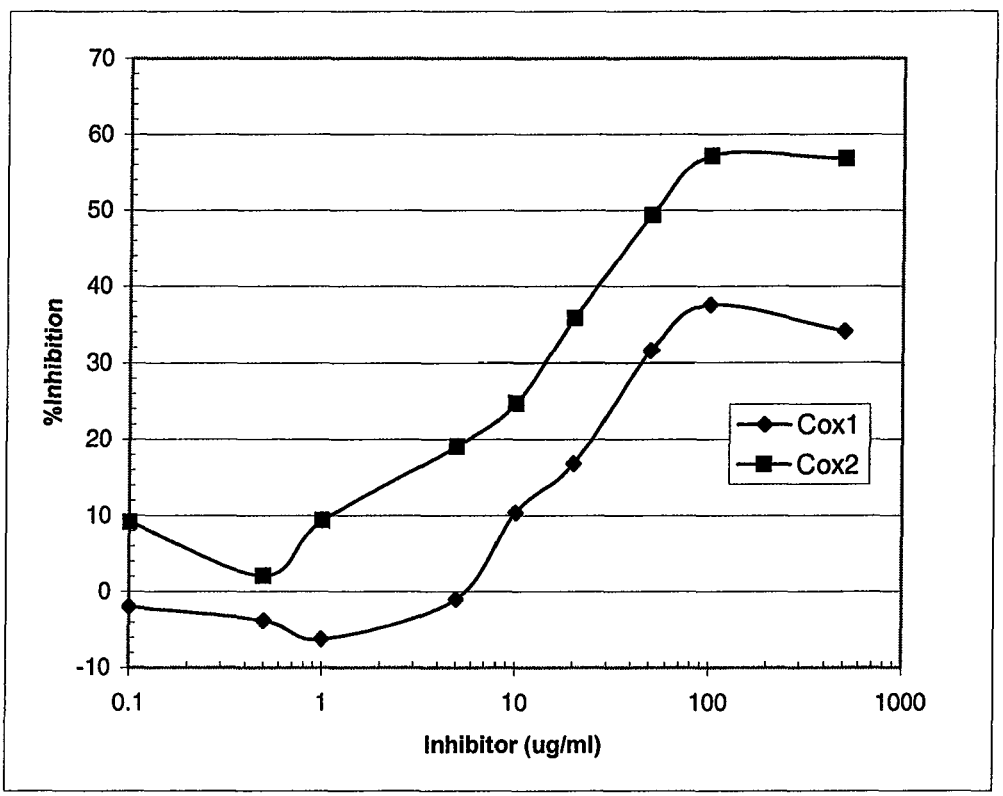
FIG. 2 depicts graphically a profile of the inhibition of COX-1 and COX-2 by the purified component baicalin which was isolated from *Scutellaria baicalensis*. The compound was examined for its inhibition of the peroxidase activity of recombinant ovine COX-1 (♦) and ovine COX-2 (■). The data is presented as percent inhibition vs. inhibitor concentration (µg/mL). The $IC_{50}$ for COX-1 was determined to be 0.44 µg/mL/unit of enzyme and the $IC_{50}$ for COX-2 was determined to be 0.28 µg/mL/unit.
Figure 3:
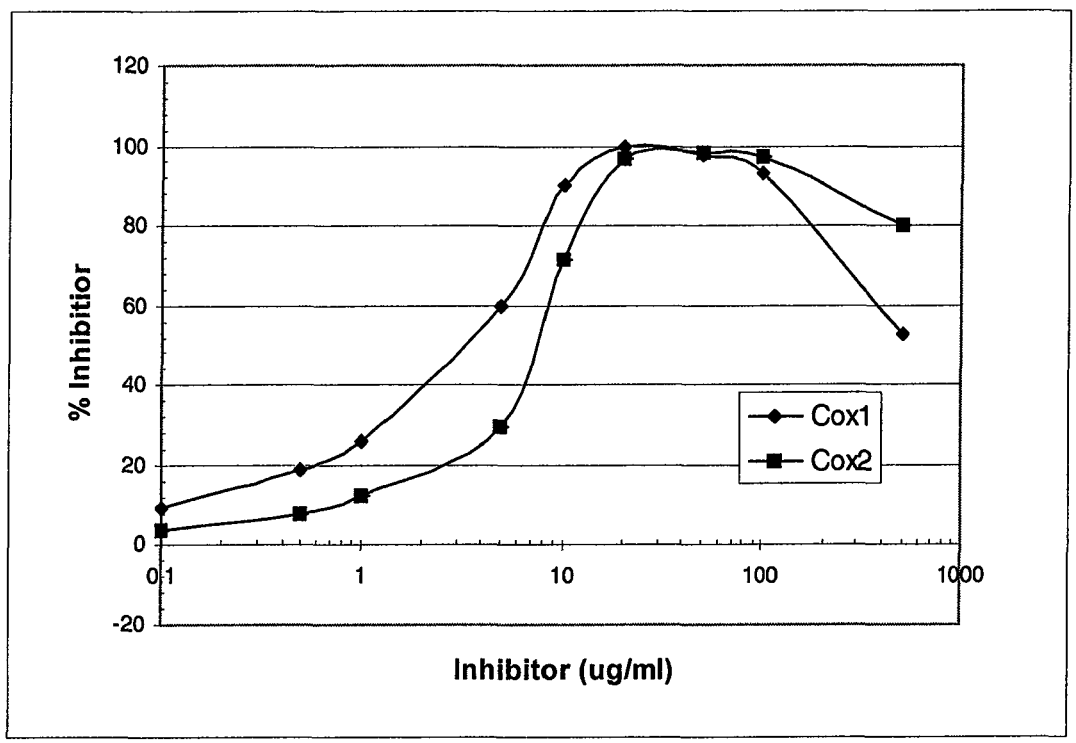
FIG. 3 depicts graphically a profile of the inhibition of COX-1 and COX-2 by the purified component baicalein isolated from *Scutellaria baicalensis*. The compound was examined for its inhibition of the peroxidase activity of recombinant ovine COX-1 (♦) and ovine COX-2 (■). The data is presented as percent inhibition vs. inhibitor concentration (µg/mL). The $IC_{50}$ for COX-1 was determined to be 0.18 µg/mL/unit of enzyme and the $IC_{50}$ for COX-2 was determined to be 0.28 µg/mL/unit.
Figure 4:
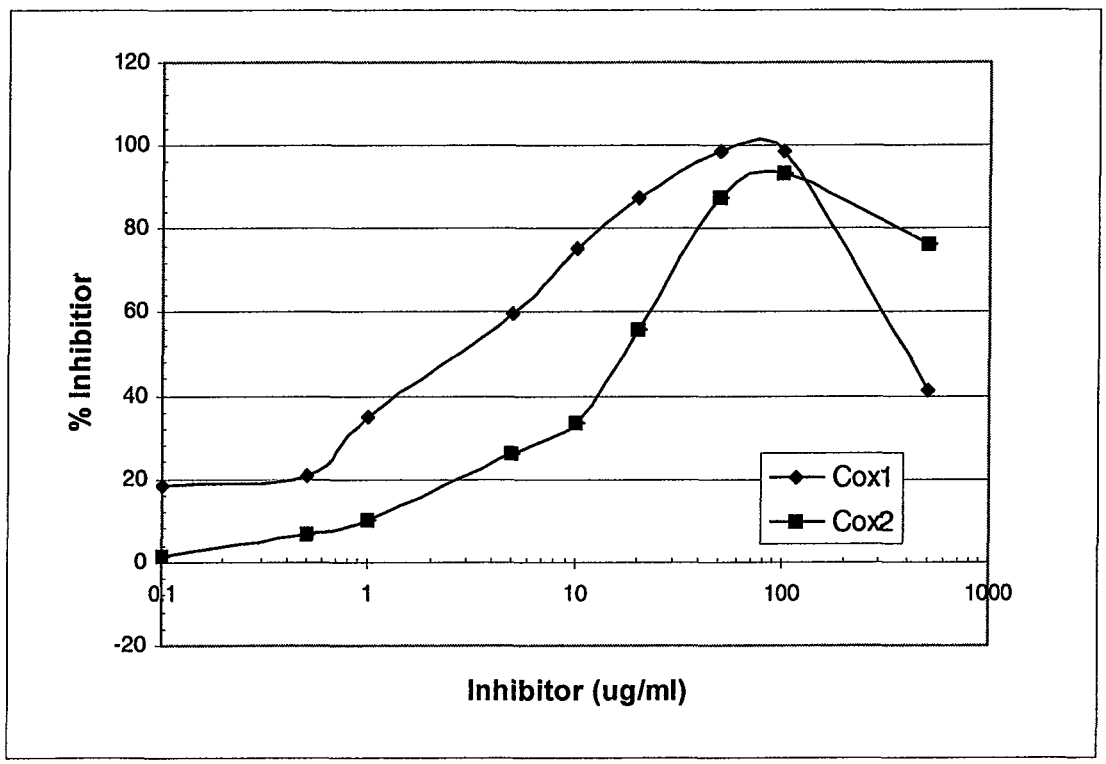
FIG. 4 depicts graphically a profile of the inhibition of COX-1 and COX-2 by a standardized flavan extract containing 50% total flavans which was isolated from *Acacia catechu*. The extract was examined for its inhibition of the peroxidase activity of recombinant ovine COX-1 (♦) and ovine COX-2 (■). The data is presented as percent inhibition vs. inhibitor concentration (µg/mL). The $IC_{50}$ for COX-1 was calculated as 0.17 µg/mL/unit of enzyme and the $IC_{50}$ for COX-2 was calculated as 0.41 µg/mL/unit.
Figure 5:
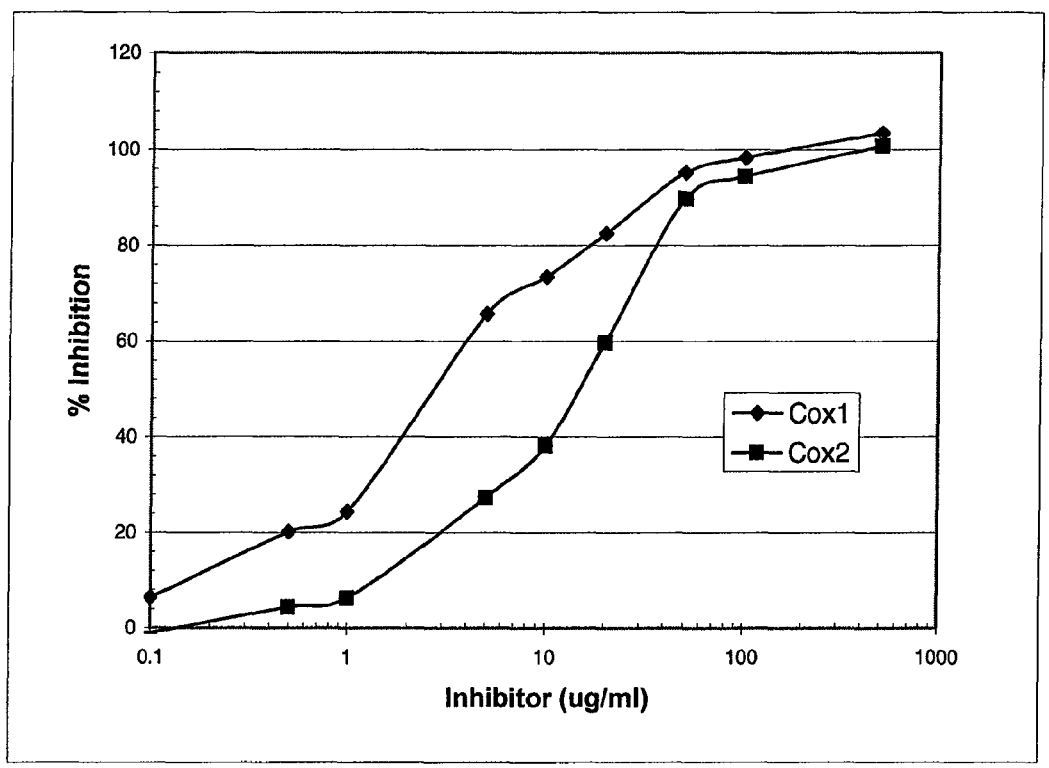
FIG. 5 depicts graphically a profile of the inhibition of COX-1 and COX-2 by the a composition of matter comprised of greater than 90% flavans isolated from *Acacia catechu*. The composition was examined for its inhibition of the peroxidase activity of recombinant ovine COX-1 (♦) and ovine COX-2 (■). The data is presented as percent inhibition vs. inhibitor concentration (µg/mL). The $IC_{50}$ for COX-1 was calculated as 0.11 µg/mL/unit of enzyme and the $IC_{50}$ for COX-2 was calculated as 0.42 µg/mL/unit.

The dose responses and $IC_{50}$ values for a standardized Free-B-Ring flavonoid extract, baicalin, and baicalein isolated from the roots of *Scutellaria baicalensis* are provided in FIGS. 1, 2 and 3, respectively. The dose responses and $IC_{50}$ values for two standardized flavan extract (50% and >90% flavans, respectively) isolated from the heartwood of *Acacia catechu* are provided in FIGS. 4 and 5, respectively. The dose responses and $IC_{50}$ values for three formulations of Free-B-Ring flavonoids and flavans of varying composition are provided in FIG. 6 (80:20 blending), FIG. 7 (50:50 blending) and FIG. 8 (20:80 blending), respectively.

Example 4

Inhibition of 5-Lipoxygenase by Catechin Isolated from *Acacia catechu*

One of the most important pathways involved in the inflammatory response is produced by non-heme, iron-containing lipoxygenases (5-LO, 12-LO, and 15-LO), which catalyze the addition of molecular oxygen onto fatty acids such as AA (AA) to produce the hydroperoxides 5-, 12- and 15-HPETE, which are then converted to leukotrienes. There were early indications that the flavan extract from *A. catechu* may provide some degree of LOX inhibition, thereby preventing the formation of 5-HPETE. A Lipoxygenase Inhibitor Screening Assay Kit (Cayman Chemical, Inc., Cat #760700) was used to assess whether an extract isolated from *A. catechu* containing >90% flavans directly inhibited LOX in vitro. The 15-LO from soybeans normally used in the kit was replaced with potato LOX, after a buffer change from phosphate to a tris-based buffer using microfiltration was performed. This assay detects the formation of hydroperoxides through an oxygen sensing chromagen. Briefly, the assay was performed in triplicate by adding 90 μL of 0.17 units/μL potato 5-LO, 20 μL of 1.1 mM AA, 100 μL of oxygen-sensing chromagen and 10 μL of purified flavan inhibitor to final concentrations ranging from 0 to 500 μg/mL. The $IC_{50}$ for 5-LO inhibition from this composition was determined to be 1.38 μg/mL/unit of enzyme. The results are set forth in FIG. 9.

Example 5

HPLC Quantification of Free-B-Ring Flavonoids in Active Extracts Isolated from *Scutellaria orthocalyx* (Roots), *Scutellaria baicalensis* (Roots) and *Oroxylum indicum* (Seeds)

The presence and quantity of Free-B-Ring flavonoids in five active extracts isolated from three different plant species as described in Examples 1 and 2 were determined by HPLC and the results are set forth in the Table 5, below. The Free-B-Ring flavonoids were quantitatively analyzed by HPLC on a Luna C-18 column (250×4.5 mm, 5 μm) using a 1% phosphoric acid and acetonitrile gradient from 80% to 20% in 22 minutes. The Free-B-Ring flavonoids were detected using a UV detector at 254 nm and identified based on retention time by comparison with baicalin, baicalein and other Free-B-Ring flavonoid standards.

TABLE 5

Free-B-Ring Flavonoid Content in Active Plant Extracts

| Active Extracts | Weight of Extract | % Extractible from BioMass | Total amount of Free-B-Ring Flavonoids | % Free-B-Ring Flavonoids in Extract |
| --- | --- | --- | --- | --- |
| *S. orthocalyx* (aqueous extract) | 8.95 g | 14.9% | 0.2 mg | 0.6% |
| *S. orthocalyx* (organic extract) | 3.43 g | 5.7% | 1.95 mg | 6.4% |
| *S. baicalensis* (aqueous extract) | 7.18 g | 12.0% | 0.03 mg | 0.07% |
| *S. baicalensis* (organic extract) | 9.18 g | 15.3% | 20.3 mg | 35.5% |
| *Oroxylum indicum* (organic extract) | 6.58 g | 11.0% | 0.4 mg | 2.2% |

Example 6

HPLC Quantification of Active Extracts from *Acacia catechu*

The flavans in the organic and aqueous extracts isolated from *Acacia catechu* as illustrated in Examples 1 and 2 were quantified by HPLC using a PhotoDiode Array detector (HPLC/PDA) and a Luna C18 column (250 mm×4.6 mm). The flavans were eluted from the column using an acetonitrile gradient from 10% to 30% ACN over a period of 20 minutes, followed by 60% ACN for five minutes. The results are set forth in Table 6. The flavans were quantified based on retention time and PDA data using catechin and epicatechin as standards. The retention times for the two major flavans were 12.73 minutes and 15.76 minutes, respectively.

TABLE 6

Free-B-Ring Flavonoid Content in Active Plant Extracts

| Active Extracts from bark of *A. catechu* | Weight of Extract | % Extractible from BioMass | % Flavans in Extract |
| --- | --- | --- | --- |
| Aqueous Extract | 10.8 g | 18.0% | 0.998% |
| Organic Extract | 27.2 g | 45.3% | 30.37% |

Example 7

Preparation of a Standardized Extract from *Acacia catechu*

*Acacia catechu* (500 mg of ground root) was extracted twice with 25 mL (2×25 mL) of the following solvent systems. (1) 100% water, (2) 80:20 water:methanol, (3) 60:40 water:methanol, (4) 40:60 water:methanol, (5) 20:80 water:methanol, (6) 100% methanol, (7) 80:20 methanol:THF, (8) 60:40 methanol:THF. The two extracts from each individual extraction were combined concentrated and dried under low vacuum. The identification of the chemical components in each extract was achieved by HPLC using a PhotoDiode Array detector (HPLC/PDA) and a 250 mm×4.6 mm C18 column. The chemical components were quantified based on retention time and PDA data using catechin and epicatechin as standards. The results are set forth in Table 7. As shown in Table 7, the flavan extract generated from solvent extraction with 80% methanol/water provided the highest concentration of flavan components.

TABLE 7

Solvents for Generating Standardized Flavan Extracts from *Acacia catechu*

| Extraction Solvent | Weight of Extract | % Extractible from BioMass | Total amount of Catechins | % Catechins in Extract |
|---|---|---|---|---|
| 100% water | 292.8 mg | 58.56% | 13 mg | 12.02% |
| water:methanol (80:20) | 282.9 mg | 56.58% | 13 mg | 11.19% |
| water:methanol (60:40) | 287.6 mg | 57.52% | 15 mg | 13.54% |
| water:methanol (40:60) | 264.8 mg | 52.96% | 19 mg | 13.70% |
| water:methanol (20:80) | 222.8 mg | 44.56% | 15 mg | 14.83% |
| 100% methanol | 215.0 mg | 43.00% | 15 mg | 12.73% |
| methanol:THF (80:20) | 264.4 mg | 52.88% | 11 mg | 8.81% |
| methanol:THF (60:40) | 259.9 mg | 51.98% | 15 mg | 9.05% |

Higher purity material can be obtained by recrystallization of extracts having a catechin content of between 8%-15% using an alcohol/water and/or aqueous solvents as the recrystallization solvent. It may be necessary to decolorize prior to recrystallization by adding active charcoal or other decolorization agent to a heated saturated solution of the extract. The high purity catechins then crystallized upon cooling of the heated saturated solution. The crystals were then filtered to remove solvent, dried and ground into a fine powder. Recrystallization can be repeated as necessary to achieve a the desired level of purity (60%-100% of catechin flavans).

Example 8

Preparation of Standardized Free-B-Ring Flavonoid Extracts from Various *Scutellaria* Species

*Scutellaria orthocalyx* (500 mg of ground root) was extracted twice with 25 mL of the following solvent systems. (1) 100% water, (2) 80:20 water:methanol, (3) 60:40 water: methanol, (4) 40:60 water:methanol, (5) 20:80 water:methanol, (6) 100% methanol, (7) 80:20 methanol:THF, (8) 60:40 methanol:THF. The extracts were combined, concentrated and dried under low vacuum. Identification of chemical components in each extract was performed by HPLC using a PhotoDiode Array detector (HPLC/PDA) and a 250 mm×4.6 mm C18 column. The chemical components were quantified based on retention time and PDA data using baicalein, baicalin, scutellarein, and wogonin as standards. The results are set forth in Table 8.

TABLE 8

Quantification of Free-B-Ring Flavonoids Extracted from *Scutellaria orthocalyx*

| Extraction Solvent | Weight of Extract | % Extractible from BioMass | Total amount of Flavonoids | % Flavonoids in Extract |
|---|---|---|---|---|
| 100% water | 96 mg | 19.2% | 0.02 mg | 0.20% |
| Water:methanol (80:20) | 138.3 mg | 27.7% | 0.38 mg | 0.38% |
| Water:methanol (60:40) | 169.5 mg | 33.9% | 0.78 mg | 8.39% |
| Water:methanol (40:60) | 142.2 mg | 28.4% | 1.14 mg | 11.26% |
| Water:methanol (20:80) | 104.5 mg | 20.9% | 0.94 mg | 7.99% |
| 100% methanol | 57.5 mg | 11.5% | 0.99 mg | 10.42% |
| methanol:THF (80:20) | 59.6 mg | 11.9% | 0.89 mg | 8.76% |
| methanol:THF (60:40) | 58.8 mg | 11.8% | 1.10 mg | 10.71% |

*Scutellaria baicalensis* (1000 mg of ground root) was extracted twice using 50 mL of a mixture of methanol and water as follows: (1) 100% water, (2) 70:30 water:methanol, (3) 50:50 water:methanol, (4) 30:70 water:methanol, (5) 100% methanol. The extracts were combined, concentrated and dried under low vacuum. Identification of the chemical components was performed by HPLC using a PhotoDiode Array detector (HPLC/PDA), and a 250 mm×4.6 mm C18 column. The chemical components in each extract were quantified based on retention time and PDA data using baicalein, baicalin, scutellarein, and wogonin standards. The results are set forth in Table 9.

TABLE 9

Quantification of Free-B-Ring Flavonoids Extracted from *Scutellaria baicalensis*

| Extraction Solvent | Weight of Extract | % Extractible from BioMass | Total amount of Flavonoids | % Flavonoids in Extract |
|---|---|---|---|---|
| 100% water | 277.5 mg | 27.8% | 1 mg | 0.09% |
| Water:methanol (70:30) | 338.6 mg | 33.9% | 1.19 mg | 11.48% |
| Water:methanol (50:50) | 304.3 mg | 30.4% | 1.99 mg | 18.93% |
| Water:methanol (30:70) | 293.9 mg | 29.4% | 2.29 mg | 19.61% |
| 100% methanol | 204.2 mg | 20.4% | 2.73 mg | 24.51% |

Higher purity Free-B-Ring flavonoids can be obtained by recrystallization of extracts having a Free-B-Ring flavonoid content of between 8-15% using alcohol/water as a recrystallization solvent. It may be necessary to decolorize prior to recrystallization by adding active charcoal or other decolorization agent to a heated saturated solution of the extract. The Free-B-Ring flavonoids crystallized upon cooling. The crystals were filtered, dried and ground into a fine powder. Recrystallization can be repeated as necessary to achieve a the desired level of purity (60%-100% of Free-B-Ring flavonoids).

Example 9

Preparation of a Formulation with a Standardized Free-B-Ring Flavonoid Extract from the Roots of *Scutellaria baicalensis* and a Standardized Flavan Extract from the Bark of *Acacia catechu*

A novel composition of matter, referred to herein as Soliprin™ was formulated using two standardized extracts isolated from *Acacia* and *Scutellaria*, respectively, together with one or more excipients. A general example for preparing such a composition is set forth below. The *Acacia* extract used in this example contained >80% total flavans, as catechin and epicatechin, and the *Scutellaria* extract contained >80% Free-B-Ring flavonoids, which was primarily baicalin. The *Scutellaria* extract also contained other minor amounts of Free-B-Ring flavonoids as set forth in Table 11. One or more excipients/preservatives was also added to the composition of matter. The ratio of flavans and Free-B-Ring flavonoids can be adjusted based on the indications and the specific requirements with respect to inhibition of COX vs. LO, requirements of skin penetration, and potency requirements of the product, such as duration of potency required, etc. The quantity of the excipients can be adjusted based on the actual active content of each ingredient. A blending table for each individual batch of product must be generated based on the product specification and QC results for individual batch of ingredients. Additional amounts of active ingredients in the range of 2-5% are recommended to meet the product specification.

Figure 10:
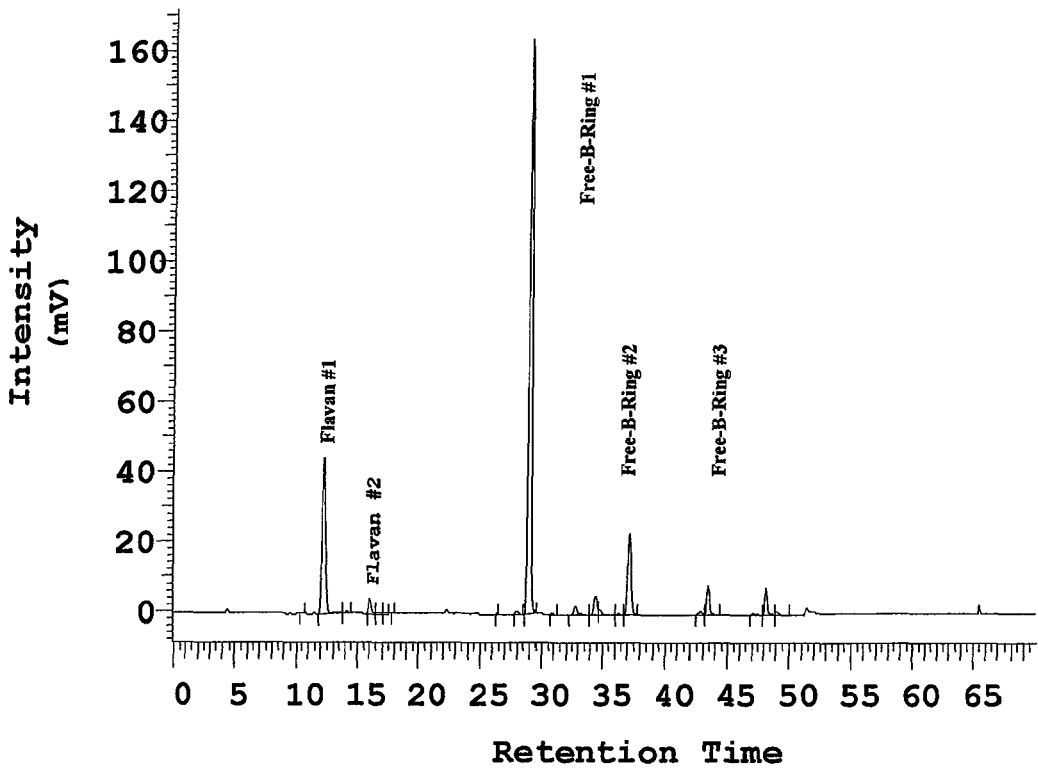
FIG. 10 illustrates the High Pressure Liquid Chromatography (HPLC) chromatogram of a typical formulation comprised of a mixture of Free-B-Ring flavonoids isolated from the roots of *Scutellaria baicalensis* and flavans isolated from the bark of *Acacia catechu* in a ratio of 80:20 carried out under the conditions as described in Example 9.

*Scutellaria baicalensis* root extract (38.5 kg) (lot #RM052302-01) having a Free-B-Ring flavonoid content of 82.2% (baicalin); *Acacia catechu* bark extract (6.9 kg) (lot #RM052902-01) with total flavan content of 80.4%; and excipient (5.0 kg of Candex) were combined to provide a Soliprin™ formulation (50.4 kg) having a blending ratio of 85:15 by weight of the active Free-B-Ring flavonoids and flavans. Table 10 provides the quantification of the active Free-B-Ring flavonoids and flavans of this specific batch of Soliprin™ (Lot#G1702-COX-2), determined using the methods provided in Examples 6 and 8. With reference to Table 10, this specific batch of Soliprin™ contains 86% total active ingredients, including 75.7% Free-B-Ring flavonoids and 10.3% flavans. FIG. 10 illustrates the HPLC chromatogram of a representative Soliprin™ sample which had a blending ratio of 80:20 by weight of the active Free-B-Ring flavonoids and flavans.

TABLE 10

Free-B-Ring Flavonoid and Flavan Content of a Soliprin ™ Formulation

| | Active Components | % Content |
|---|---|---|
| 1. | Flavonoids | |
| a. | Baicalin | 62.5% |
| b. | Minor Flavonoids | |
| i. | Wogonin-7-glucuronide | 6.7% |
| ii. | Oroxylin A 7-glucuronide | 2.0% |
| iii. | Baicalein | 1.5% |
| iv. | Wogonin | 1.1% |
| v. | Chrysin-7-glucuronide | 0.8% |
| vi. | 5-Methyl-wogonin-7-glucuronide | 0.5% |
| vii. | Scutellarin | 0.3% |
| viii. | Norwogonin | 0.3% |
| ix. | Chrysin | <0.2% |
| x. | Oroxylin A | <0.2% |
| c. | Total Free-B-ring Flavonoids | 75.7% |
| 2. | Flavans | |
| a. | Catechin | 9.9% |
| b. | Epicatechin | 0.4% |
| c. | Subtotal Flavans | 10.3% |
| 3. | Total Active Ingredients | 86% |

Using the same approach, the following batches of Soliprin™ were prepared using a combination of a standardized Free-B-Ring flavonoid extract from *Scutellaria baicalensis* roots and a standardized flavan extract from *Acacia catechu* bark having a blending ratio of 12:88 and 15:85, respectively.

*Scutellaria baicalensis* root extract (58.0 g) (lot #RM021203-01) having a Free-B-Ring flavonoid content of 87.9% (as baicalin) and *Acacia catechu* bark extract (442.0 g) (lot #RM050603-01) with total flavan content of 84.9% were blended to provide a Soliprin™ composition (500 g, lot #QJ205-19) having a blending ratio of 12:88 by weight. Utilizing the methods provided in Examples 6 and 8, the Free-B-Ring flavonoid content of (baicalin) was 9.65% and flavan content (total catechin and epicatechin) was 73.2% in this specific batch of Soliprin™ (lot #QJ205-19).

*Scutellaria baicalensis* root extract (300 g) (lot #RM060403-01) having a Free-B-Ring flavonoid content of 82.9% (as baicalin) and *Acacia catechu* bark extract (1700 g) (lot #RM050603-01) with total flavan content of 90.8% were blended to provide a Soliprin™ composition (2000 g, lot #A1904) having a blending ratio of 15:85 by weight. Utilizing the methods provided in Examples 6 and 8, the Free-B-Ring flavonoid content (baicalin) was 15.6% and flavan content (total catechin and epicatechin) was 75.0% in this specific batch of Soliprin™ (lot #A1904).

Example 10

Measurements of Dose Response and $IC_{50}$ Values of 5-LO Enzyme Inhibition from a Formulation of Soliprin™

A Soliprin™ formulation (80:20) was prepared as described in Example 9. (See also Example 14 of U.S. patent application Ser. No. 10/427,746, filed Apr. 30, 2003, entitled "Formulation With Dual COX-2 And 5-Lipoxygenase Inhibitory Activity," which is incorporated herein by reference in its entirety) using a combination of a standardized Free-B-Ring flavonoid extract from *Scutellaria baicalensis* roots and a standardized flavan extract from *Acacia catechu* bark with a blending ratio of 80:20. The sample was titrated in tissue culture media containing THP-1 or HT-29 cells; monocyte cell lines that express COX-1, COX-2 and 5-LOX. A competitive ELISA for Leukotriene B4 (LTB4; Neogen, Inc., Cat #406110) was used to assess the effect of this Soliprin™ formulation on newly synthesized levels of LTB4 present in each cell line as a measure Soliprin™'s inhibitory effect on the 5-LOX pathway. The assay was performed in duplicate by adding 160,000 to 180,000 cells per well in 6-well plates. The Soliprin™ formulation was added to the THP-1 cultures at 3, 10, 30 and 100 µg/mL and incubated overnight (~12-15 hrs) at 37° C. with 5% $CO_2$ in a humidified environment. The results are set forth in FIG. 11, which shows that the production of newly LPS-induced LTB4 was almost completely inhibited by the addition of Soliprin™ to the THP-1 cultures between 3 and 10 µg/mL.

Soliprin™ and ibuprofen, another known 5-LOX inhibitor, were added to the HT-29 cells at 3 µg/mL and incubated 48 hrs at 37° C. with 5% $CO_2$ in a humidified environment. Each treated cell line was then harvested by centrifugation and disrupted by gentle dounce homogenization lysis in physiological buffers. As shown in FIG. 12, Soliprin™ inhibited generation of 80% of the newly synthesized LTB4 in HT-29 cells. Ibuprofen only showed a 20% reduction in the amount of LTB4 over the same time period.

Example 11

Evaluation of the Efficacy of Soliprin™ with In Vivo Mouse Ear Swelling Model

Figure 13:
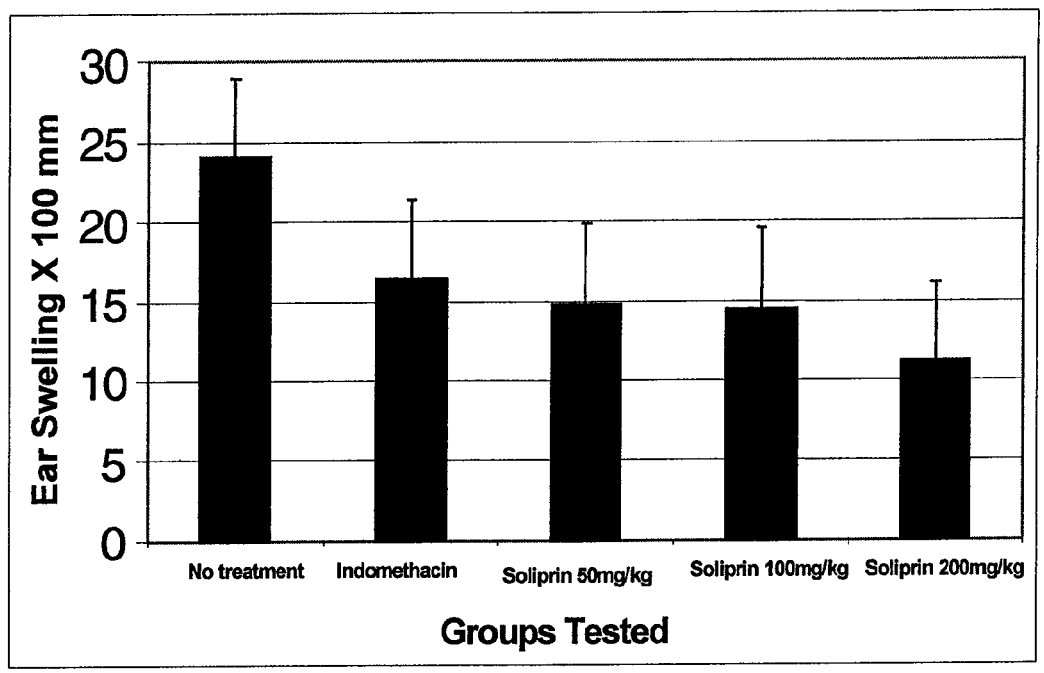
FIG. 13 illustrates graphically ear-swelling data as a measure of inhibition of inflammation as described in Example 11. Soliprin™ produced through the combination of standardized extracts of Free-B-Ring flavonoids isolated from the roots of *Scutellaria baicalensis* and flavans isolated from the bark of *Acacia catechu* in a ratio of 80:20 was compared to untreated mice and mice given indomethacin (1.5 µg/kg) via oral gavage. The data is presented as the difference in micron measurement of the untreated vs. the treated ear lobe for each mouse.

A Soliprin™ formulation was prepared using a combination of a standardized Free-B-Ring flavonoid extract from Scutellaria baicalensis roots and a standardized flavan extract from Acacia catechu bark with a blending ratio of 80:20 as described in Example 9. To test whether this composition could be used to treat inflammation in vivo, the composition was administered by oral gavage to 4-5 week old ICR mice (Harlan Labs) one day before treatment of their ears with arachidonic acid (AA). Test mice were fed dose equivalents of 50, 100 and 200 mg/kg of Soliprin™ suspended in olive oil while control mice were fed only olive oil. The following day, 20 μL of 330 mM AA in 95% alcohol was applied to one ear of each mouse, while alcohol was applied to the other ear as a control. Mice treated with Soliprin™ showed a measurable dose response that tracked with increasing doses of Soliprin™, as demonstrated in FIG. 13. With reference to FIG. 13, the 200 mg/kg dose reduces swelling by over 50% as compared to the "No treatment" control. The 50 mg/kg dose of Soliprin™ was as effective as the 50 mg/kg dose of another strong anti-inflammatory, indomethacin.

Figure 14:
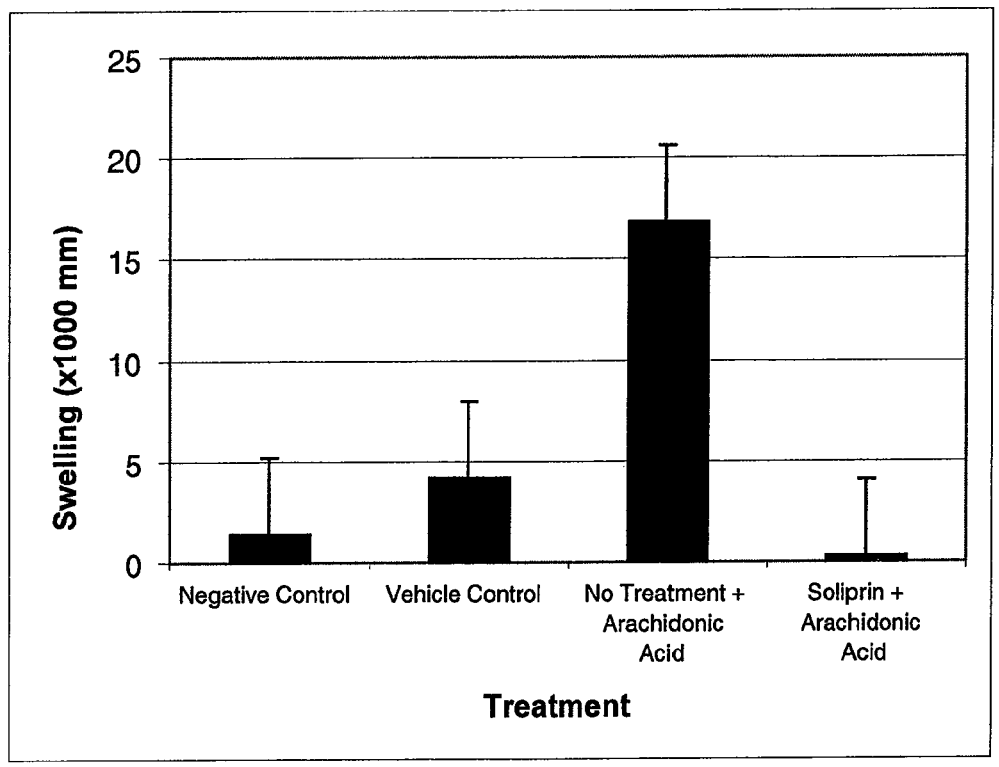
FIG. 14 illustrates graphically the effect of 100 mg/kg of Soliprin™, produced through the combination of standardized extracts of Free-B-Ring flavonoids isolated from the roots of *Scutellaria baicalensis* and flavans isolated from the bark of *Acacia catechu* in a ratio of 80:20 on the AA injected ankles of mice (Soliprin™+arachidonic acid) compared to non-treated mice (no treatment+arachidonic acid), mice without AA injections (negative control) or mice that were injected with the liquid carrier (vehicle control).

In another animal model designed to demonstrate the anti-inflammatory activity of Soliprin™ the 80:20 formulation described above was orally administrated to mice in a dose of 100 mg/kg suspended in olive oil ~12 hours before injection of 20 μL of 100 mM AA in 95% ethanol into the hind ankle joints of 4-5 week old ICR mice (Harlan Labs). The test group was fed the Soliprin™ formulation, while another group was not given the formulation. Control groups included mice that had not received arachidonic acid injections (negative control) and a group that had 95% ethanol without AA injected (vehicle control). These groups were also not given Soliprin™. The results are set forth in FIG. 14. With reference to FIG. 14, the mice given Soliprin™ that were injected with AA showed background levels of swelling as compared to the controls and the untreated arachidonic injected group. These results demonstrate the effectiveness of Soliprin™ for reducing swelling in joints, the site of action.

Example 12

Evaluation of the Efficacy of Soliprin™ in Preventing and Treating Damage Resulting from Exposure of Skin to UV Radiation Six groups of hairless female mice (five mice per group) (Strain SKH-1, Harlan Labs) were irradiated, while anesthetized, for three minutes on three consecutive days with 0.626 mW/cm$^2$ to test the effectiveness of the Soliprin™ formulation in preventing and treating damage resulting from exposure of skin to UV radiation. The Soliprin™ formulation was prepared using a combination of a standardized Free-B-Ring flavonoid extract from Scutellaria baicalensis roots and a standardized flavan extract from Acacia catechu bark with a blending ratio of 80:20 as described in Example 9. The six treatment groups were as follows:

| Group # | |
|---|---|
| 1 | Control group: no treatment before or after UV irradiation |
| 2 | Positive control: treated with a topical application of Sooth-A-Caine (Banana Boat) after UV irradiation |
| 3 | Soliprin ™ Treatment B-1: treated with topical application of 1 mg/mL Soliprin ™ in water before UV irradiation |
| 4 | Soliprin ™ Treatment A-1: treated with topical application of 1 mg/mL Soliprin ™ in water after UV irradiation |
| 5 | Soliprin ™ Treatment B-2: treated with topical application of 5 mg/mL Soliprin ™ in water before UV irradiation |
| 6 | Soliprin ™ Treatment A-2: treated with topical application of 5 mg/mL Soliprin ™ in water after UV irradiation |

Figure 15:
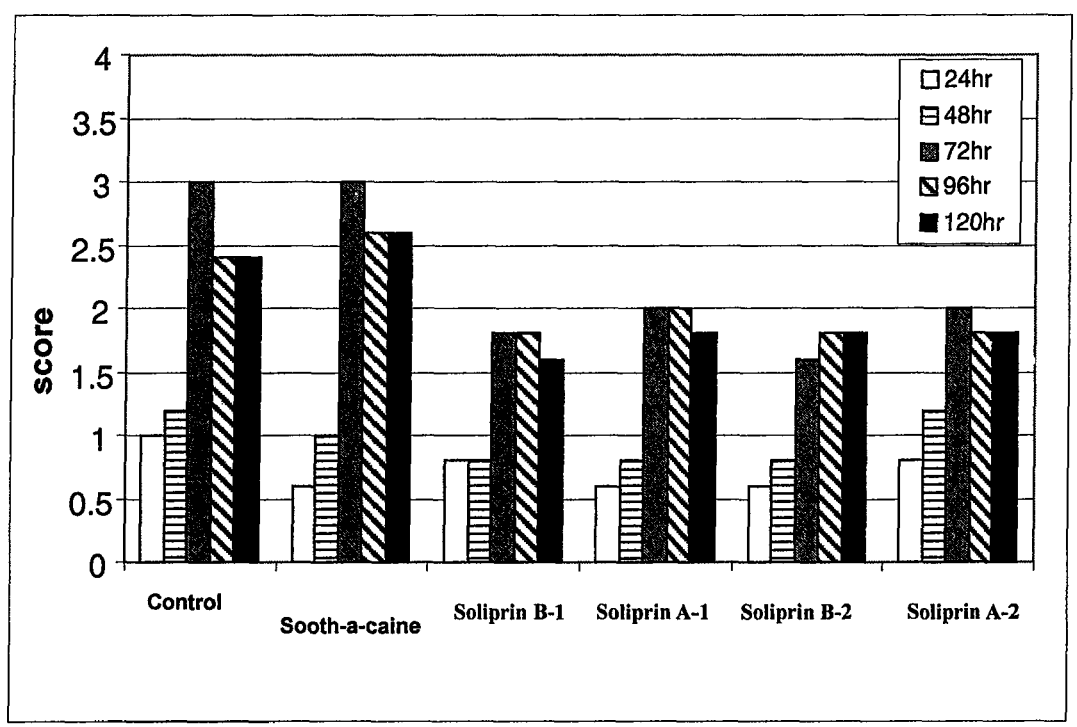
FIG. 15 depicts graphically the changes in hairless mice skin erythema scores in different treatment groups as a function of time following irradiation of the mice with UV light as described in Example 12. The mice in Groups B-1, A-1, B-2 and A-2 were treated with Soliprin™ either before (Groups B-1 and B-2) or after (A-1 and A-2) irradiation. The Soliprin™ was produced through the combination of standardized extracts of Free-B-Ring flavonoids isolated from the roots of *Scutellaria baicalensis* and flavans isolated from the bark of *Acacia catechu* in a ratio of 80:20.

After three days of UV exposure and treatment, the mice were scored on level of erythema (redness) using the following scale: 0—no visible erythema; 1—very slight erythema; 2—well defined erythema; 3—severe erythema; and 4—tumor formation. Erythema was scored by eye for each group. The results are set forth in FIG. 15. With reference to FIG. 15 it can be seen that the control group (Group 1) had severe redness on day 3 (72 hours after the three day exposure to UV radiation). The Sooth-a-caine group also had maximum redness on day 3 (Group 2). The redness for the Soliprin™ treated groups (Groups 3-6) never exceeded a score of 2. These scores, though subjective, show that Soliprin™ is effective in both preventing and treating UV caused skin erythema.

Photographs of representative mice on day four clearly demonstrate differences between the control group, the Sooth-a-cain™ treated groups and the Soliprin™ treated groups (data not shown). The control group and Sooth-a-cain™ treated animals exhibited very extensive patterns and redness of erythema compared to the animals treated with the Soliprin™ formulation both before and after UV exposure. The animals treated before UV irradiation with 5 mg/mL Soliprin™ exhibited the least amount of erythema as compared to all of the other animals.

Example 13

Formulation of the Soliprin™ Composition into a Cream

Two different concentrations of Soliprin™ (0.5% and 1.5% by weight of Soliprin™) (lot #A 1904 as described in Example 9) were formulated as creams as illustrated in the following procedures and in Tables 11 and 12.

Soliprin™ (Lot #A1904) was dissolved in water at room temperature and homogenized with a blender until it was fully dispersed in solution (approximately 5 minutes). At room temperature and without stirring or agitating the solution, Ultrez-21 carbomer was added by sprinkling onto the surface of the solution and allowing it to fully wet (no white areas visible) and fall into the solution. With gentle stirring, the solution was then heated to 40° C. and glycerin was added (Part A). The mixture was then stirred for an additional 5 minutes. The remaining components (Part B) were weighed and heated to 40° C. while mixing. At 40° C., the remaining components (Part B) were added to Part A and the resulting composition was mixed well until homogenous (approximately 5 minutes). The emulsion was cooled to 30° C. and the pH was adjusted to approximately 5.5 (5.3 to 5.7) by titrating with neutralizer while stirring with a stir bar and/or spatula. The emulsion became highly viscous due to neutralization-induced conformational change of the carbomer. The emulsion eventually achieved a suitable viscosity for an emulsion cream. The emulsion cream was then mixed until uniform after which it was poured into a clean storage vessel and stored at 2° to 8° C. for one month.

TABLE 11

Ingredient list for a 0.5% Soliprin Cream

| Phase | Ingredient | % (w/w) | Weight (g) |
|---|---|---|---|
| Aqueous | Water, Purified | 85.00 | 1275.0 |
| | Soliprin (Lot#A1904) | 0.50 | 7.5 |
| | Ultrez 21 Carbomer | 0.50 | 7.5 |
| | Glycerin | 8.00 | 120.0 |

TABLE 11-continued

Ingredient list for a 0.5% Soliprin Cream

| Phase | Ingredient | % (w/w) | Weight (g) |
|---|---|---|---|
| Oil | PEG-7 Glyceryl Cocoate | 3.00 | 45.0 |
| | Caprylic/Capric Triglyceride | 2.67 | 40.0 |
| PH Neutralizer | Sodium Hydroxide (18% w/v), Molecular Biology Grade | 0.00 | 0.0 |
| SUM | 7 Ingredients | 99.7 | 1495.0 |

TABLE 12

Ingredient list in a 1.5% Soliprin Cream

| Phase | Ingredient | % (w/w) | Weight (g) |
|---|---|---|---|
| Aqueous | Water, Purified | 84.00 | 1260.0 |
| | Soliprin (Lot#A1904) | 1.50 | 22.5 |
| | Ultrez 21 Carbomer | 0.50 | 7.5 |
| | Glycerin | 8.00 | 120.0 |
| Oil | PEG-7 Glyceryl Cocoate | 3.00 | 45.0 |
| | Caprylic/Capric Triglyceride | 2.67 | 40.0 |
| pH Neutralizer | Sodium Hydroxide (18% w/v), Molecular Biology Grade | | |
| SUM | 7 Ingredients | 99.7 | 1495.0 |

Example 14

Evaluation of a Soliprin™ Cream for Irritation and Induction of Contact Sensitization by Repetitive Application to Human Skin The Soliprin™ was tested on human skin using an adaptation of the Draize Patch Test (Marzulli and Maibach (1977) Contact Allergy: Predictive Testing in Humans. In Advances in Modern Toxicology, Dermatotoxicology and Pharmacology. Eds. Marzulli, F. N and Maibach, H. I. 4, 353-372). The test sites were located on the upper arm or the paraspinal region of the back. Each test article had an induction site and a challenge site. The induction site was comprised of two sub-sites: an original-site and a move-site. Patches, which contains 0.2 ml of Soliprin cream on each patch, were applied repeatedly to the original-site unless a sufficiently strong irritation reaction developed, requiring the patch to be applied to the move-site. Patches were applied by a clinical research institute and were removed and discarded by the subjects approximately 24 or 48/72 hours later. In the induction phase, repetitive application of the test article to the same site on the skin and a total of 9 induction patches were applied within a 4-week period. The rest period was 10 to 21 days between application of the last induction patch and application of the challenge patch. During this time no test article or any other material was applied to the test area. At the challenge phase, the test article was applied to a naive site on the opposite side of the body and discarded by the subjects approximately 24 or 48 hours later.

Skin responses to each patch application were examined and graded under light supplied by a 100-watt incandescent blue bulb according to the designated scoring scale. In instances where a strong irritation reaction warranted application of the test article to the move-site, residual scores were be recorded through the end of induction (or until resolved if reactions persist after induction is completed) for all previously exposed sites. All skin reactions were recorded. During the challenge phase, skin responses were evaluated approximately 48 and 72 or 96 hours after patch application. Conclusions, with regard to induced sensitivity, were derived primarily from the challenge evaluations.

The two Soliprin™ creams prepared in the Example 13 at 0.5% and 1.5% Soliprin™ concentrations were evaluated according to the above protocol. A total of 120 subjects were recruited for each group. Ninety-seven subjects completed the study for the 0.5% Soliprin™ group and 101 subjects completed the study for 1.5% Soliprin™ group. There was no evidence of sensitization reaction for either the 0.5% and 1.5% Soliprin™ creams. For the 0.5% Soliprin™, during induction, sixteen subjects exhibited occasional occurrences of slight to mild erythema (scores of + and/or 1). At challenge, four subjects exhibited slight to mild erythema at 48 hours that cleared by 96 hours. For 1.5% Soliprin™, during induction, twenty-six subjects exhibited occasional occurrences of slight to mild erythema (scores of + and/or 1). At challenge, one subjects exhibited slight to mild erythema at 48 hours that cleared by 96 hours.

This study demonstrates that Soliprin™ is a safe ingredient that can be applied topically to human skin at an efficacious concentration without causing irritation or sensitization.

The invention claimed is:

1. A method for improving skin appearance, comprising administering to a host in need thereof an effective amount of a composition comprising a mixture of a *Scutellaria* extract enriched for Free-B-ring flavonoids containing baicalin and an *Acacia* extract enriched for flavans containing catechin or epicatechin, wherein the weight ratio of *Scutellaria* extract to *Acacia* extract in the composition ranges from 10:90 to 90:10, respectively.

2. The method of claim 1, wherein each of the *Scutellaria* extract and the *Acacia* extract is independently obtained from a plant part, wherein the plant part is stems, stem barks, trunks, trunk barks, twigs, tubers, roots, root barks, young shoots, seeds, rhizomes, flowers or other reproductive organs or leaves or other aerial parts.

3. The method of claim 1, wherein the *Scutellaria* is selected from *Scutellaria baicalensis, Scutellaria lateriflora, Scutellaria radix* or *Scutellaria orthocalyx*.

4. The method of claim 1, wherein one or more of the Free-B-Ring flavonoids of the *Scutellaria* extract have the following structure

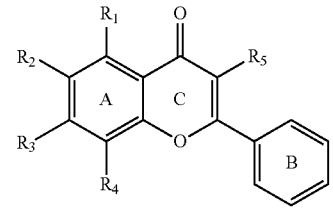

wherein $R_1$, $R_2$, $R_3$, $R_4$, and $R_5$ are independently —H, —OH, —SH, —OR, —SR, —NH$_2$, —NHR, —NR$_2$, —NR$_3^+$X$^-$, a carbon, oxygen, nitrogen or sulfur, glycoside of a single or a combination of multiple sugars, wherein the sugars comprise aldopentoses, methyl-aldopentose, aldohexoses, ketohexose or derivatives thereof; wherein R is an alkyl group having between 1-10 carbon atoms; and X is hydroxyl, chloride, iodide, sulfate, phosphate, acetate, fluoride or carbonate.

5. The method claim 1, wherein the *Acacia* is selected from a *Acacia catechu, Acacia concinna, Acacia farnesiana, Aca-* cia Senegal, *Acacia speciosa, Acacia arabica, A. caesia, A. pennata, A. sinuata. A. mearnsii, A. picnantha, A. dealbata, A. auriculiformis, A. holoserecia* and *A. mangium* plant species.

6. The method of claim 1, wherein one or more of the flavans of the *Acacia* extract have the following structure:

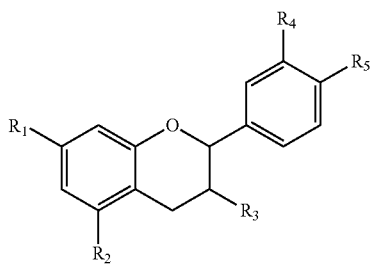

wherein $R_1$, $R_2$, $R_3$, $R_4$ and $R_5$ are independently H, —OH, —SH, —OCH$_3$, —SCH$_3$, —OR, —SR, —NH$_2$, —NRH, —NR$_2$, —NR$_3^+$X$^-$, a gallate ester, an acetate ester, a cinnamoylester, a hydroxyl-cinnamoyl ester, a trihydroxybenzoyl ester, a caffeoyl ester, a carbon, oxygen, nitrogen or sulfur glycoside of a single, or a combination of multiple sugars, wherein the sugars comprise aldopentoses, methyl aldopentose, aldohexoses, ketohexose or derivatives thereof or dimer, trimer or other polymerized flavans;

wherein R is an alkyl group having between 1-10 carbon atoms; and

X is hydroxyl, chloride, iodide, sulfate, phosphate, acetate, fluoride or carbonate.

7. The method of claim 1, wherein the weight ratio of *Scutellaria* extract to *Acacia* extract in the composition is about 12:88, 15:85, or 20:80.

8. The method of claim 1, wherein the improved skin appearance is selected from enhanced youthful appearance, smooth and youthful skin with improved elasticity, enhanced texture, increased flexibility, increased firmness, increased smoothness, or increased suppleness of the skin.

9. The method of claim 1, wherein the improved skin appearance is selected from reduced wrinkles, reduced saggy skin, reduced lines and dark circles around the eyes, or reduced and delayed aging.

10. The method of claim 1, wherein the improved skin appearance comprises enhanced youthful appearance of the skin.

11. The method of claim 1, wherein the composition is administered orally.

12. The method of claim 1, wherein the composition is administered topically.

13. The method of claim 11, wherein the composition is topically administered using a nonsticking gauze, a bandage, a swab, a cloth wipe, a patch, a mask, a protectant, a cleanser, an antiseptic, a solution, a cream, a lotion, an ointment, a gel or an emulsion, a liquid, a paste, a soap, or a powder.

14. The method of claim 1, wherein the composition further comprises an excipient that is dermatologically or cosmetically suitable for topical application.

15. The method of claim 14, further comprising an adjuvant, a carrier, a regular or controlled releasing vehicle, or any combination thereof.

16. The method of claim 1, wherein the composition is administered as a dermatological or cosmetic formulation comprising from 0.001 weight percent (wt %) to 40.0 wt % of the extract mixture in a dermatologically or cosmetically acceptable carrier.

17. The method of claim 16, wherein the dermatological or cosmetic formulation comprises from 0.5 wt % to 1.5 wt % of the extract mixture.

18. A method for treating diseases or conditions of the skin, the method comprising administering to a host in need thereof an effective amount of a composition comprising a mixture of a *Scutellaria* extract enriched for Free-B-ring flavonoids containing baicalin and an *Acacia* extract enriched for flavans containing catechin or epicatechin, wherein the weight ratio of *Scutellaria* extract to *Acacia* extract in the composition ranges from 10:90 to 90:10, respectively, and wherein the diseases or conditions of the skin are cyclooxygenase (COX) and lipoxygenase (LOX) mediated diseases or conditions of the skin.

19. The method of claim 18, wherein each of the *Scutellaria* extract and the *Acacia* extract is independently obtained from a plant part, wherein the plant part is stems, stem barks, trunks, trunk barks, twigs, tubers, roots, root barks, young shoots, seeds, rhizomes, flowers or other reproductive organs or leaves or other aerial parts.

20. The method of claim 18, wherein the *Scutellaria* is selected from *Scutellaria baicalensis, Scutellaria lateriflora, Scutellaria radix* or *Scutellaria orthocalyx*.

21. The method of claim 18, wherein one or more of the Free-B-Ring flavonoids of the *Scutellaria* extract have the following structure:

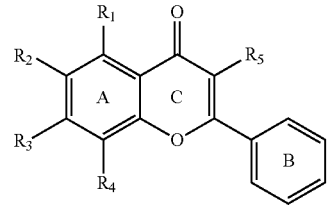

wherein $R_1$, $R_2$, $R_3$, $R_4$, and $R_5$ are independently —H, —OH, —SH, —OR, —SR, —NH$_2$, —NHR, —NR$_2$, —NR$_3^+$X$^-$, a carbon, oxygen, nitrogen or sulfur, glycoside of a single or a combination of multiple sugars, wherein the sugars comprise aldopentoses, methyl-aldopentose, aldohexoses, ketohexose or derivatives thereof;

wherein R is an alkyl group having between 1-10 carbon atoms; and

X is hydroxyl, chloride, iodide, sulfate, phosphate, acetate, fluoride or carbonate.

22. The method claim 18, wherein the *Acacia* is selected from a *Acacia* catechu, *Acacia concinna, Acacia farnesiana, Acacia Senegal, Acacia speciosa, Acacia arabica, A. caesia, A. pennata, A. sinuata. A. mearnsii, A. picnantha, A. dealbata, A. auriculiformis, A. holoserecia* and *A. mangium* plant species.

23. The method of claim 18, wherein one or more of the flavans of the *Acacia* extract have the following structure:

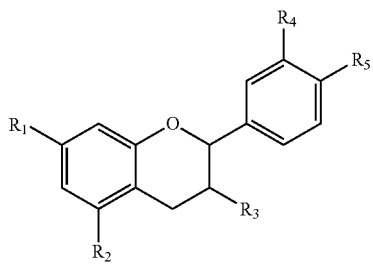

wherein $R_1$, $R_2$, $R_3$, $R_4$ and $R_5$ are independently H, —OH, —SH, —OCH$_3$, —SCH$_3$, —OR, —SR, —NH$_2$, —NRH, —NR$_2$, —NR$_3^+$X$^-$, a gallate ester, an acetate ester, a cinnamoylester, a hydroxyl-cinnamoyl ester, a trihydroxybenzoyl ester, a caffeoyl ester, a carbon, oxygen, nitrogen or sulfur glycoside of a single, or a combination of multiple sugars, wherein the sugars comprise, aldopentoses, methyl aldopentose, aldohexoses, ketohexose or derivatives thereof or dimer, trimer or other polymerized flavans;

wherein R is an alkyl group having between 1-10 carbon atoms; and

X is hydroxyl, chloride, iodide, sulfate, phosphate, acetate, fluoride or carbonate.

24. The method of claim 18, wherein the weight ratio of *Scutellaria* extract to *Acacia* extract in the composition is about 12:88, 15:85, or 20:80.

25. The method of claim 18, wherein the disease or condition of the skin is skin damage resulting from a topical wound or exposure to ultraviolet (UV) radiation, a chemical, heat, wind or a dry environment.

26. The method of claim 18, wherein the disease or condition of the skin is a sun burn, a thermal burn, or a minor inflammatory condition caused by fungal, microbial or viral infection, carcinoma, melanoma or other mammalian skin cancers, acne, sensitive skin, dermatitis, allergy-related conditions, vitiligo, systemic lupus erythematosus, or psoriasis.

27. The method of claim 18, wherein the disease or condition of the skin is a carcinoma, melanoma or other mammalian skin cancer.

28. The method of claim 18, wherein the disease or condition of the skin is an allergy-related condition, dermatitis, vitiligo, systemic lupus erythematosus, or psoriasis.

29. The method of claim 18, wherein the composition is administered orally.

30. The method of claim 18, wherein the composition is administered topically.

31. The method of claim 30, wherein the composition is topically administered using a nonsticking gauze, a bandage, a swab, a cloth wipe, a patch, a mask, a protectant, a cleanser, an antiseptic, a solution, a cream, a lotion, an ointment, a gel or an emulsion, a liquid, a paste, a soap, or a powder.

32. The method of claim 18, wherein the composition further comprises an excipient that is dermatologically or cosmetically suitable for topical application.

33. The method of claim 32, further comprising an adjuvant, a carrier, a regular or controlled releasing vehicle, or any combination thereof.

34. The method of claim 18, wherein the composition is administered as a dermatological or cosmetic formulation comprising from 0.001 weight percent (wt %) to 40.0 wt % of the extract mixture in a dermatologically or cosmetically acceptable carrier.

35. The method of claim 34, wherein the dermatological or cosmetic formulation comprises from 0.5 wt % to 1.5 wt % of the extract mixture.

* * * * *

UNITED STATES PATENT AND TRADEMARK OFFICE
CERTIFICATE OF CORRECTION

PATENT NO. : 8,790,724 B2
APPLICATION NO. : 13/028853
DATED : July 29, 2014
INVENTOR(S) : Qi Jia Page 1 of 1

It is certified that error appears in the above-identified patent and that said Letters Patent is hereby corrected as shown below:

On the title page
Item (56):
"CA 2 484 192 A1 11/2002" should read, --CA 2 484 192 A1 11/2003--.
Item (56):
"CN 1057196 A 10/1993" should read, --CN 1057196 12/1991--.
Item (56):
"CN 1288968 A 09/1999" should read, --CN 1228968 A 09/1999--.
Item (56):
"JP 03-2515518 A 11/1991" should read, --JP 03-251518 A 11/1991--.
Item (56):
"WO 20018/089392 A1 10/2004" should read, --W) 2004/089392 A1 10/2004--.
Item (56):
"JP 10-182415 A 07/1989" should read, --JP 10-182415 A 07/1998--.
Item (56):
"*Encyclopedia of Chinese Traditional Medicine,* ShangHai Science and Technology Press, ShanHai, China, 1998" should read, --*Encyclopedia of Chinese Traditional Medicine,* ShangHai Science and Technology Press, ShangHai, China, 1998--.
Item (56):
"Vāgbhata, Astānga Hrdaya (commentaries by Arunadatta and Hemēdri), 8$^{th}$ Ed., B. H. P. Vaidya, Ed., p. 715, Chaukhambha Orientalia, Varanasi, India, 1998. (9 pages) (with English translation)." should read, --Vāgbhata, Astānga Hrdaya (commentaries by Arunadatta and Hemādri), 8$^{th}$ Ed., B. H. P. Vaidya, Ed., page 715, Chaukhambha Orientalia, Varanasi India, 1998. (9 pages) (with English translation).--.

In the claims
Column 37, Line 52:
"The method of claim 11, wherein the composition is" should read as, --The method of claim 12, wherein the composition is--.

Signed and Sealed this
Fifth Day of April, 2016

Michelle K. Lee
*Director of the United States Patent and Trademark Office*